US011464522B2

(12) United States Patent
Dalton et al.

(10) Patent No.: US 11,464,522 B2
(45) Date of Patent: Oct. 11, 2022

(54) DISTRACTORS HAVING ATTACHABLE PADDLES, IMPACTION DEVICES, AND METHODS FOR USE IN TOTAL ANKLE REPLACEMENT

(71) Applicant: Paragon 28, Inc., Englewood, CO (US)

(72) Inventors: Mark Ray Dalton, Austin, TX (US); Jeffrey Christensen, Everett, WA (US); Aaron Kannard, Los Angeles, CA (US); Daniel J. Lee, Denver, CO (US); Joseph Dogué, Aurora, CO (US)

(73) Assignee: PARAGON 28, INC., Englewood, CO (US)

( * ) Notice: Subject to any disclaimer, the term of this patent is extended or adjusted under 35 U.S.C. 154(b) by 0 days.

(21) Appl. No.: 17/345,402

(22) Filed: Jun. 11, 2021

(65) Prior Publication Data

US 2021/0361293 A1 Nov. 25, 2021

Related U.S. Application Data

(63) Continuation of application No. PCT/US2019/066398, filed on Dec. 13, 2019.
(Continued)

(51) Int. Cl.
*A61B 17/02* (2006.01)
*A61B 17/15* (2006.01)
(Continued)

(52) U.S. Cl.
CPC ............ *A61B 17/15* (2013.01); *A61B 17/025* (2013.01); *A61B 17/1604* (2013.01);
(Continued)

(58) Field of Classification Search
CPC ................................ A61B 17/025–2017/0275
See application file for complete search history.

(56) References Cited

U.S. PATENT DOCUMENTS 3,710,473 A * 1/1973 McElwain ........... B21D 53/085
29/890.038
3,750,652 A * 8/1973 Sherwin ............... A61B 17/025
606/90
(Continued)

FOREIGN PATENT DOCUMENTS

WO 2017164862 9/2017
WO 2019091537 5/2019
(Continued)

OTHER PUBLICATIONS

International Preliminary Report on Patentability for International Application No. PCT/US2019/066398, dated Jun. 8, 2021, 14 pages, International Bureau of WIPO.
(Continued)

*Primary Examiner* — Zade Coley
(74) *Attorney, Agent, or Firm* — Heslin Rothenberg Farley & Mesiti P.C.

(57) ABSTRACT

A distractor system for use in a joint between two bone surfaces of an anatomical structure includes, for example, distractor and at least one detachable tool comprising a body having a proximal portion and a distal portion, said proximal portion being releasably attachable to at least one of a first end of the distractor and/or a second end of the distractor. The distal portion of the detachable tool being operably positionable in the joint between the two bone surfaces of the anatomical structure. The detachable tools may include a detachable paddle.

32 Claims, 48 Drawing Sheets

Related U.S. Application Data

(60) Provisional application No. 62/898,854, filed on Sep. 11, 2019, provisional application No. 62/779,436, filed on Dec. 13, 2018, provisional application No. 62/779,092, filed on Dec. 13, 2018.

(51) Int. Cl.

| | | |
|---|---|---|
| *A61B 90/00* | (2016.01) | |
| *A61B 17/17* | (2006.01) | |
| *A61B 17/16* | (2006.01) | |
| *A61F 2/46* | (2006.01) | |
| *A61F 2/42* | (2006.01) | |

(52) U.S. Cl.
CPC ...... *A61B 17/1682* (2013.01); *A61B 17/1775* (2016.11); *A61B 90/39* (2016.02); *A61F 2/4684* (2013.01); *A61B 2090/3966* (2016.02); *A61F 2/4202* (2013.01)

(56) References Cited

U.S. PATENT DOCUMENTS

| | | | | |
|---|---|---|---|---|
| 4,899,761 | A * | 2/1990 | Brown | A61B 5/224 600/594 |
| 5,429,121 | A * | 7/1995 | Gadelius | F16B 9/054 600/217 |
| 6,241,729 | B1 * | 6/2001 | Estes | A61B 17/025 606/86 R |
| 6,261,296 | B1 * | 7/2001 | Aebi | A61B 17/025 600/219 |
| 6,551,316 | B1 * | 4/2003 | Rinner | A61B 17/8866 606/205 |
| 6,673,116 | B2 | 1/2004 | Reiley | |
| 6,739,068 | B1 * | 5/2004 | Rinner | A61B 17/025 33/783 |
| 6,875,236 | B2 | 4/2005 | Reiley | |
| 7,025,790 | B2 | 4/2006 | Parks | |
| 7,153,281 | B2 * | 12/2006 | Holmes | A61B 5/224 600/594 |
| 8,439,951 | B2 * | 5/2013 | Trautwein | A61B 17/7062 606/249 |
| 8,979,866 | B2 * | 3/2015 | Patel | A61B 17/0206 606/105 |
| 9,351,773 | B2 * | 5/2016 | DiDomenico | A61B 17/8019 |
| 9,402,640 | B2 | 8/2016 | Reynolds et al. | |
| 9,480,571 | B2 | 11/2016 | McGinley et al. | |
| 9,907,561 | B2 | 3/2018 | Luna et al. | |
| 9,918,724 | B2 | 3/2018 | Luna et al. | |
| 9,974,588 | B2 | 5/2018 | Stemniski et al. | |
| 10,058,335 | B2 | 8/2018 | Lee et al. | |
| 2001/0029377 | A1 * | 10/2001 | Aebi | A61B 17/025 606/105 |
| 2003/0105467 | A1 | 6/2003 | Ralph et al. | |
| 2003/0225416 | A1 * | 12/2003 | Bonvallet | A61B 17/025 606/105 |
| 2007/0073405 | A1 * | 3/2007 | Verhulst | A61F 2/4425 623/17.15 |
| 2007/0173858 | A1 | 7/2007 | Engh et al. | |
| 2007/0270783 | A1 | 11/2007 | Zumsteg et al. | |
| 2008/0082169 | A1 | 4/2008 | Gittings et al. | |
| 2009/0209964 | A1 | 8/2009 | Yeung | |
| 2009/0312807 | A1 | 12/2009 | Boudreault et al. | |
| 2010/0217338 | A1 | 8/2010 | Carroll | |
| 2012/0053592 | A1 | 3/2012 | Burgi | |
| 2012/0130376 | A1 | 5/2012 | Loring | |
| 2012/0130434 | A1 | 5/2012 | Stemniski | |
| 2012/0232558 | A1 * | 9/2012 | Berberich | A61B 17/1604 606/84 |
| 2012/0271314 | A1 | 10/2012 | Stemniski | |
| 2013/0085499 | A1 | 4/2013 | Lian | |
| 2014/0018931 | A1 | 1/2014 | Gillard | |
| 2014/0128979 | A1 * | 5/2014 | Womble | A61F 2/4611 623/17.16 |
| 2014/0163563 | A1 | 6/2014 | Reynolds et al. | |
| 2014/0336658 | A1 * | 11/2014 | Luna | A61F 2/4684 606/87 |
| 2015/0182273 | A1 | 7/2015 | Stemniski et al. | |
| 2015/0265265 | A1 * | 9/2015 | Hynes | A61B 17/025 600/219 |
| 2015/0282952 | A1 | 10/2015 | Hes et al. | |
| 2015/0305753 | A1 | 10/2015 | McGinley et al. | |
| 2016/0135815 | A1 | 5/2016 | Loring et al. | |
| 2016/0278754 | A1 | 9/2016 | Todorov et al. | |
| 2018/0146970 | A1 | 5/2018 | Luna et al. | |
| 2018/0177511 | A1 | 6/2018 | Luna et al. | |
| 2018/0177513 | A1 | 6/2018 | Stemniski et al. | |
| 2018/0243023 | A1 | 8/2018 | Stemniski et al. | |
| 2018/0317940 | A1 | 11/2018 | Stemniski et al. | |

FOREIGN PATENT DOCUMENTS

| | | |
|---|---|---|
| WO | 2020124047 A1 | 6/2020 |
| WO | 2020124052 | 6/2020 |
| WO | 2020124056 A1 | 6/2020 |

OTHER PUBLICATIONS

International Search Report and Written Opinion of the International Searching Authority for PCT/US2019/066404 (published as WO 2020/124052), 12 pages, dated Feb. 24, 2020.

Schweitzer et al., Total Ankle Arthroplasty with a Modern Fixed-Bearing System: The Salto Talaris Prosthesis, JBJS Essential Surgical Techniques, retrieved from the internet at https://www.ncbi.nlm.nih.gov/pmc/articles/PMC6407948/pdf/jbjsest-3-e18.pdf, 9 pages, 2013.

International Search Report and Written Opinion of the International Searching Authority for PCT/US2019/066409 (published as WO 2020/124056), 20 pages, dated Feb. 10, 2020.

Dalton, et al., U.S. Appl. No. 17/304,064, filed Jun. 14, 2021, "Total Ankle Replacement Surgical Method," 122 pages, Jun. 14, 2021.

Dogue et al., U.S. Appl. No. 17/345,135, filed Jun. 11, 2021, "Total Ankle Replacement Trial and Preparation Systems, Guides, Instruments and Related Methods," 194 pages, Jun. 11, 2021.

Dogue et al., U.S. Appl. No. 17/345,137, filed Jun. 11, 2021, "Total Ankle Replacement Trial and Preparation Systems", 192 pages, Jun. 11, 2021.

International Search Report and Written Opinion for international patent application No. PCT/US2019/066398 (published as WO2020/124047), 19 pages, dated Apr. 7, 2020.

Non-Final Office Action issued in U.S. Appl. No. 17/345,135, dated Dec. 9, 2021, 16 pages.

Non-Final Office Action issued in U.S. Appl. No. 17/345,137, dated Nov. 15, 2021, 14 pages.

* cited by examiner

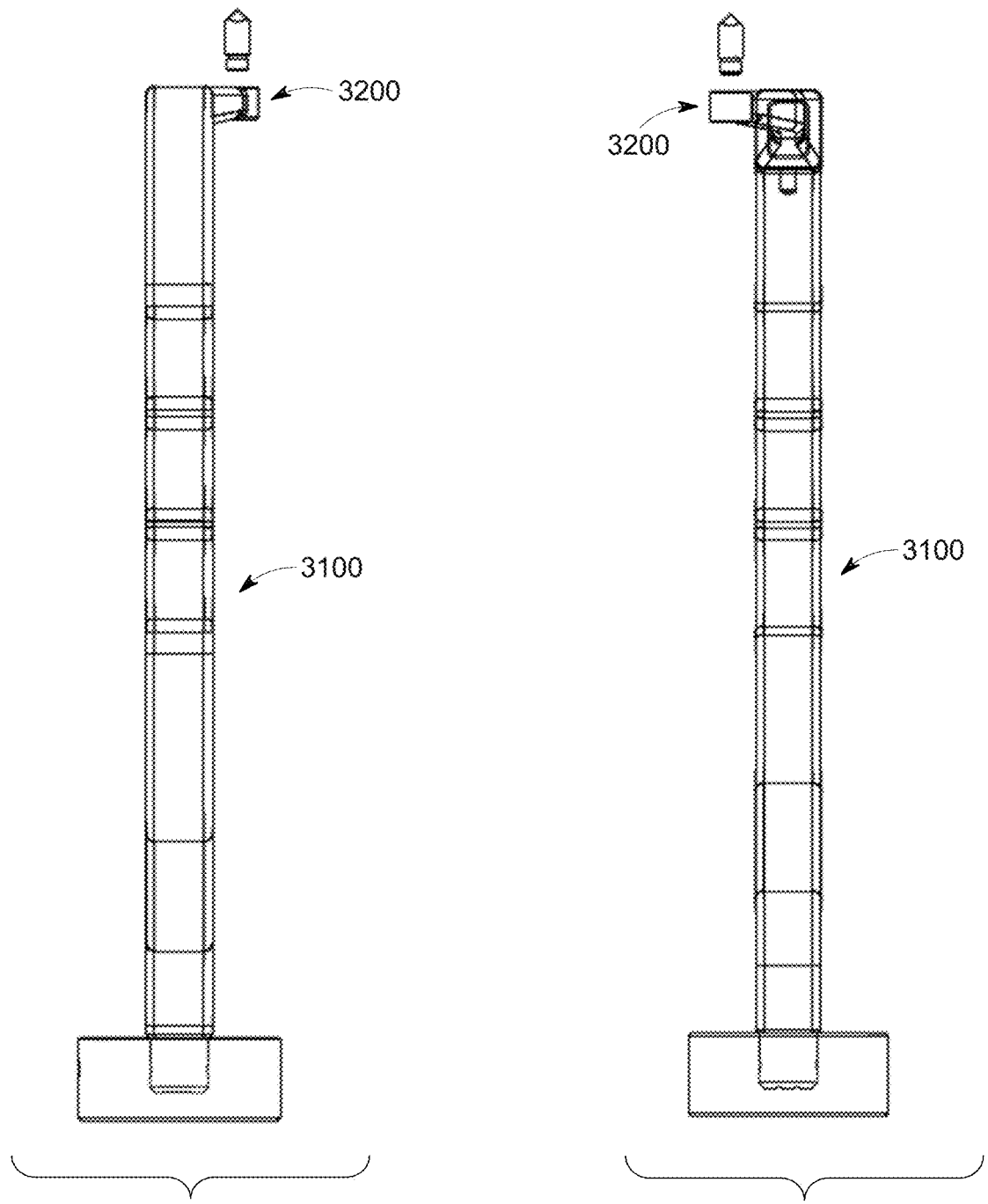

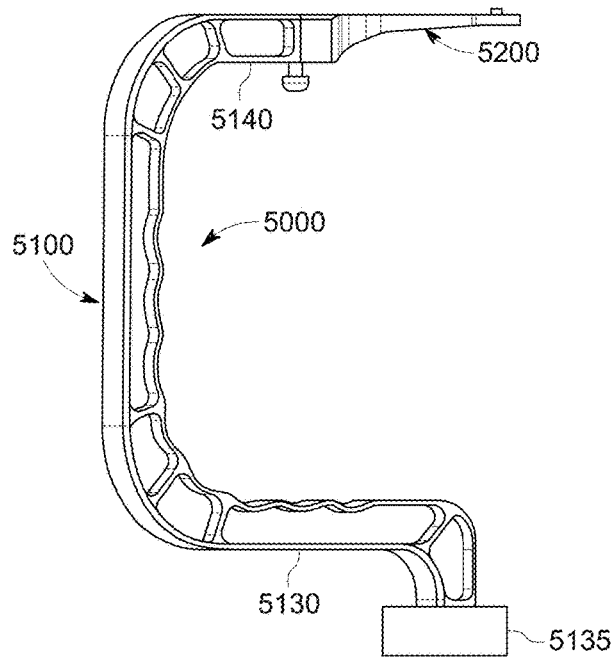
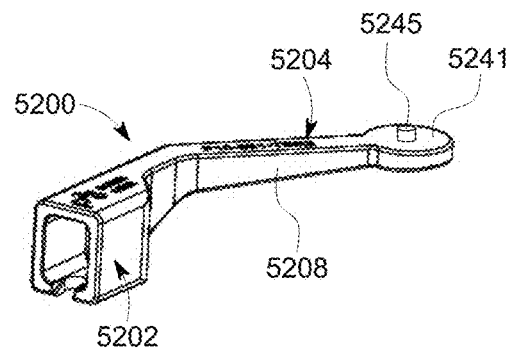
FIG. 91  FIG. 92
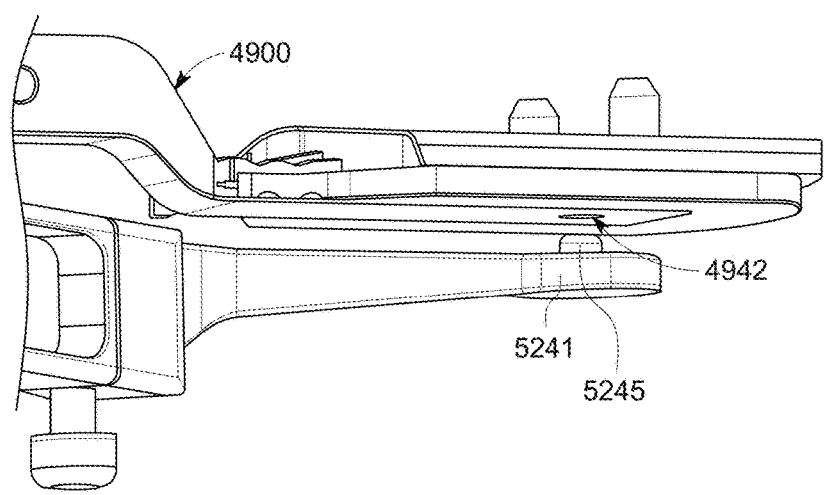
FIG. 93

DISTRACTORS HAVING ATTACHABLE PADDLES, IMPACTION DEVICES, AND METHODS FOR USE IN TOTAL ANKLE REPLACEMENT

CROSS REFERENCE TO RELATED APPLICATIONS

This application is a continuation of International Patent Application No. PCT/US2019/066398, filed on Dec. 13, 2019, entitled "Distractors Having Attachable Paddles, Impaction Devices, And Methods For Use In Total Ankle Replacement", which international patent application claims priority benefit under 35 U.S.C. § 119(e) to U.S. Provisional Patent Application No. 62/898,854, filed Sep. 11, 2019, entitled "Distractors Having Attachable Paddles, Impaction Devices, And Methods For Use In Total Ankle Replacement," claims priority benefit under 35 U.S.C. § 119(e) to U.S. Provisional Patent Application No. 62/779,436, filed Dec. 13, 2018, entitled "Joint Replacement Systems And Methods Of Use And Assembly", and claims priority benefit under 35 U.S.C. § 119(e) to U.S. Provisional Patent Application No. 62/779,092, filed Dec. 13, 2018, entitled "Instruments, Guides and Related Methods for Total Ankle Replacement", which applications are hereby incorporated herein by reference in their entireties.

TECHNICAL FIELD

The present disclosure relates generally to general surgery, podiatric, and orthopaedic instruments used for correcting bone deformities. More specifically, but not exclusively, the present disclosure relates to patient specific instruments, systems, and methods for maintaining, correcting and/or resurfacing joint surfaces such as for use in total ankle replacement.

BACKGROUND

Total ankle replacement (TAR), or ankle arthroplasty, is a surgical procedure to replace deformed and/or damaged articular surfaces of the human ankle joint with a prosthetic joint while preserving the functional range of motion (ROM) of the ankle joint.

Typical TAR prosthesis include a tibial implant component, a talus implant component, and a bearing or insert component positioned between the tibial and talus prosthesis components.

Achieving a stable replacement ankle joint that provides for full articulation/motion (e.g., achieving a range of motion of a typical "healthy" ankle joint) generally requires proper sizing and positioning/orientating/aligning of the tibial implant component with respect to the distal end of a tibia, of the talus implant component with respect to the proximal end of a talus, and of the insert or spacer therebetween.

For example, proper sizing and position/orientation of the tibial prosthesis, the talus prosthesis and the tibial insert of a TAR prosthesis with respect to an ankle joint of a particular patient can prevent overstuffing or understuffing of the replacement ankle joint (and thereby provide full articulation/motion) and can ensure proper coverage of the tibial prosthesis on the tibia and the talus prosthesis on the talus. As another example, the position/orientation/alignment of the tibial prosthesis, the talus prosthesis and the insert or spacer with respect to the mechanical axis of an ankle joint of a particular patient (e.g., the mechanical axis of the tibia) can ensure the mechanical forces of the replacement ankle joint are properly distributed and full and properly-oriented range of motion is achieved.

SUMMARY

Shortcomings of the prior art are overcome and additional advantages are provided through the provision in one embodiment of a distractor system for use in a joint between bone surfaces of an anatomical structure. The distractor system includes, for example, a first pivotable member having a first user engageable arm and an opposite first end, and a second pivotable member having a second user engageable arm and an opposite end. The first pivotable member is pivotably connected to the second pivotable member between the user engageable arms and the ends. A first connecting member has a first end and a second end, and the first end is pivotally connected to the first end of the first pivotable member. A second connecting member has a first end and a second end, and the first end is pivotally connected to the second end of the second pivotable member. A biasing member is operable for biasing the first arm away from the second arm so that the second end of the first connecting member is biased towards the second end of the second member. At least one detachable tool includes a body having a proximal portion and a distal portion. The proximal portion is releasably attachable to at least one of the second end of the first connection member and/or the second end of the second connecting member. The distal portion is operably positionable in the joint between the bone surfaces of the anatomical structure.

In another embodiment, the present disclosure provides a surgical method, which incudes for example, providing the above distractor, attaching a pair of tools to the distractor, and inserting the pair of tools in the joint between the two bone surfaces of the anatomical structure.

In another embodiment, the present disclosure provides a surgical method for use between a first bone surface and a second bone surface of an anatomical structure, which includes, for example, selecting a first detachable tool and a second detachable tool from a plurality of different detachable tools, attaching the first detachable tool to a first connector of a distractor, attaching the second detachable tool to a second connector of the distractor, using the distracter to insert the first detachable tool and the second detachable tool between the first bone surface and the second bone surface of the anatomical structure.

In another embodiment, the surgical method may further include providing an implant trialing and cutting guide, inserting the implant trialing and cutting guide between a resected portion of the first bone and the first paddle, and wherein the using includes using the distractor and the first detachable tool to seat the implant trialing and cutting guide in the resected portion of the first bone. The surgical method may further include selecting a third detachable tool having at least one cutting and/or punch pin, removing the first detachable tool from the first connector of the distractor, attaching the third detachable tool to the first connector of the distractor, passing the at least one cutting and/or punch pin through the implant trialing and cutting guide seated in the resected portion of the first bone, and using the distractor to force the at least one cutting and/or punch pin into the resected portion of the first bone. Still other embodiments of the surgical method may further include removing the third detachable tool from the first connector of the distractor, removing the implant trialing and cutting guide from the resected portion of the first bone, attaching the fourth detachable tool to the first connector of the distractor, inserting an implant component in the resected portion of the first bone and the positioning an impaction protector between the implant component and the fourth detachable tool, and using the distractor to seat the implant component in the resected portion of the first bone.

In another embodiment, the present disclosure provides a detachable tool to a first movable end or a second movable end of a distractor for use between bone surfaces of an anatomical structure, which includes, for example, a body having a proximal portion and a distal portion, the proximal portion configured for releasably attaching to the first movable end of the distractor, and the distal portion includes a planar member having a first planar surface and a second planar surface.

In another embodiment, the present disclosure provides a detachable resection guide tool releasably attachable to a first movable end and/or a second movable end of a distractor for use between bone surfaces of an anatomical structure. The detachable resection guide tool may include, for example, a body having a proximal portion and a distal portion. The proximal portion is configured for releasably attaching to the first movable end of the distractor, and the distal portion comprising a resection guide.

In another embodiment, the present disclosure provides a detachable resection guide tool releasably attachable to a first movable end of a distractor for use between bone surfaces of an anatomical structure. The detachable resection guide tool may include, for example, a body having a proximal portion and a distal portion. The proximal portion is configured for releasably attaching to the first movable end of the distractor, and the distal portion comprising an implant trialing and cutting guide.

In another embodiment, the present disclosure provides an implant impaction system for use in installing an implant, which includes, for example, a body having a U-shaped configuration defining a central handle portion, a proximal impact portion, and a distal portion. A detachable projecting member having a proximal portion and a distal portion, the proximal portion releasably attachable to the distal portion of the body. An impaction protector is supportable on the distal portion of the projecting member. The impaction protector is positionable between the implant and the projecting member during implanting of the implant.

Additional features are realized through the techniques of the present disclosure. Other embodiments and aspects of the present disclosure are described in detail herein and are considered a part of the claimed disclosure.

These and other objects, features and advantages of this disclosure will become apparent from the following detailed description of the various aspects of the disclosure taken in conjunction with the accompanying drawings.

BRIEF DESCRIPTION OF THE DRAWINGS

The subject matter which is regarded as the disclosure is particularly pointed out and distinctly claimed in the concluding portion of the specification. The disclosure, however, may best be understood by reference to the following detailed description of various embodiments and the accompanying drawings in which:

FIG. 58 is an exploded right side elevational view of the impaction system of FIG. 54, according to an embodiment of the present disclosure;

FIG. 59 is an exploded left side elevational view of the impaction system of FIG. 54, according to an embodiment of the present disclosure;

FIG. 91 is a perspective view of an impaction system, according to an embodiment of the present disclosure;

FIG. 92 is an enlarged perspective view of the detachable projecting member of the impaction system of FIG. 91, according to an embodiment of the present disclosure;

FIG. 93 is an enlarged, exploded perspective view of the detachable projecting member of the impaction system of FIG. 91 along with a detachable tibial implantation paddle, a tibial impaction protector, and a tibial implant component, according to an embodiment of the present disclosure;

DETAILED DESCRIPTION

Figure 1:
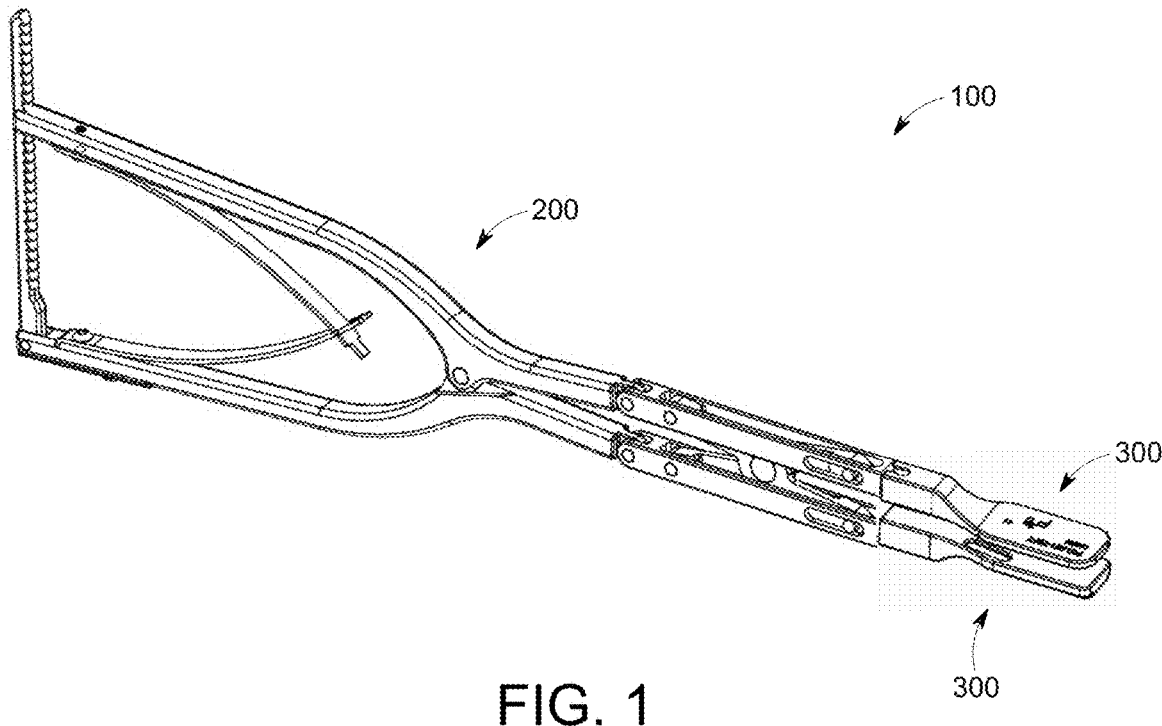
FIG. 1 is a perspective view of a distractor system having a distractor and detachable paddles, according to an embodiment of the present disclosure.

The present disclosure is directed to instruments, guides, systems and related methods for, for example, total ankle replacement prostheses. The instruments, guides, systems and related methods may facilitate preparation of a tibia and/or talus of a patient for implantation of a total ankle prosthesis therein. The instruments, guides, systems and related methods may also facilitate selection of a particular size of a tibial trialing component, tibial implant component, a talus trialing component, a talus implant component, and/or a tibial insert of the total ankle prosthesis that suits the patient.

In this detailed description and the following claims, the words proximal, distal, anterior or plantar, posterior or dorsal, medial, lateral, superior and inferior are defined by their standard usage for indicating a particular part or portion of a bone, joint (or any other anatomical structure) or implant according to the relative disposition of the natural bone, joint (or any other anatomical structure) or directional terms of reference. For example, "proximal" means the portion of a device or instrument nearest the torso, while "distal" indicates the portion of the device or instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot and/or ankle, the term "dorsal" refers to the top of the foot and the term "plantar" refers the bottom of the foot.

Similarly, positions or directions may be used herein with reference to anatomical structures or surfaces. For example, as the current instruments, guides, systems and related methods (and components thereof) are described herein with reference to use with the bones of the ankle, the bones of the foot, ankle and lower leg may be used to describe the surfaces, positions, directions or orientations of the instruments, guides, systems and related methods (and components thereof). Further, the instruments, guides, systems and related methods, and the aspects, components, features and the like thereof, disclosed herein may be described with respect to one side of the body (e.g., the left or right ankle) for brevity purposes. However, as the human body is relatively symmetrical or mirrored about a line of symmetry (midline), it is hereby expressly contemplated that the instruments, guides, systems and related methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the instruments, guides, systems and related methods, and the aspects, components, features and the like thereof, described herein with respect to the right ankle of a patient may be mirrored so that they likewise function with the left ankle of the patient. Further, the instruments, guides, systems and related methods, and the aspects, components, features and the like thereof, disclosed herein are described with respect to the ankle for brevity purposes, but it should be understood that the instruments, guides, systems and related methods (and components thereof) may be used with other joints of a human body (or other mammalian body) having similar structures.

FIG. 1 illustrates a distractor system 100, according to an embodiment of the present disclosure. The distractor system 100 is operable for use in separating bone surfaces of an anatomical structure. In the various embodiments as descried below, the distractor systems of the present disclosure are operable, for example, for separating bones, trialing implants, and installing implants, such as for use in a total ankle replacement prosthesis. In this illustrated embodiment, the distractor system 100 may include a distractor 200 and a plurality detachable paddles 300.

Figure 2:
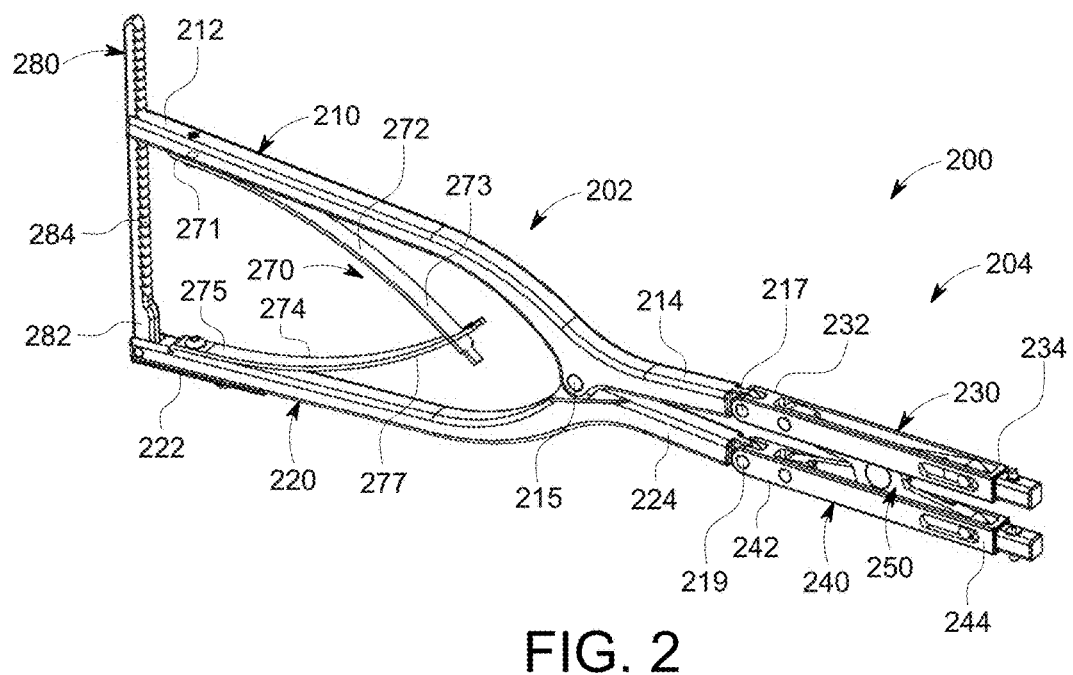
FIG. 2 is a perspective view of the distractor of FIG. 1, according to an embodiment of the present disclosure.
Figure 3:
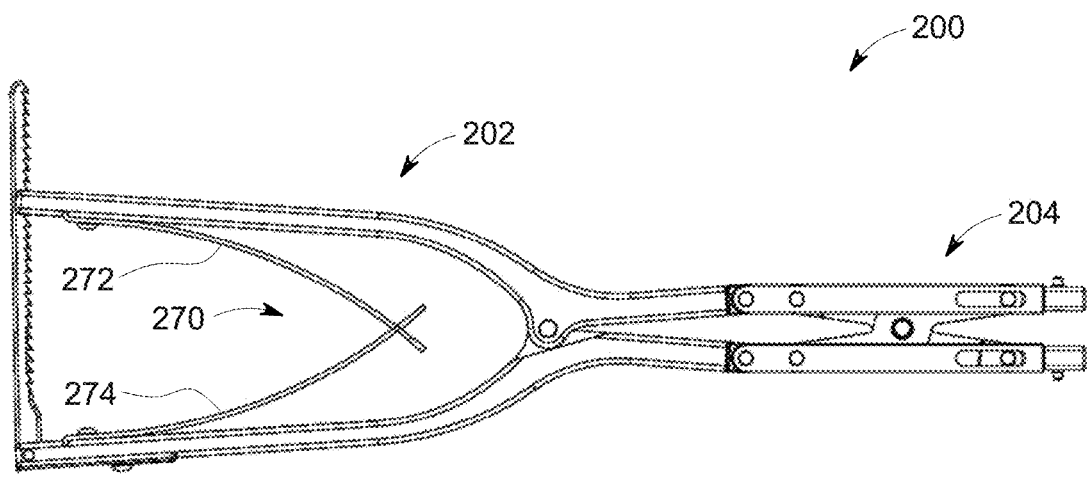
FIG. 3 is a front elevational of view the distractor of FIG. 1, according to an embodiment of the present disclosure.
Figure 4:
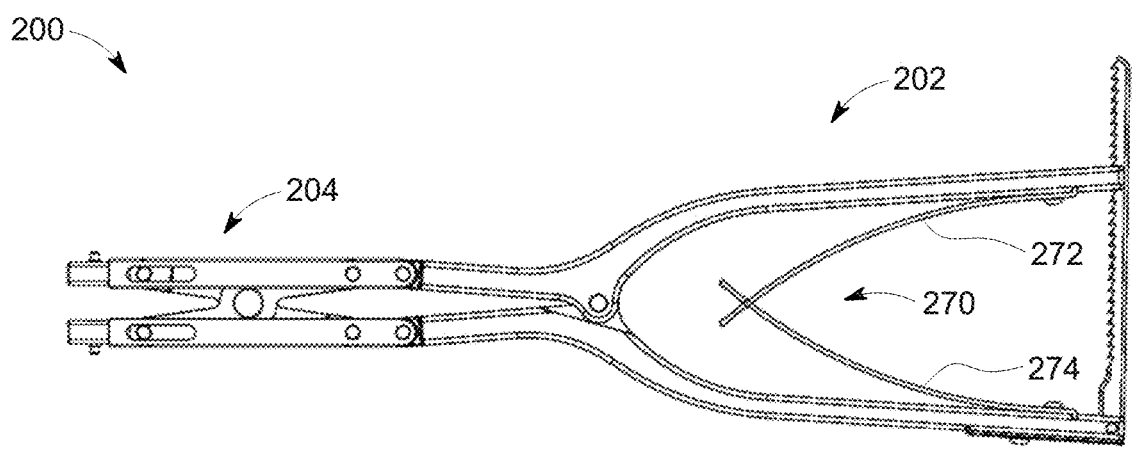
FIG. 4 is a rear elevational view of the distractor of FIG. 1, according to an embodiment of the present disclosure.
Figure 5:
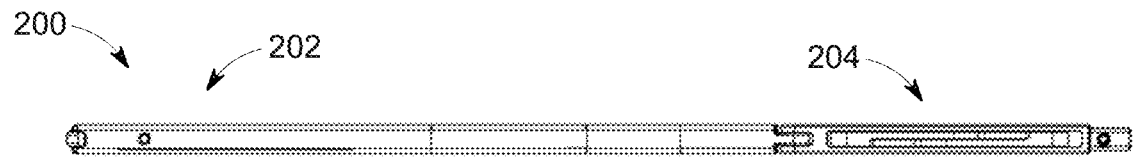
FIG. 5 is a top view of the distractor of FIG. 1, according to an embodiment of the present disclosure.
Figure 6:
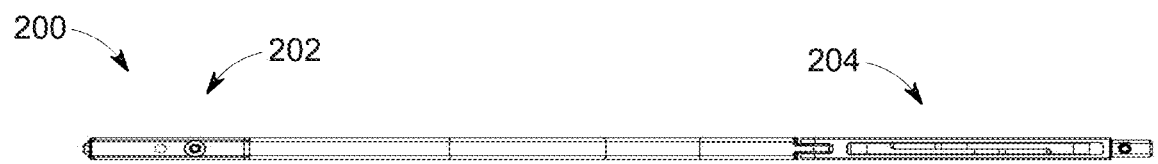
FIG. 6 is a bottom view of the distractor of FIG. 1, according to an embodiment of the present disclosure.
Figure 7:
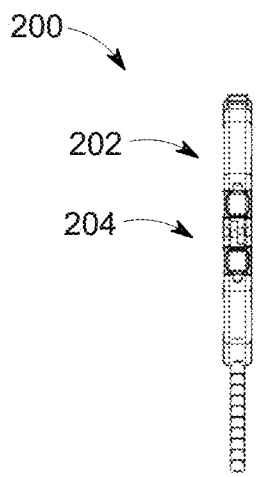
FIG. 7 is right side elevational view of the distractor of FIG. 1, according to an embodiment of the present disclosure.
Figure 8:
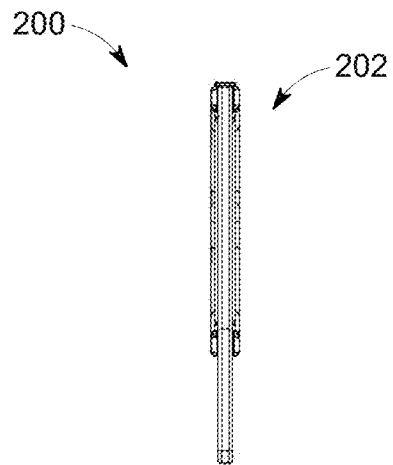
FIG. 8 is left side elevational view of the distractor of FIG. 1, according to an embodiment of the present disclosure.

As shown in FIGS. 2-8, the distractor 200 may include a user operable portion or pivotable portion 202 and a connecting portion 204. As shown in FIG. 2, the pivotable portion 202 may generally include a first pivotable member 210 and a second pivotable member 220. The first pivotable member 210 includes a first user engageable arm 212 and an opposite first end 214. The second pivotable member 220 includes a second user engageable arm 222 and an opposite second end 224. The first pivotable member 210 is pivotably connected to the second pivotable member 220. For example, the first pivotable member 210 may be pivotally connected via a pin 215 disposed between the user engageable arms 212 and 222 and the end ends 214 and 224.

The connecting portion 204 may include a first connecting member 230 and a second connecting member 240. In this illustrated embodiment, the first connecting member 230 and a second connecting member 240 may be operably connected via a scissors mechanism 250, which maintains the first connecting member parallel to the second connecting member 240 as the first connecting member 230 and a second connecting member 240 are moved towards and away from each other.

The first connecting member 230 may be an elongated member having a first end 232 and a second end 234. The first end 232 is pivotally connected to the first end 214 of the first pivotable member 210 via a pin 217. The second connecting member 240 may be an elongated member having a first end 242 and a second end 244. The first end 242 is pivotally connected to the second end 224 of the second pivotable member 220 via pin 219.

Figure 9:
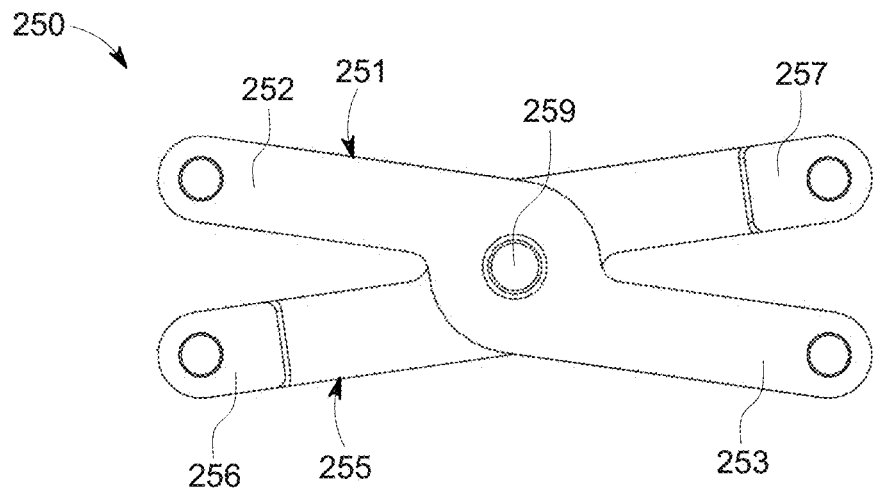
FIG. 9 is an enlarged side elevational view of the scissors mechanism of the distractor of FIG. 1, according to an embodiment of the present disclosure.

With reference to FIG. 9, the scissors mechanism 250 may include a pair of crisscrossing members 251 and 255. The first crisscrossing member 251 includes a first end 252 and a second end 253. The second crisscrossing member 255 includes a first end 256 and a second end 257. The centers of the crisscrossing member 251 and 255 are pivotally attached with a pin 259.

Figure 10:
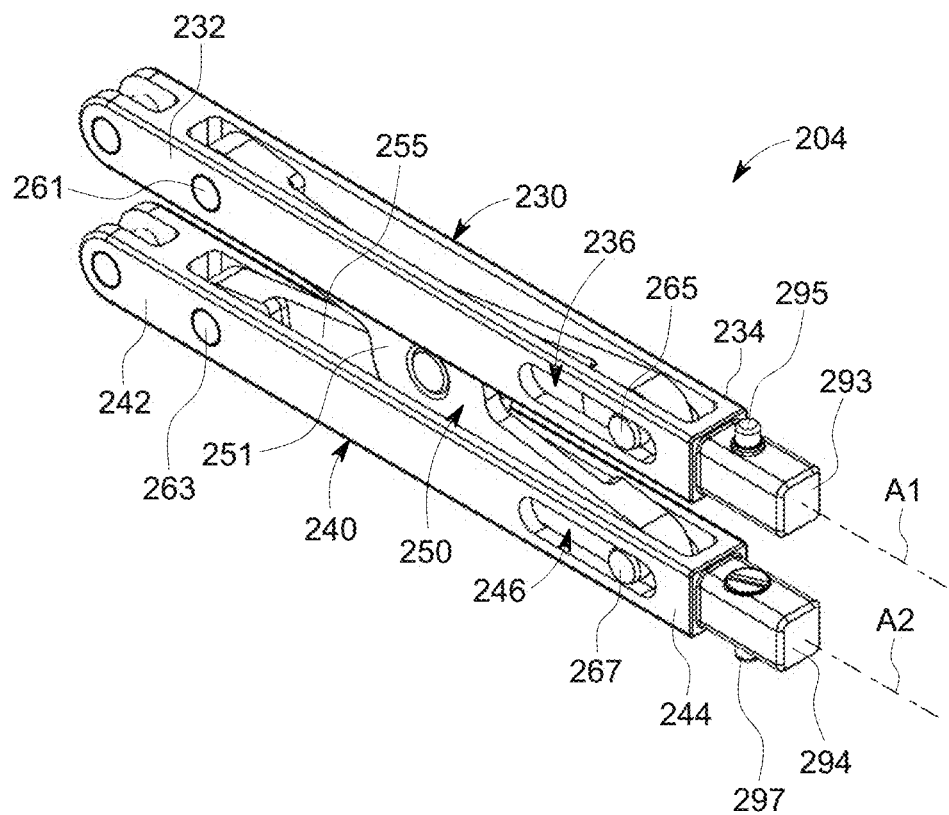
FIG. 10 is an enlarged perspective view of the first and second connecting members and scissors mechanism of the distractor of FIG. 1, according to an embodiment of the present disclosure.

As shown in FIG. 10, the connecting members 230 and 240 of the connecting portion 204 may be generally hollow for receiving the scissors mechanism 250 therein. The end 252 (FIG. 9) of the first crisscrossing member 251 of the scissors mechanism 250 is operably pivotally attachable to the first connecting member 230 via a pin 261. The end 256 (FIG. 9) of the second crisscrossing member 255 of the scissors mechanism 250 is operably pivotally attachable to the second connecting member 240 via a pin 263. The end 257 (FIG. 9) of the first crisscrossing member 251 of the scissors mechanism 250 is operably slidably pivotally attachable to the first connecting member 230 via a pin 265. The end 253 of the second crisscrossing member 253 of the scissors mechanism is operably slidably pivotally attachable to the second connecting member 240 via a pin 267. As shown in FIG. 10, the pin 265 may be constrained to travel within a track 236 in the first connecting member 230, and the pin 267 may be constrained to travel within a track 246 in the second connecting member 240. Thus, movement of the end 214 and 224 (FIG. 2) of arms 210 and 220 (FIG. 2), respectively, towards and away from each other causes ends 232 and 242 or connecting members 230 and 240 to move towards and away from each other.

With reference again to FIGS. 2-4, a biasing member 270 may include a first spring member 272 and a second spring member 274. An end 271 of spring member 272 may be attached to the end 212 of the arm 210 and an end 275 of spring member 274 may be attached to the end 222 of the arm 220. Second ends 273 and 276 may be operably connected to place the spring member 270 in compression so that the ends 212 of the arms 222, respectively, are biased away from each other. Such a configuration results in the ends 214 and 224 being biased toward each other. The distractor 200 may include a ratchet 280 having a first end 282 pivotally attached to the second arm 220 and teeth 284 selectively releasably attachable with the first arm 210 to maintain the ends 214 and 224, and thus the detachable paddles 300 (FIG. 1) in a fixed relationship to each other. For example, the ratchet 280 may allow locking the distractor 200 in position.

With reference again to FIG. 10, the second end 234 of the first connector 230 may include a first post 293, and the second end 244 of the second connector 240 may include a second post 294. The first post 293 may define a first axis A1, the second post 294 may define a second axis A2. The first axis and the second axis may be disposed and maintained parallel to each other. The first post 293 may have a square cross section and the second post 294 may have a square cross section. In some embodiments, the first post 293 may include a laterally-extending projection 295 and the second post 294 may include a laterally-extending projection 297. As described below, the detachable paddles 300 (FIG. 1) may be configured to be connected, orientated, and secured on to the posts of the connecting members.

FIGS. 11-18 illustrate the detachable paddle 300, according to an embodiment of the present disclosure. For example, a pair of the detachable paddles 300 may be employed as shown in FIG. 1. As described below, a surgeon may be provided with a plurality of differently sized and shaped detachable paddles, which detachable paddles may be selected by the surgeon depending the operation to be performed in using the distractor.

Figure 11:
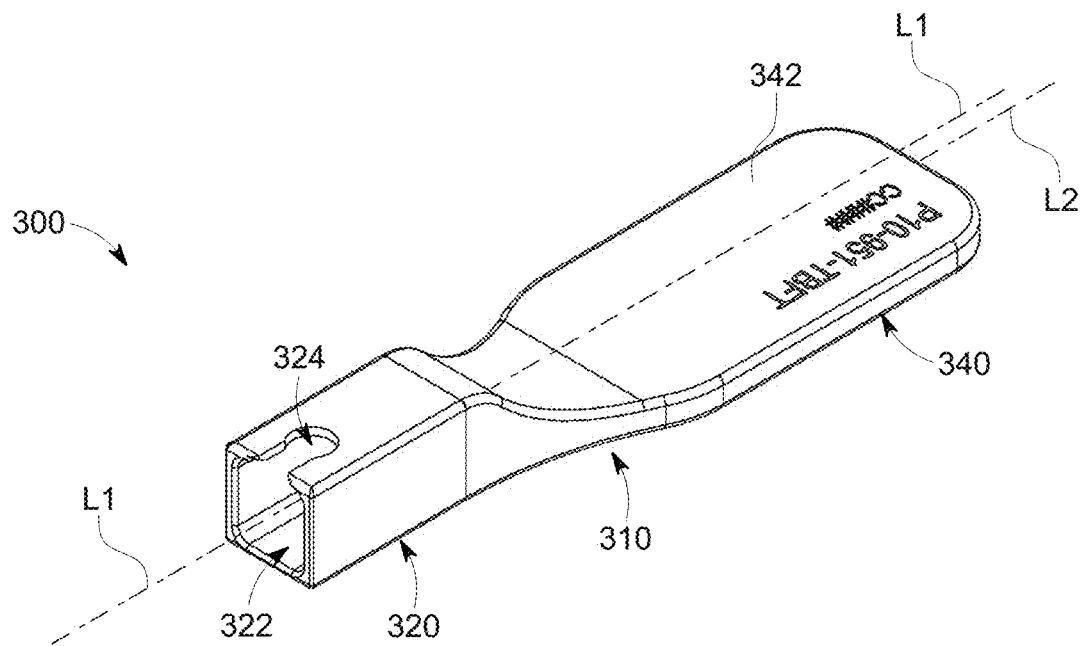
FIG. 11 is a top perspective view of one of the detachable paddles of the distractor system of FIG. 1, according to an embodiment of the present disclosure.
Figure 12:
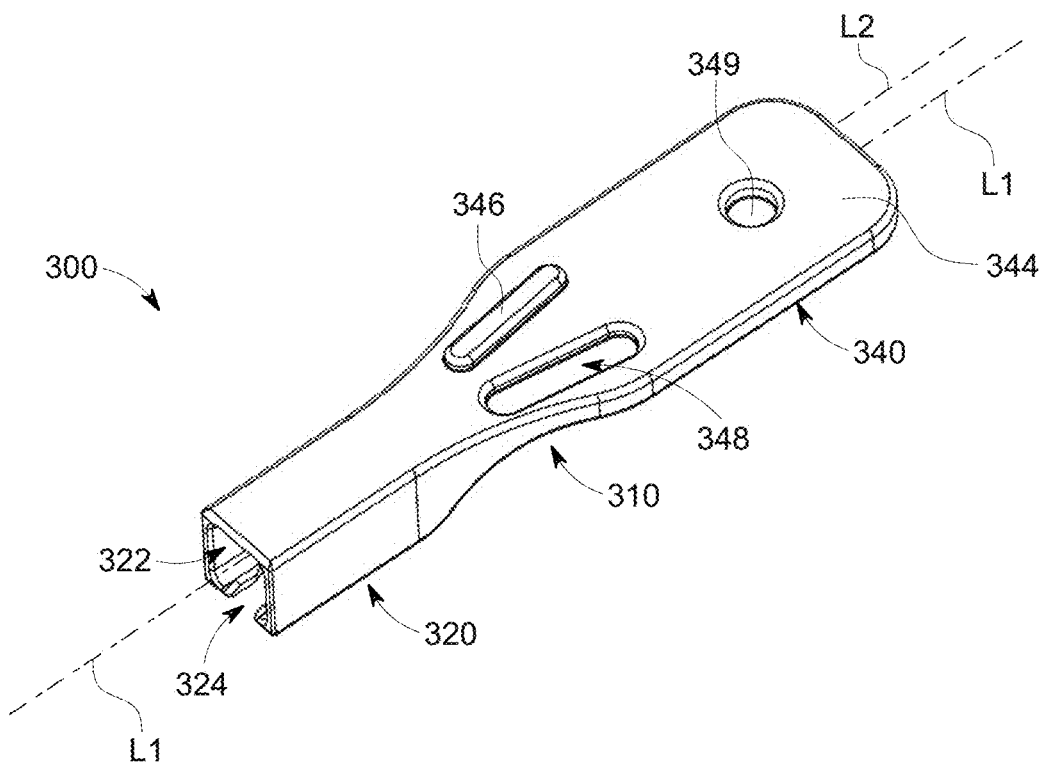
FIG. 12 is a bottom perspective view of the detachable paddle of FIG. 11, according to an embodiment of the present disclosure.

In this illustrated embodiment, for example, the detachable paddle 300 may include a body 310 having a proximal portion 320 and a distal portion 340. With reference to FIGS. 11 and 12, the proximal portion 320 may be configured for releasably attaching to the first post 293 (FIG. 10) and/or the second post 294 (FIG. 10) of the distractor 100 (FIG. 1). The distal portion 340 may include a generally planar member having a first or top planar surface 342 (FIG. 11) and a second or bottom planar surface 344 (FIG. 12).

The proximal portion 320 of the detachable paddle 300 may include a recess 322, which is supportable on the first post 293 (FIG. 10) and the second post 294 (FIG. 10). The proximal portion 320 may also include a cutout 324 for receiving the laterally-extending projections 295 or 297 (FIG. 10). The recess 322 may have a square cross-section.

Figure 13:
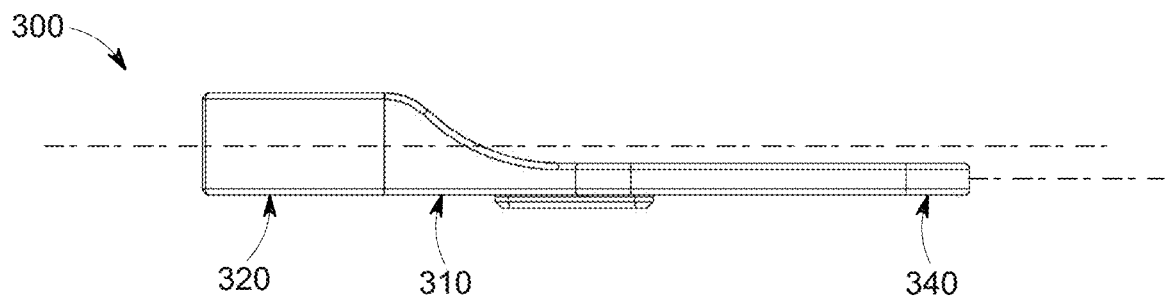
FIG. 13 is a front elevational view of the detachable paddle of FIG. 11, according to an embodiment of the present disclosure.
Figure 14:
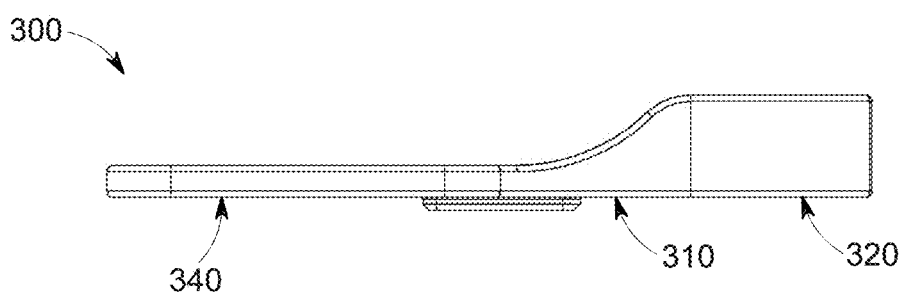
FIG. 14 is a rear elevational view of the detachable paddle of FIG. 11, according to an embodiment of the present disclosure.
Figure 15:
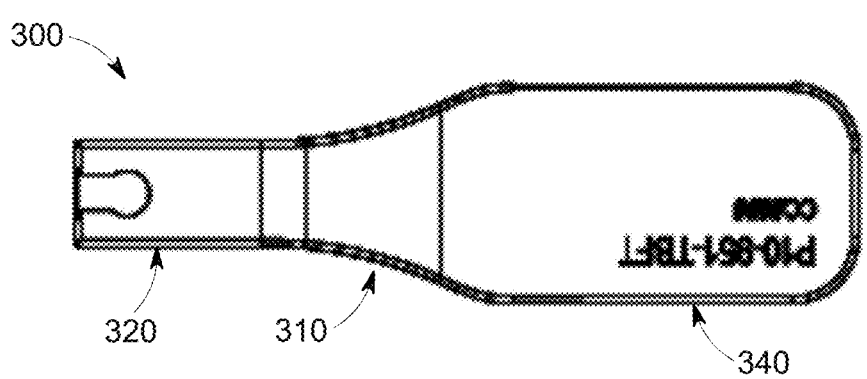
FIG. 15 is a top view of the detachable paddle of FIG. 11, according to an embodiment of the present disclosure.
Figure 16:
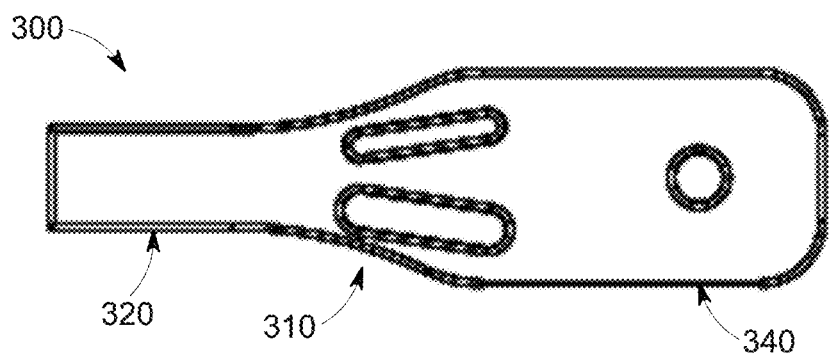
FIG. 16 is a bottom view of the detachable paddle of FIG. 11, according to an embodiment of the present disclosure.
Figure 17:
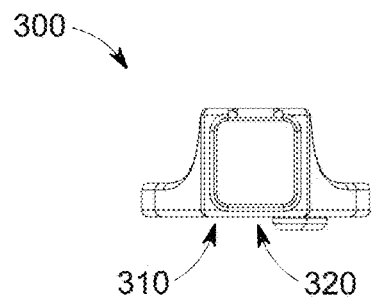
FIG. 17 is left side elevational view of the detachable paddle of FIG. 11, according to an embodiment of the present disclosure.
Figure 18:
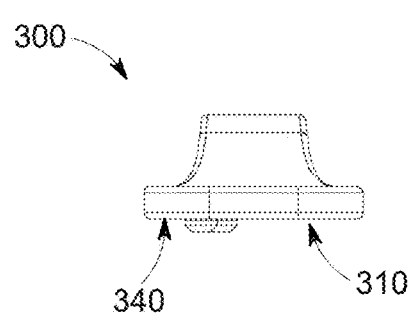
FIG. 18 is right side elevational view of the detachable paddle of FIG. 11, according to an embodiment of the present disclosure.

As shown in FIG. 12, the second planar surface 344 of the detachable paddle 300 may include a raised land 346 extending from the second planar surface 344 and a recess 348 extending into the second planar surface 344. With reference to FIGS. 11 and 13, the proximal portion 322 of the detachable paddle 300 may define a longitudinal axis L1 and the planar member 340 of the detachable paddle 300 may define a longitudinal axis L2. The longitudinal axis L2 of the planar member 340 may be offset from the longitudinal axis L1 of the proximal portion 320.

With reference again to FIG. 12, the raised land 346 may be an elongated raised land that is disposed on one side of the longitudinal axis L1 and the longitude axis L2 of the body 310 and the recess 348 may be an elongated recess disposed on an opposite side of the longitudinal axes L1 and L2 of the body 310. In other embodiments, the elongated raised land 346 may be angled away from the elongated recess 348. In some embodiments, the raised land and recess may be disposed so that a pair of detachable paddles 300 may be positioned with second planar surfaces 344 abutting and aligned with each other and the land of one detachable paddle being received in the recess of the other detachable paddle, and the recess of one detachable paddle being received around the land of the other detachable paddle. The second planar surface of the detachable paddle may further include a second recess 349 such as a countersunk hole.

Figure 19:
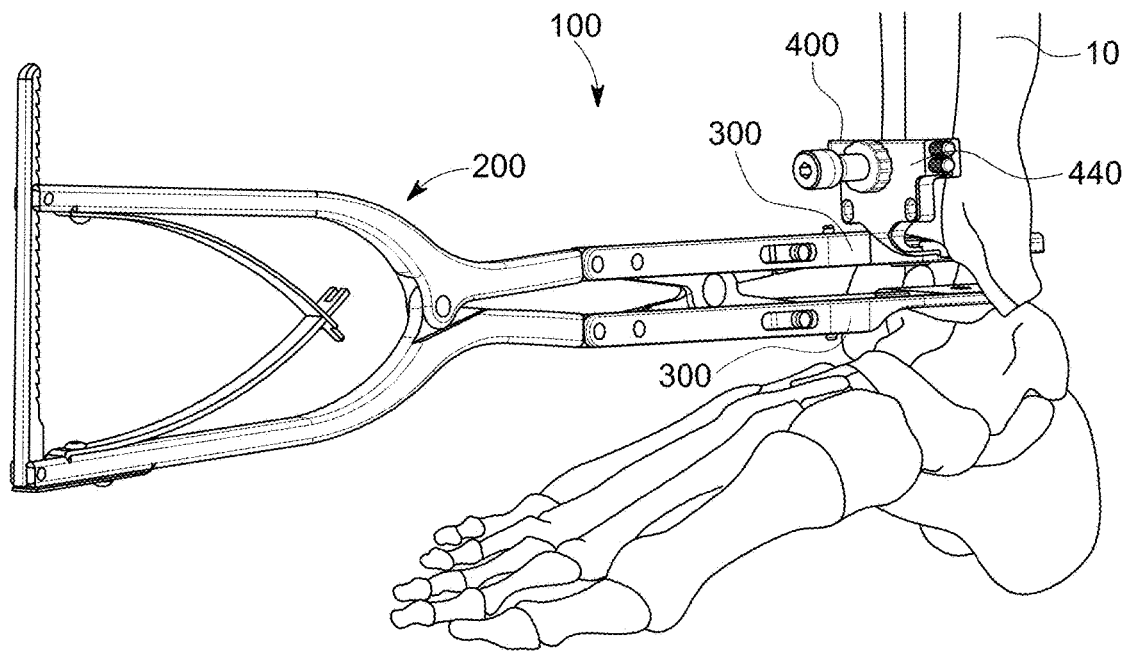
FIG. 19 is perspective view of a tibial implant trialing and cutting guide and the distractor assembly of FIG. 1, according to an embodiment of the present disclosure.

With reference to FIG. 19, the distractor 200 and a pair of the detachable paddles 300 along with a tibial trial component 400 may be operably used by a surgeon to facilitate the selection of a properly sized tibial trialing component for use in a total ankle replacement (TAR) procedure based on the size/configuration of the ankle of a particular patient. For example, the tibial trialing component 400 may correspond, in at least one aspect, to a tibial implant component of the TAR prosthesis.

Figure 20:
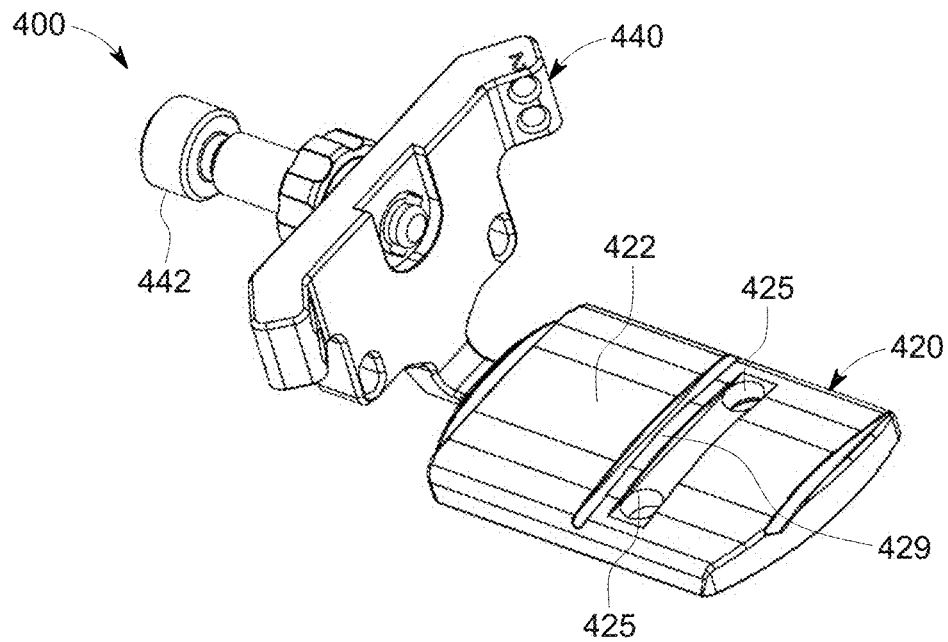
FIG. 20 is an enlarged top perspective view of the tibial implant trialing and cutting guide of FIG. 19, according to an embodiment of the present disclosure.
Figure 21:
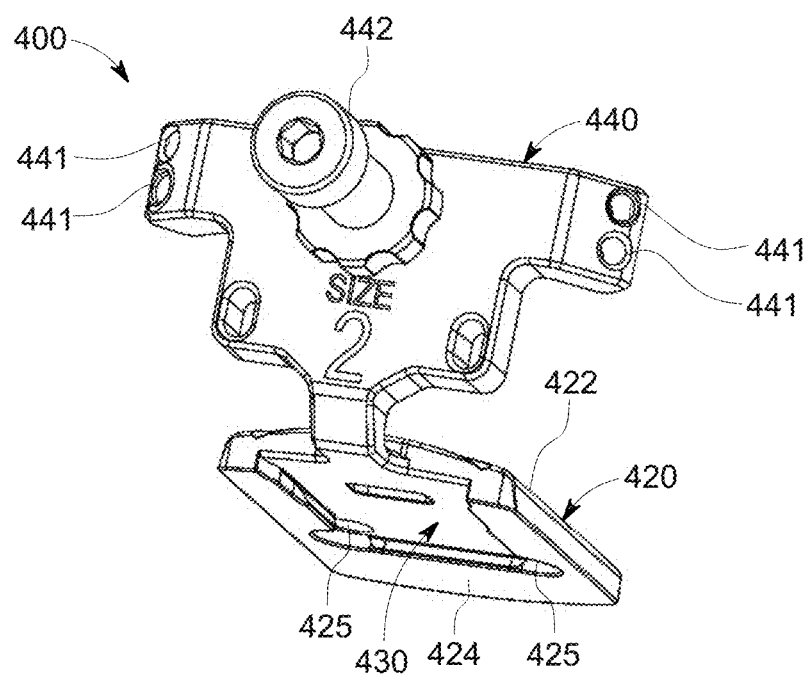
FIG. 21 is a bottom perspective view of the tibial implant trialing and cutting guide of FIG. 20, according to an embodiment of the present disclosure.

As shown in FIGS. 20 and 21, the tibial trialing component 400 may include a base portion 420 and an arm or wing portion 440. The proximal-distal thickness, the medial-lateral width, and/or the anterior-posterior size/dimension, shape and/or orientation of the base portion 420 of the tibial trialing component 400 may correspond (e.g., match or closely approximate) to that of the tibial implant component of the TAR prosthesis. The base portion 420 includes a proximal bone engagement surface or side 422 configured to engage/abut the distal tibia (potentially resected) of a patient. In some embodiments, the proximal bone engagement surface 422 of the base portion 420 is convex (e.g., arcuately convex) along the medial-lateral direction. In other embodiments (not shown), the proximal bone engagement surface 422 of the base portion 420 may be flat/planar along the medial-lateral direction.

The base portion 420 may include at least one through-hole or aperture 425 that extends through the base portion 420 from the proximal bone engagement surface 422 to a distal insert engagement surface or side 424 (FIG. 21). In some embodiments, the base portion 420 includes a plurality of through-holes 425 such as a pair of through holes. The at least one through-hole 425 is configured as a guide hole for a cutting instrument (e.g., as described below a detachable cutting and/or punch tool having cutting or punch pins, or a sharp tipped trocar, drill, etc.) to remove portions of the resected distal tibia to accommodate at least one peg of a corresponding tibial implant component therein. The illustrative embodiment, as shown in FIGS. 20 and 21, includes two through holes 425 having a medial through-hole 425 and a lateral through-hole 425. An adjustment screw 442 threadably extends through arm or wing portion 440 along the anterior-posterior direction. The anterior-posterior position/location of the adjustment screw 442 relative to the arm portion 440 may be adjusted with the posterior tip of the adjustment screw 442 contacting the anterior face of the tibia 10 (FIG. 19) proximal to the resected portion thereof (e.g., the anterior crown of the tibia 10).

Figure 22:
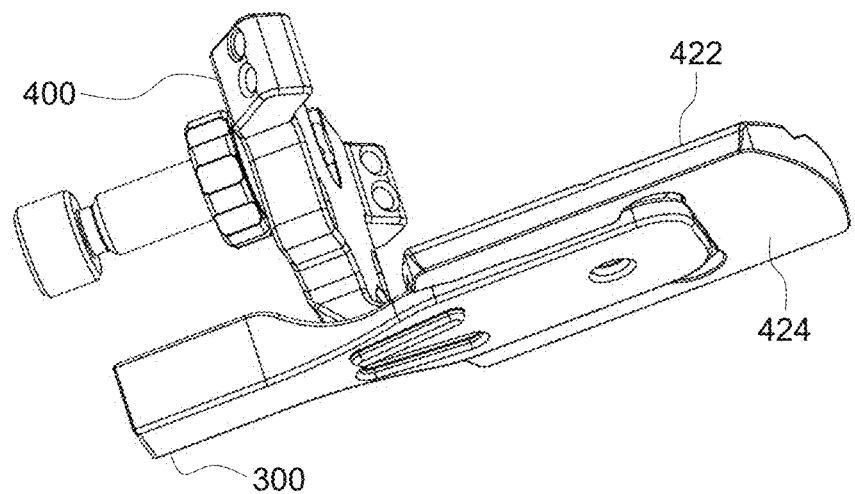
FIG. 22 is a bottom perspective view of the tibial implant trialing and cutting guide of FIG. 20 and the detachable paddle, according to an embodiment of the present disclosure.

The distal side 424 (FIG. 21) of the base portion 420 includes a distal recessed portion 430. The recessed portion 430 of the distal side 424 engages with the detachable paddle 300, for example, as shown in FIG. 22. With reference again to FIG. 21, the sides of the recessed portion 430 may include an undercut or otherwise be angled toward (or away) the periphery of the base portion 420 as they extend proximally to a planar proximal end surface to form a sliding dovetail socket or female portion for receiving a corresponding portion of a trial insert (not shown).

Figure 23:
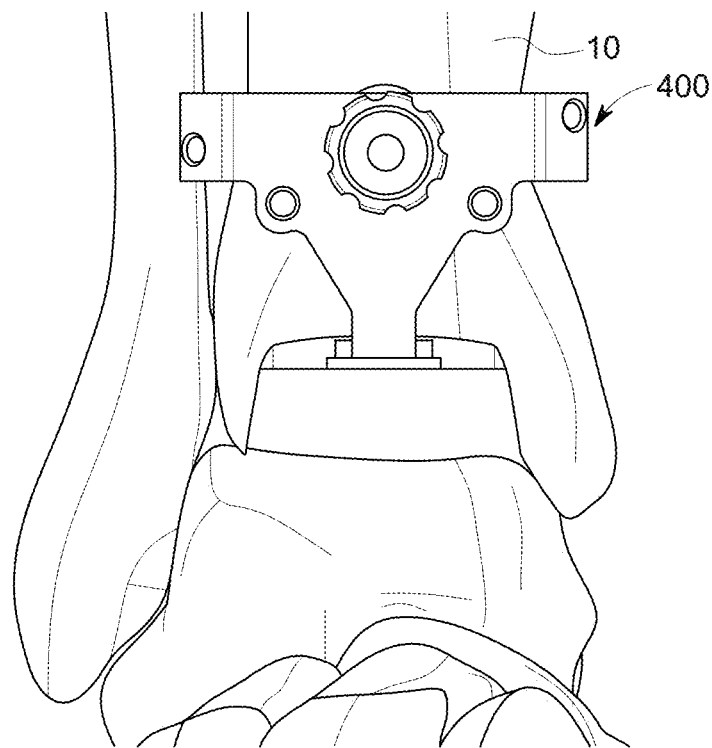
FIG. 23 is a front elevational view of the tibial implant trialing and cutting guide of FIG. 20 installed in a resected bone, according to an embodiment of the present disclosure.

With reference again to FIG. 19, the distractor system 100 with detachable flat paddles 300 is operable to seat tibial trialing component 400. Once the tibial trialing component 400 is seated, for example as shown in FIG. 23 (the distractor and the detachable paddles removed for clarity), pins (not shown) may be operably installed in the arm or wing portion 440 and attached to the patient's tibia 10, to secure the tibial trialing component 400 in place. The tibia trialing component 400 may be the same or similar to the tibia trialing components described in greater detail in U.S. provisional application No. 62/779,092, entitled "Instruments, Guides And Related Methods For Total Ankle Replacement", and International PCT Patent Application, filed Dec. 13, 2019, entitled "Instruments, Guides And Related Methods For Total Ankle Replacement", which are hereby incorporated by reference in their entirety herein.

Figure 24:
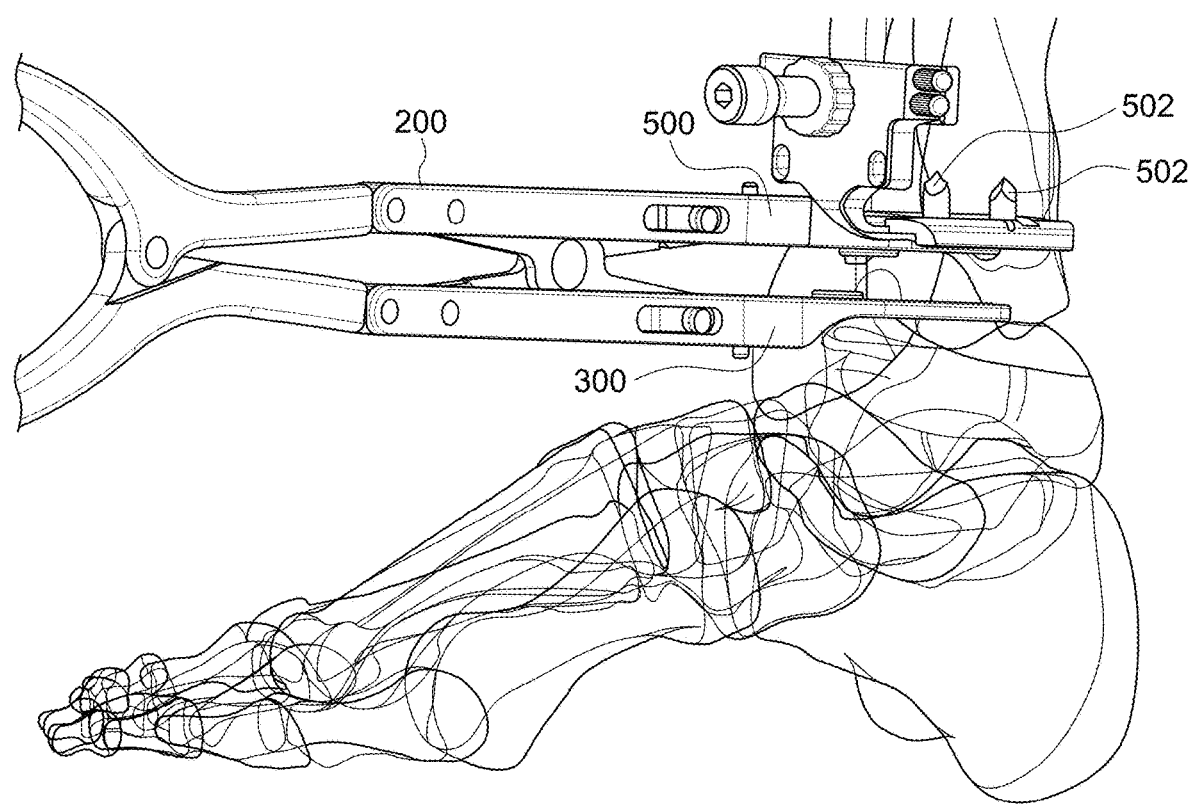
FIG. 24 is a perspective view of an tibial implant trialing and cutting guide, the distractor assembly with a detachable cutting and/or punch tool, according to an embodiment of the present disclosure.

With reference to FIG. 24, the distractor 100 and the detachable paddle 300 and a detachable peg punch paddle 500 may be employed for preparation of the resected tibia for the tibial implant component pins. For example, as described below, the detachable peg punch paddle 500 may include a punch pins 502 extendable in the cutting through-holes 425 (FIG. 20) of the tibial trialing component 400.

FIGS. 25-32 illustrate the detachable peg punch paddle 500, according to an embodiment of the present disclosure. In this illustrated embodiment, the detachable peg punch paddle 500 is essentially the same as paddle 300 (FIGS. 11 and 12) with the exception of the addition of the punch pins 502.

Figure 25:
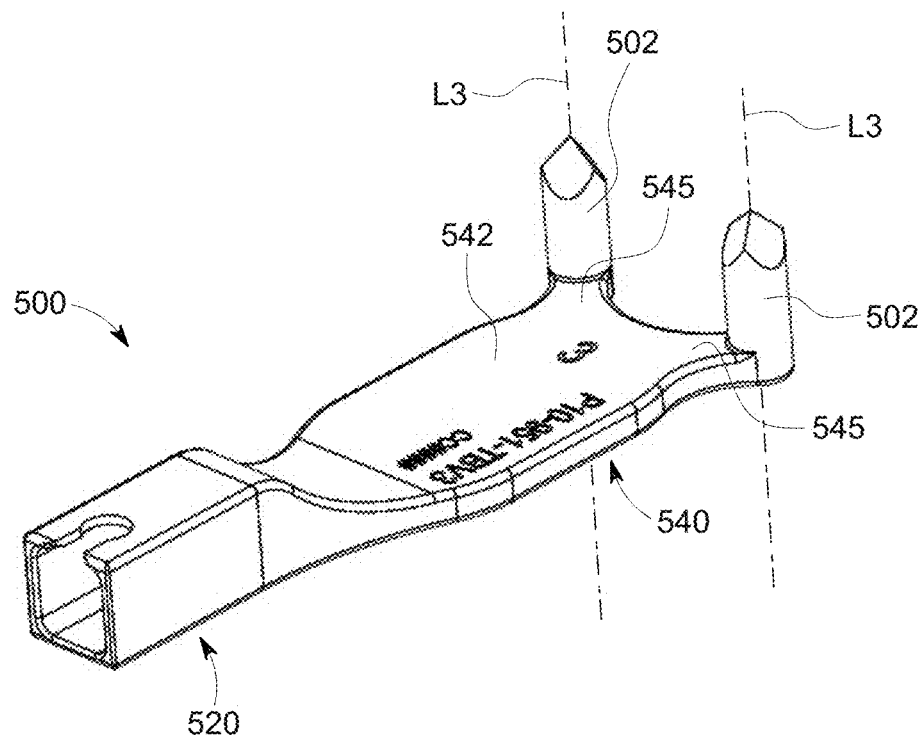
FIG. 25 is an enlarged top perspective view of the detachable cutting and/or punch tool of FIG. 24, according to an embodiment of the present disclosure.
Figure 26:
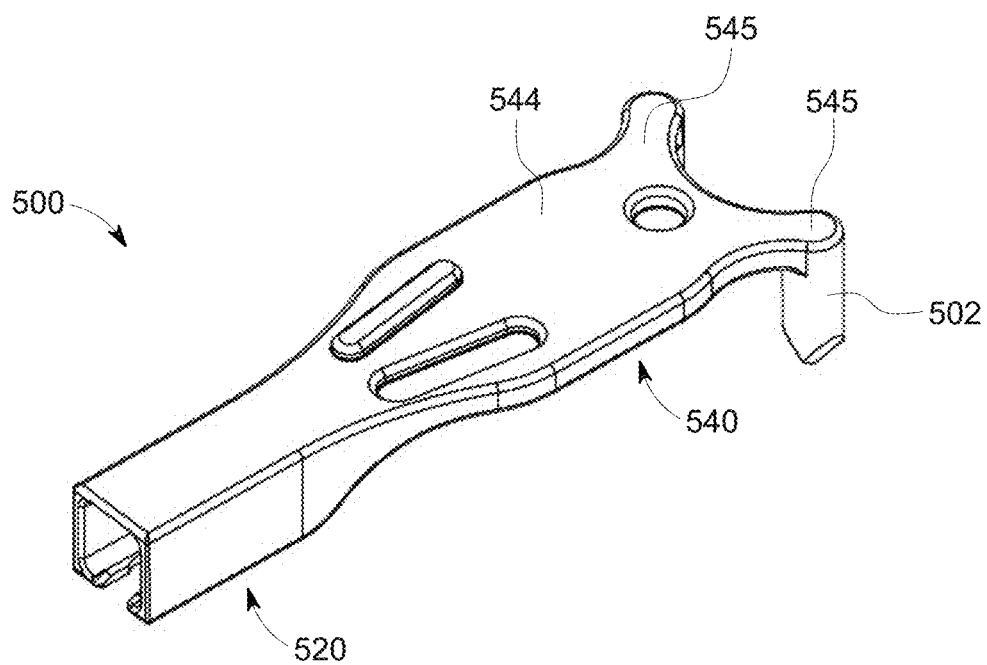
FIG. 26 is a bottom perspective view of the detachable cutting and/or punch tool of FIG. 25, according to an embodiment of the present disclosure.
Figure 27:
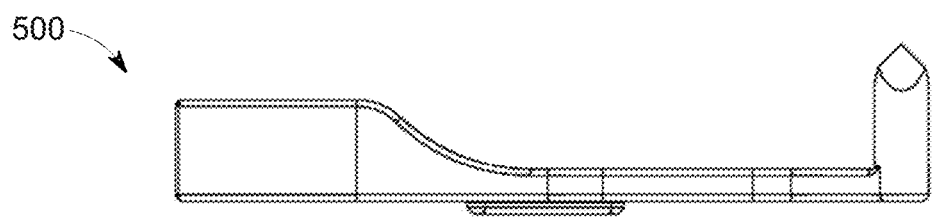
FIG. 27 is a front elevational view of the detachable cutting and/or punch tool of FIG. 25, according to an embodiment of the present disclosure.
Figure 28:
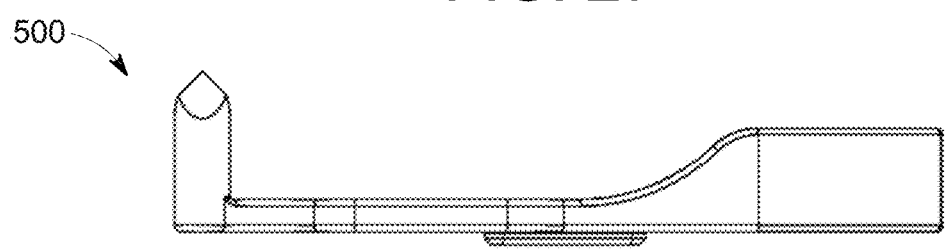
FIG. 28 is a rear elevational view of the detachable cutting and/or punch tool of FIG. 25, according to an embodiment of the present disclosure.
Figure 29:
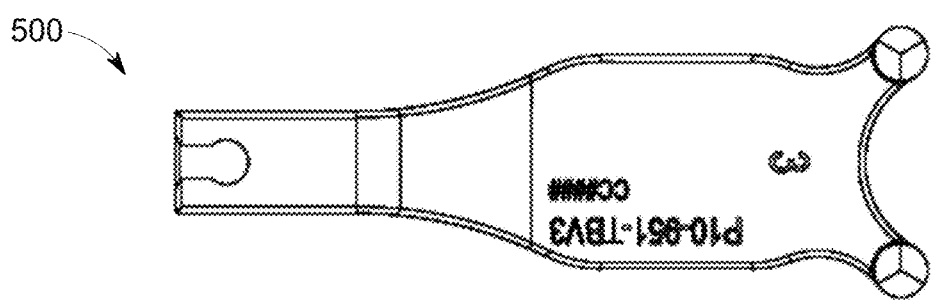
FIG. 29 is a top view of the detachable cutting and/or punch tool of FIG. 25, according to an embodiment of the present disclosure.
Figure 30:
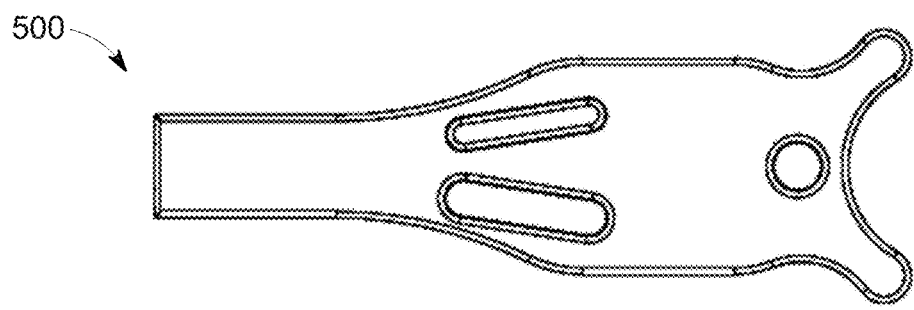
FIG. 30 is a bottom view of the detachable cutting and/or punch tool of FIG. 25, according to an embodiment of the present disclosure.
Figure 31:
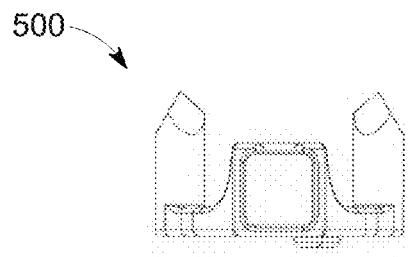
FIG. 31 is left side elevational view of the detachable cutting and/or punch tool of FIG. 25, according to an embodiment of the present disclosure.
Figure 32:
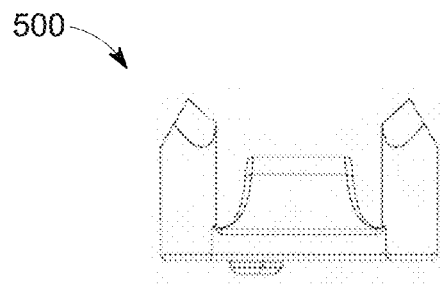
FIG. 32 is right side elevational view of the detachable cutting and/or punch tool of FIG. 25, according to an embodiment of the present disclosure.

With reference to FIGS. 25 and 26, the detachable peg punch paddle 500 may include a proximal portion 520 that operably releasably attaches to the first post 293 (FIG. 10) of first connector member 230 (FIG. 10) of the distractor 100 (FIG. 24). A distal portion 540 of the detachable peg punch paddle 500 may include a planar member having a first planar surface 542 and a second planar surface 544. Arms 545 may extend outwardly from the distal edge of the planar member and support the punch pins 502. For example, cutting and/or punch pins 502 may define a longitudinal axis L3 that are disposed normal or perpendicular to a longitudinal axis of the proximal portion and a longitudinal axis of the distal portion 540

Figure 33:
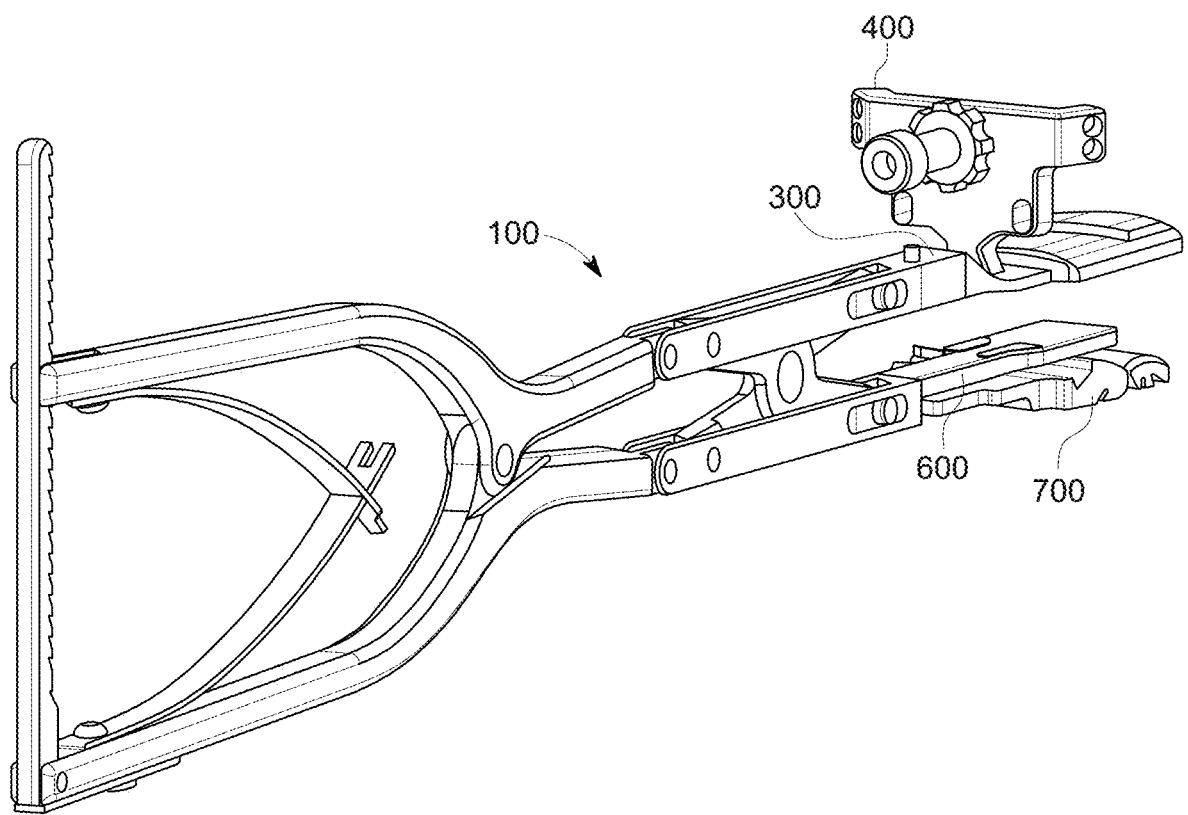
FIG. 33 is a perspective view of a detachable tibial implant trialing and cutting guide, distractor assembly with detachable paddles, and a detachable talar implant trialing and cutting guide, according to an embodiment of the present disclosure.
Figure 34:
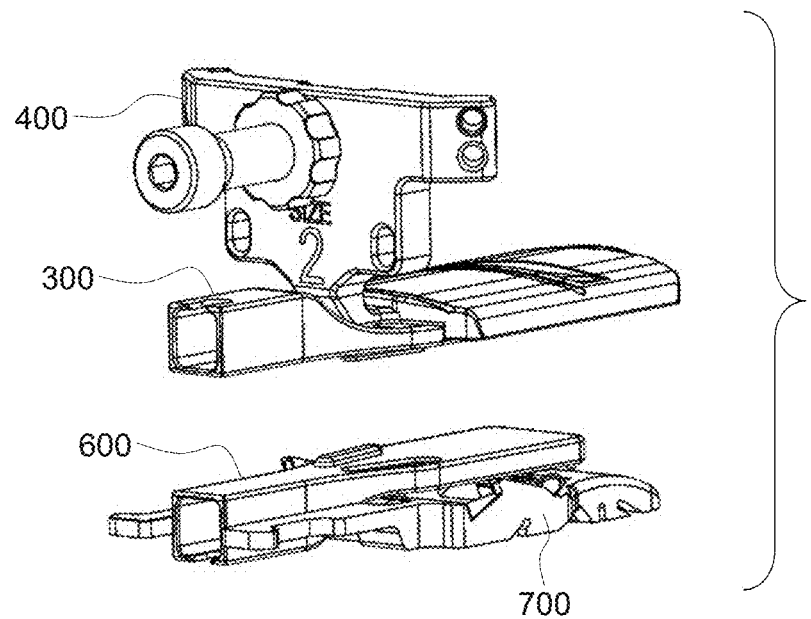
FIG. 34 is an enlarged, top perspective view of the detachable tibial implant trialing and cutting guide, the detachable paddles, and the detachable talar implant trialing and cutting guide of FIG. 33, according to an embodiment of the present disclosure.
Figure 35:
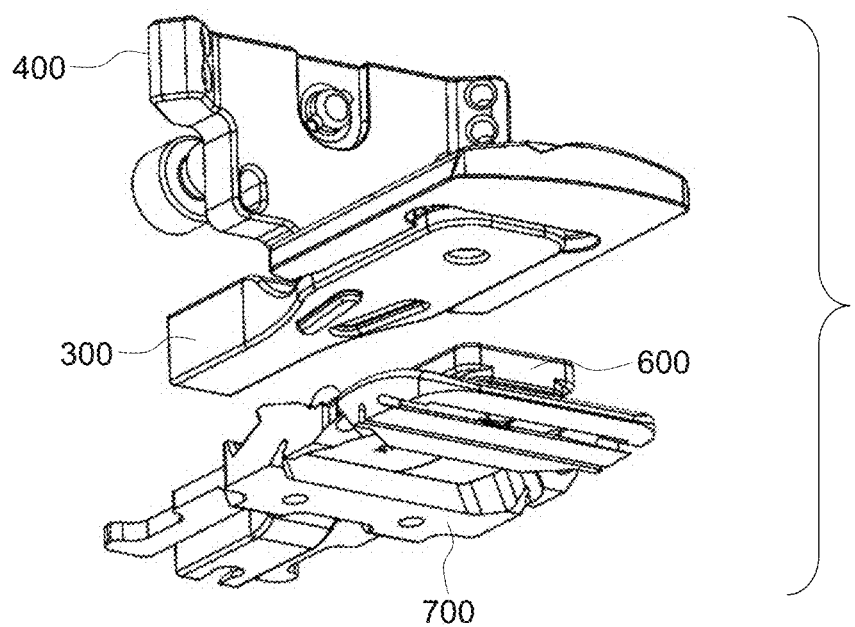
FIG. 35 is an enlarged, bottom perspective view of the detachable tibial implant trialing and cutting guide, the detachable paddles, and the detachable talar implant trialing and cutting guide of FIG. 33, according to an embodiment of the present disclosure.

FIG. 33 illustrates the distractor 100 operably connected to a stacked assembly of the tibial trialing component 400, the detachable paddle 300, a detachable paddle 600, and a talar trialing and cut guide 700, according to an embodiment of the present disclosure. FIGS. 34 and 35 further illustrate the stack of the tibial trialing component 400, the detachable paddle 300, the detachable paddle 600, and the talar trialing and cut guide 700.

The illustrated configuration, as shown in FIG. 33, allows distraction to fully seat the talar trialing component onto the dorsal cut of the talus. In addition, the illustrated configuration allows coupling and neutralizing the talar trial component relative to the tibial trial.

In this illustrated configuration as shown in FIG. 33, the talar trialing and cut guide 700 may correspond, in at least one aspect, to a talar implant component (not shown) of a TAR prosthesis (not shown). Based on the trialing of the tibial trialing component 400, and the talar trialing and cut guide 700, corresponding tibial implant component, talar implant component, and trialing insert may be selected based on the particular patient/ankle that best suits the patient/ankle. The tibial trialing component 400 and the talar trialing and cutting guide 700 may include a radio radiopaque material such that at least a portion of the components are visible under fluoroscopy or other imaging in situ.

Figure 36:
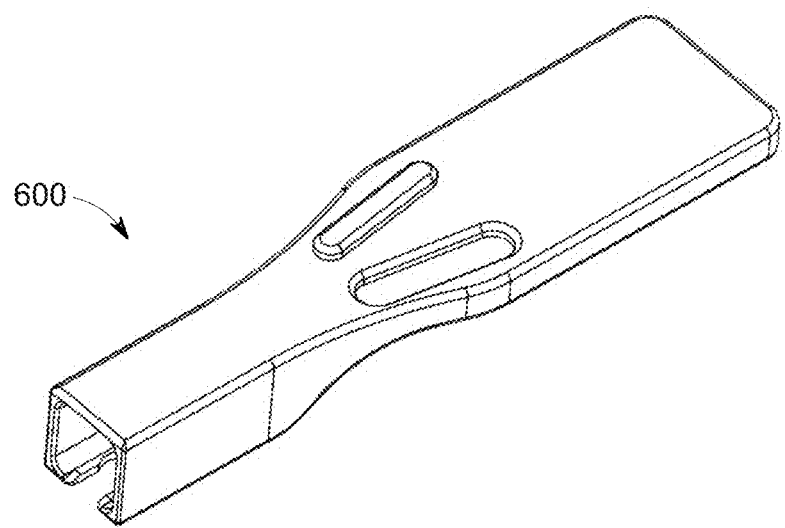
FIG. 36 is an enlarged, top perspective view of the detachable talar paddle of FIG. 33, according to an embodiment of the present disclosure.
Figure 37:
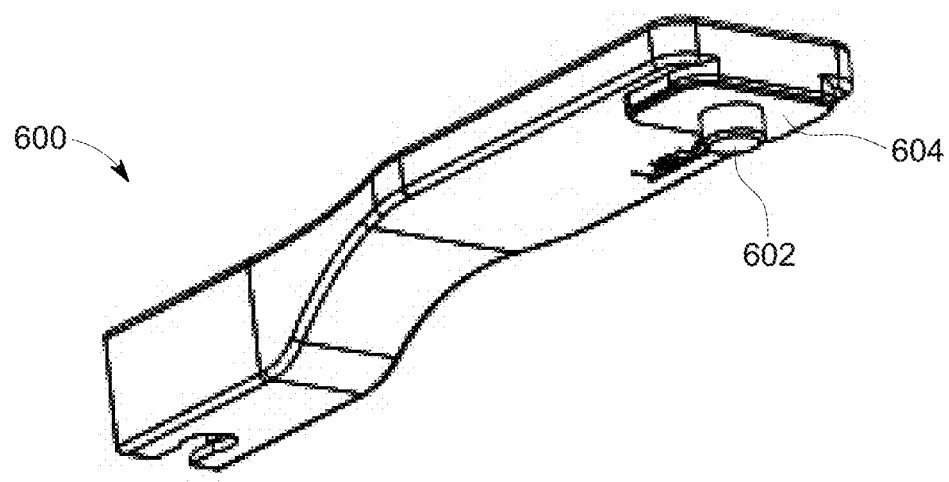
FIG. 37 is a bottom perspective view of the detachable talar paddle of FIG. 36, according to an embodiment of the present disclosure.

FIGS. 36 and 37 illustrate the detachable talar paddle 600, according to an embodiment of the present disclosure. In this illustrated embodiment, the detachable talar paddle 600 is essentially the same as the detachable paddle 300 with the exception of the addition of a pin 602 for coupling and engaging the talar trialing and cut guide 700. For example, the detachable talar paddle 600 may include a first side having the pin 602. The pin 602 may be positioned on a raised land 604.

Figure 38:
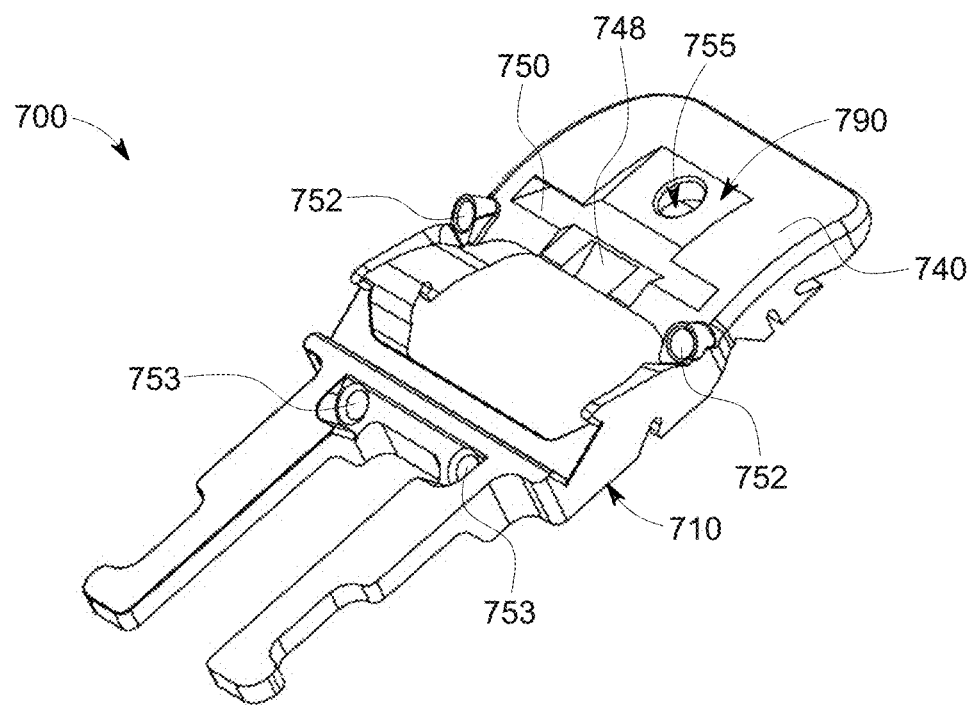
FIG. 38 is an enlarged, top perspective view of the talar implant trialing and cutting guide of FIG. 33, according to an embodiment of the present disclosure.
Figure 39:
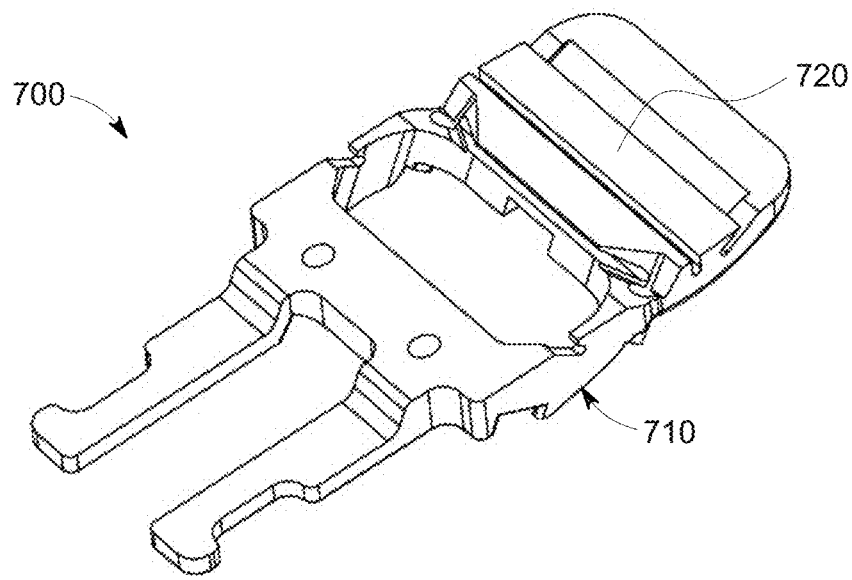
FIG. 39 is a bottom perspective view of the talar implant trialing and cutting guide of FIG. 38, according to an embodiment of the present disclosure.

FIGS. 38 and 39 illustrate the talar trialing and cut guide 700 for use with the detachable talar paddle 600 (FIG. 33) and distractor 100 (FIG. 33), according to an embodiment of the present disclosure. The talar trialing and cut guide 700 may include a body 710 having an inferior surface 720 (FIG. 39) engageable with a resected surface of the talus of the patient (not shown).

As best shown in FIG. 38, a superior surface 740 of the talar trialing cut guide 700 includes a recessed portion 790 having a recessed hole 755. The recess portion 790 is sized to receive the land 604 (FIG. 37) of the detachable paddle 600 (FIG. 37), and the recessed hole 750 is sized to receive pin 602 (FIG. 37) of detachable paddle 600 (FIG. 37). Other features of the talar trialing and cut guide 700 may include a strut slot 748, a cut slot 750, and pin apertures 752 and 753. The anterior portion of the strut slot 748 may be utilized by one or more cut guide to resect/chamfer anterior and/or posterior aspects of the talus. The cut slot 750 can be utilized as a cut guide for the removal of a posterior portion of the talus that extends (and therefore is angled) distally and posteriorly from the resected proximal surface of the talus. The pin apertures 752 and 753 may be configured to accept a pin, k-wire or other bone fixation member therethrough and into a talus. It will be appreciated that differently sized talar trialing and cut guides 700 may include differing anterior-posterior lengths, medial-lateral widths and/or proximal-distal thicknesses. The talar trialing and cut guide 700 may be the same or similar to the talar trial components described in greater detail in U.S. provisional application No. 62/779,092, entitled "Instruments, Guides And Related Methods For Total Ankle Replacement", and International PCT Patent Application, filed Dec. 13, 2019, entitled "Instruments, Guides And Related Methods For Total Ankle Replacement", which are hereby incorporated by reference in their entirety herein.

Figure 40:
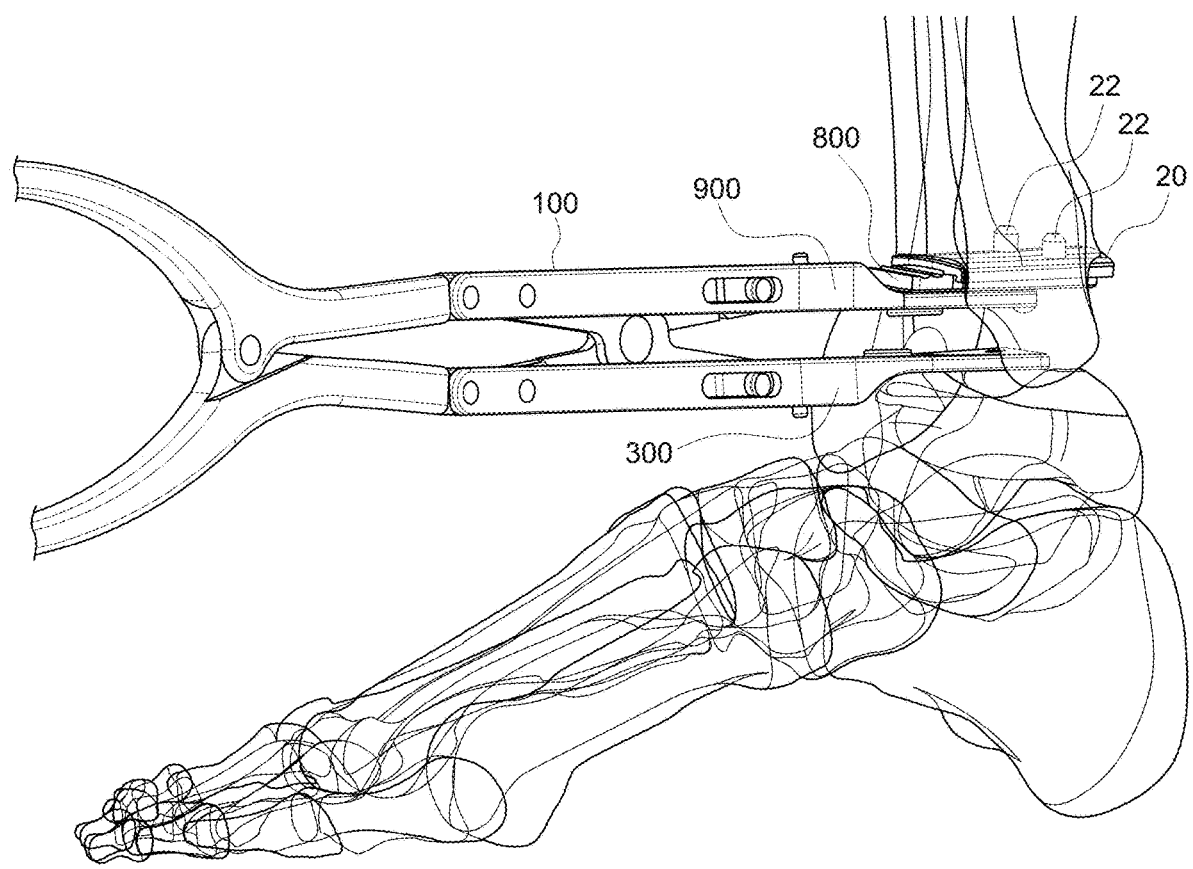
FIG. 40 is a perspective view of a tibial implant component and the distractor assembly with the detachable paddles and an impaction protection, according to an embodiment of the present disclosure.

FIG. 40 illustrates the distractor 200 along with a detachable paddle 900, the detachable paddle 300, and an impact protector 800 for use in installing a tibial implant 20, according to an embodiment of the present disclosure. As shown in FIG. 40, the tibial implant 20 includes posts 22 or other projections that are received in the recesses earlier formed in the resected tibia such as described above. The impact protector 800 is used to protect the tibial implant 20 while impacting. The impact protector 800 may be formed from a generally resilient material. For example, the impact protector 800 may be formed form a material that is more resilient than the tibial implant 20. The impact protector 800 may be formed from a material that is more resilient than the detachable paddle 900. In some embodiments, the impact protector 800 may be formed from an implant grade UHMWPE (ultra-high-molecular-weight polyethylene) material that is operable to protect the tibial implant 20 while impacting. It will be appreciated that other polymeric or like material may be suitably employed.

With reference to FIGS. 41-48, the implant protector 800 may include a body 810 having a proximal portion 820 and a distal portion 840, according to an embodiment of the present disclosure.

Figure 41:
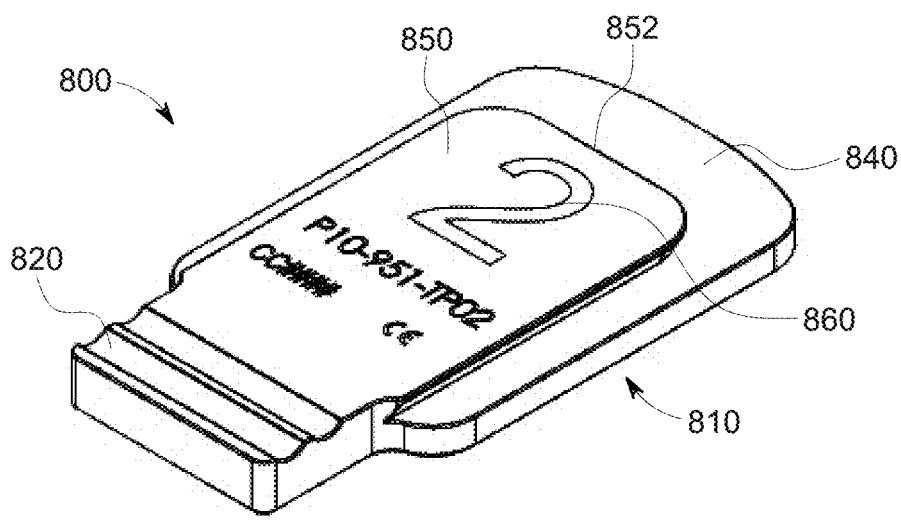
FIG. 41 is an enlarged top perspective view of the impaction protector of FIG. 40, according to an embodiment of the present disclosure.

As shown in FIG. 41, the distal portion 840 may be generally planar and include a projection or male portion 850 on the superior side. The raised projection 850 may be a male portion that is configured to mate and be received in a corresponding recessed portion (not shown) of the tibial implant component 20 (FIG. 40). For example, the sides of the projection 850 may include an undercut or otherwise be angled away (or toward) from the periphery of the implant protector 800 to form a sliding dovetail male portion which may engage the recessed portion of the tibial trial component 20 (e.g., a sliding dovetail socket/female portion). A distal edge 852 of projection 850 may allow for positioning of the impact protector 800 along the anterior-posterior direction relative to the tibial implant component. For example, the recess in the tibial implant may have a corresponding distal edge. In another embodiment, the projection may have flat sides, (e.g., sides that are normal or perpendicular to the superior planar surface of the impact protector). Indicia 860 such as a number may be provided on the impact protector to identify and correspond to the corresponding selected sized tibial implant component. The distal portion 820 may provide a handle or end engageable by a surgeon for releasably attaching the impact protector to the tibial implant.

Figure 42:
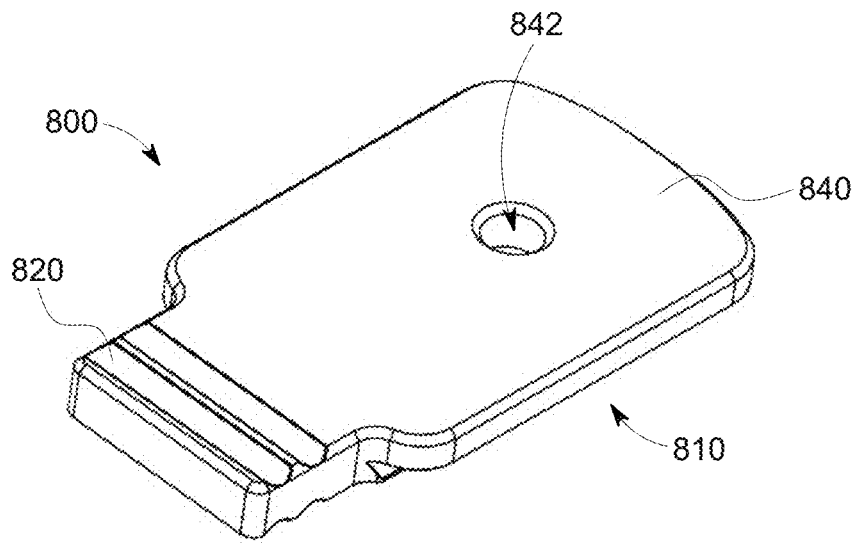
FIG. 42 is a bottom perspective view of the impaction protector of FIG. 41, according to an embodiment of the present disclosure.
Figure 43:
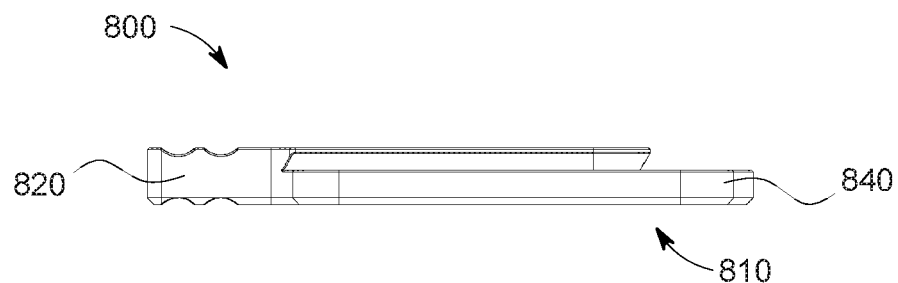
FIG. 43 is a front elevational view of the impaction protector of FIG. 41, according to an embodiment of the present disclosure.
Figure 44:
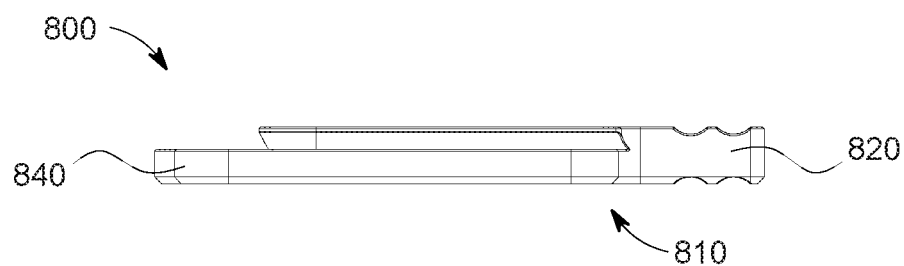
FIG. 44 is a rear elevational view of the impaction protector of FIG. 41, according to an embodiment of the present disclosure.
Figure 45:
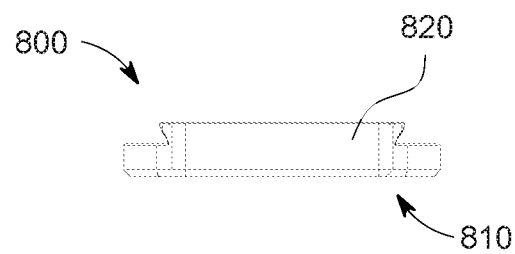
FIG. 45 is left side elevational view of the impaction protector of FIG. 41, according to an embodiment of the present disclosure.
Figure 46:
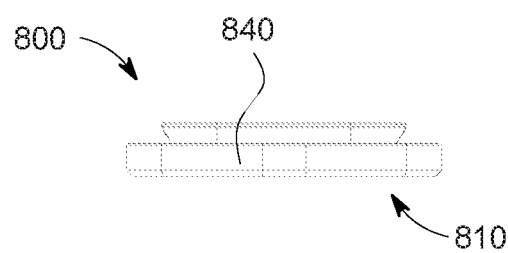
FIG. 46 is right side elevational view of the impaction protector of FIG. 41, according to an embodiment of the present disclosure.
Figure 47:
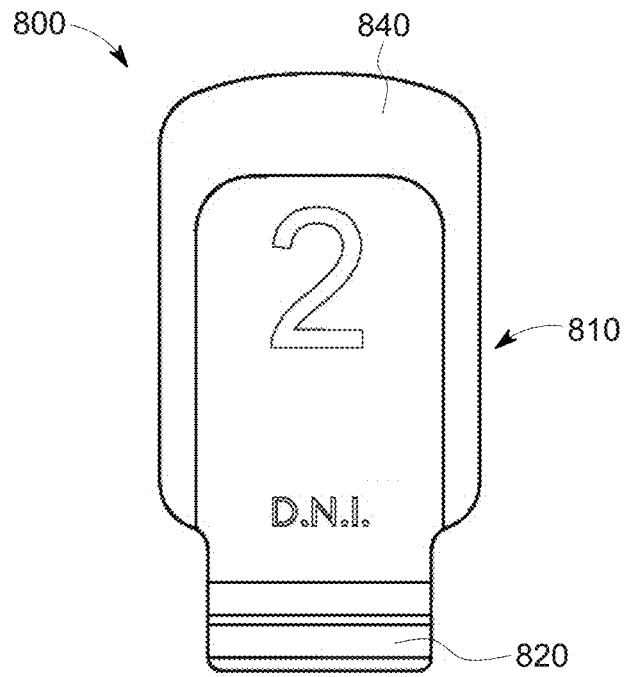
FIG. 47 is a top view of the impaction protector of FIG. 41, according to an embodiment of the present disclosure.
Figure 48:
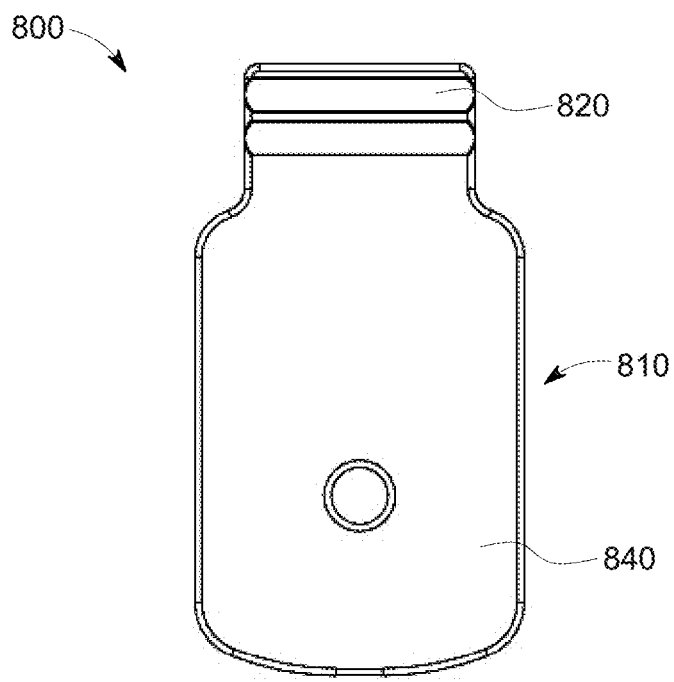
FIG. 48 is a bottom view of the impaction protector of FIG. 41, according to an embodiment of the present disclosure.
Figure 49:
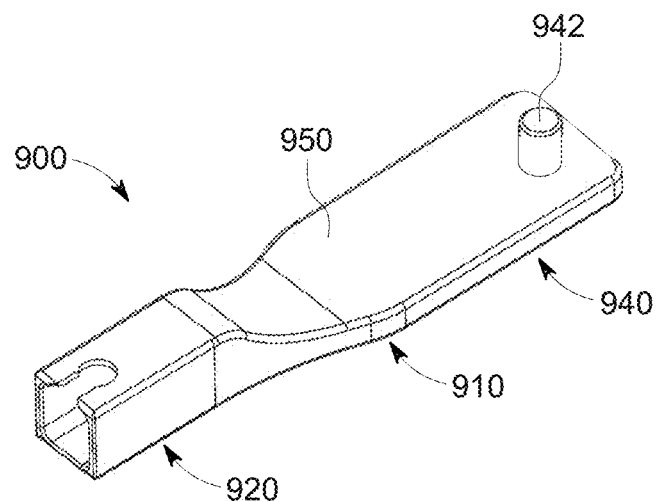
FIG. 49 is an enlarged top perspective view of the detachable tibial paddle of FIG. 40, according to an embodiment of the present disclosure.
Figure 50:
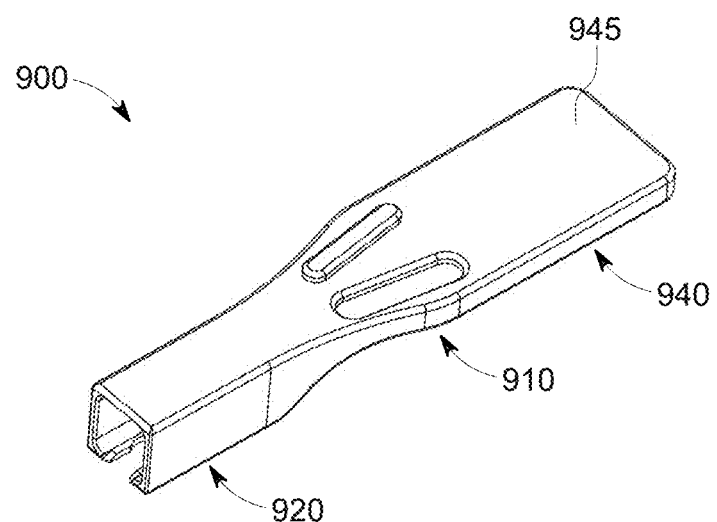
FIG. 50 is a bottom perspective view of the detachable tibial paddle of FIG. 49, according to an embodiment of the present disclosure.

FIGS. 49 and 50 illustrate the detachable paddle 900 for use with the distractor 100 (FIG. 39) for installing the tibial component 20, according to an embodiment of the present disclosure. The detachable paddle 900 may include a body 910 defining a proximal portion 920 and a distal portion 944. The proximal end 920 may be operably releasably attachable to the distractor 100 (FIG. 39) as described above. The distal portion 940 may include a generally planar member having a superior surface 950 (FIG. 49) and an inferior surface 945 (FIG. 50). With reference to FIG. 42, the distal portion 840 of the impaction protector 800 may include a recessed hole or cavity 842 for receipt of a corresponding projection 942 (FIG. 49) on the superior surface 950 (FIG. 49) of the detachable paddle 900 (FIG. 49). The detachable paddle 900 may be usable with various sized and configured impact protectors.

Figure 51:
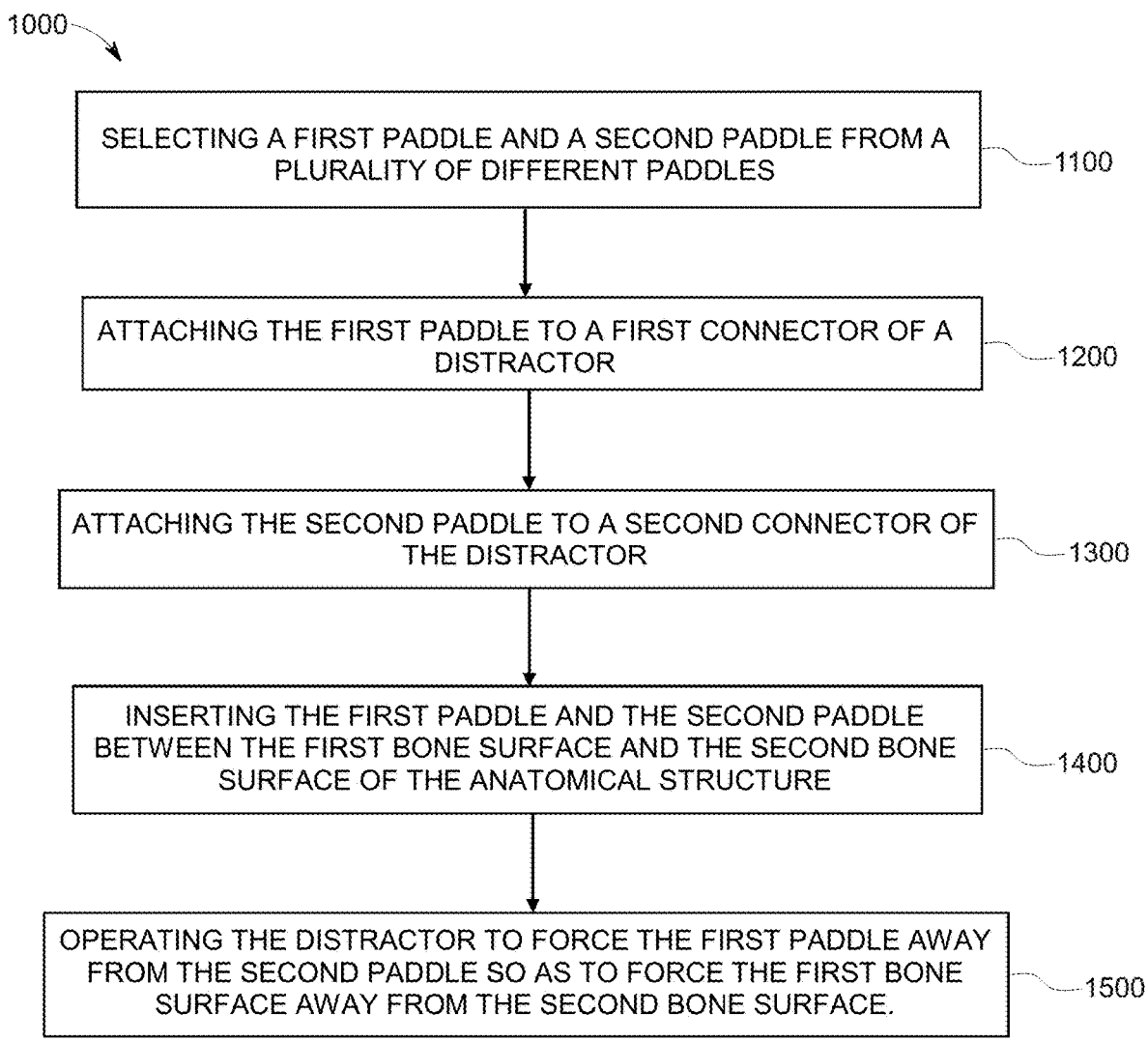
FIG. 51 is a flowchart of a surgical method, according to an embodiment of the present disclosure.

FIG. 51 illustrates a surgical method 1000 for separating a first bone surface from a second bone surface of an anatomical structure, according to an embodiment of the present disclosure. For example, method 1000 may include at 1100 selecting a first paddle and a second paddle from a plurality of different paddles, at 1200 attaching the first paddle to a first connector of a distractor, at 1300 attaching the second paddle to a second connector of the distractor, at 1400 inserting the first paddle and the second paddle between the first bone surface and the second bone surface of the anatomical structure, and at 1500 operating the distractor to force the first paddle away from the second paddle so as to force the first bone surface away from the second bone surface.

Figure 52:
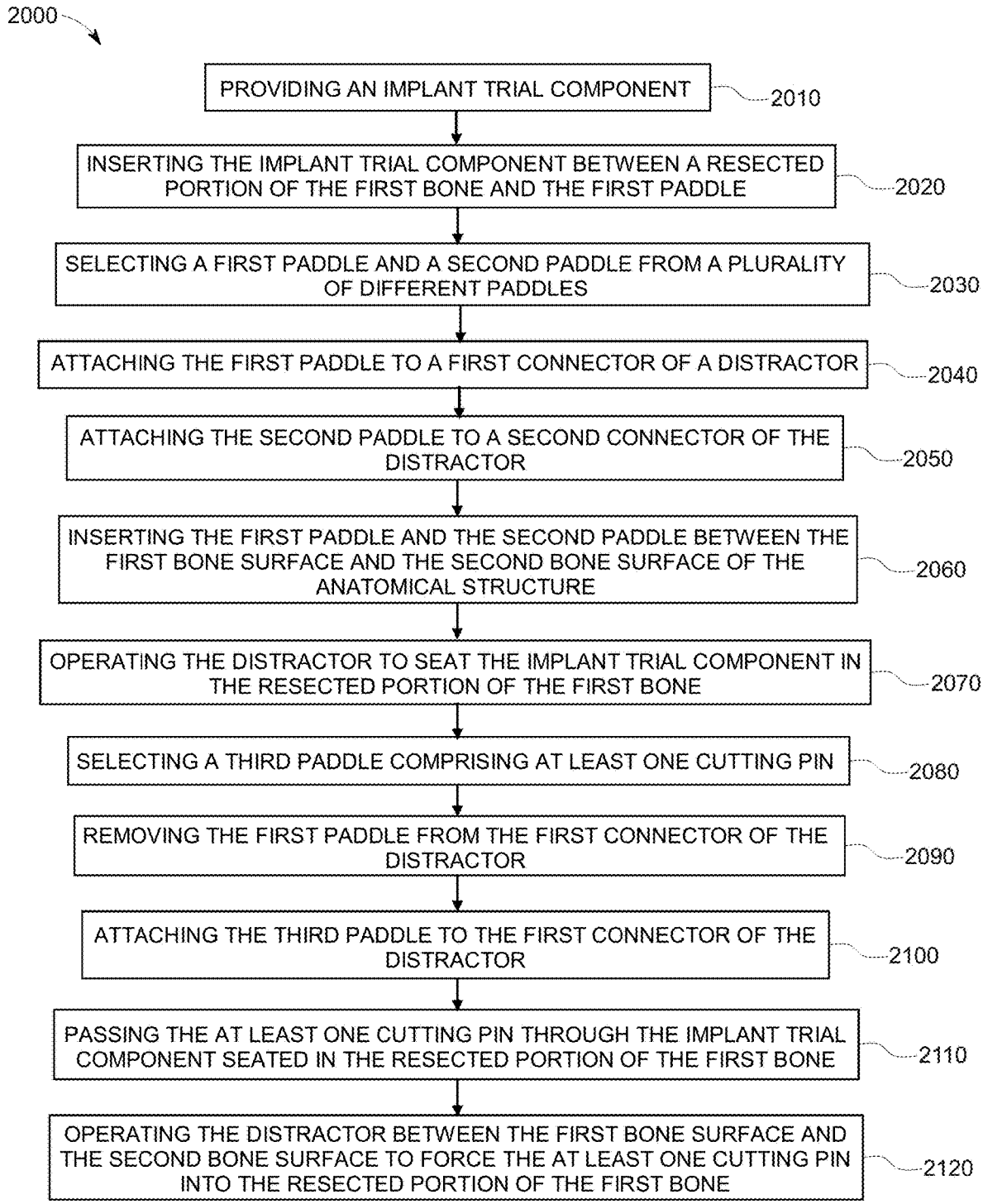
FIG. 52 is a flowchart of a surgical method, according to an embodiment of the present disclosure.

FIG. 52 illustrates a surgical method 2000 for installing an implant in an anatomical structure, according to an embodiment of the present disclosure. The method 2000 may include at 2010 providing an implant trialing and cutting guide, at 2020 inserting the implant trialing and cutting guide between a resected portion of the first bone and the first paddle, at 2030 selecting a first detachable paddle and a detachable second paddle from a plurality of different paddles, at 2040 attaching the first paddle to a first connector of a distractor, at 2050 attaching the second paddle to a second connector of the distractor, at 2060 inserting the first paddle and the second paddle between the first bone surface and the second bone surface of the anatomical structure, and at 2070 operating the distractor to seat the implant trialing and cutting guide in the resected portion of the first bone.

The method may further include at 2080, selecting a third detachable paddle having at least one punch pin, at 2090 removing the first detachable paddle from the first connector of the distractor, at 2100 attaching the third detachable paddle to the first connector of the distractor, at 2110 passing the at least one punch pin through the implant trial component seated in the resected portion of the first bone, and at 2120 using the distractor to force the at least one cutting and/or punch pin into the resected portion of the first bone.

Figure 53:
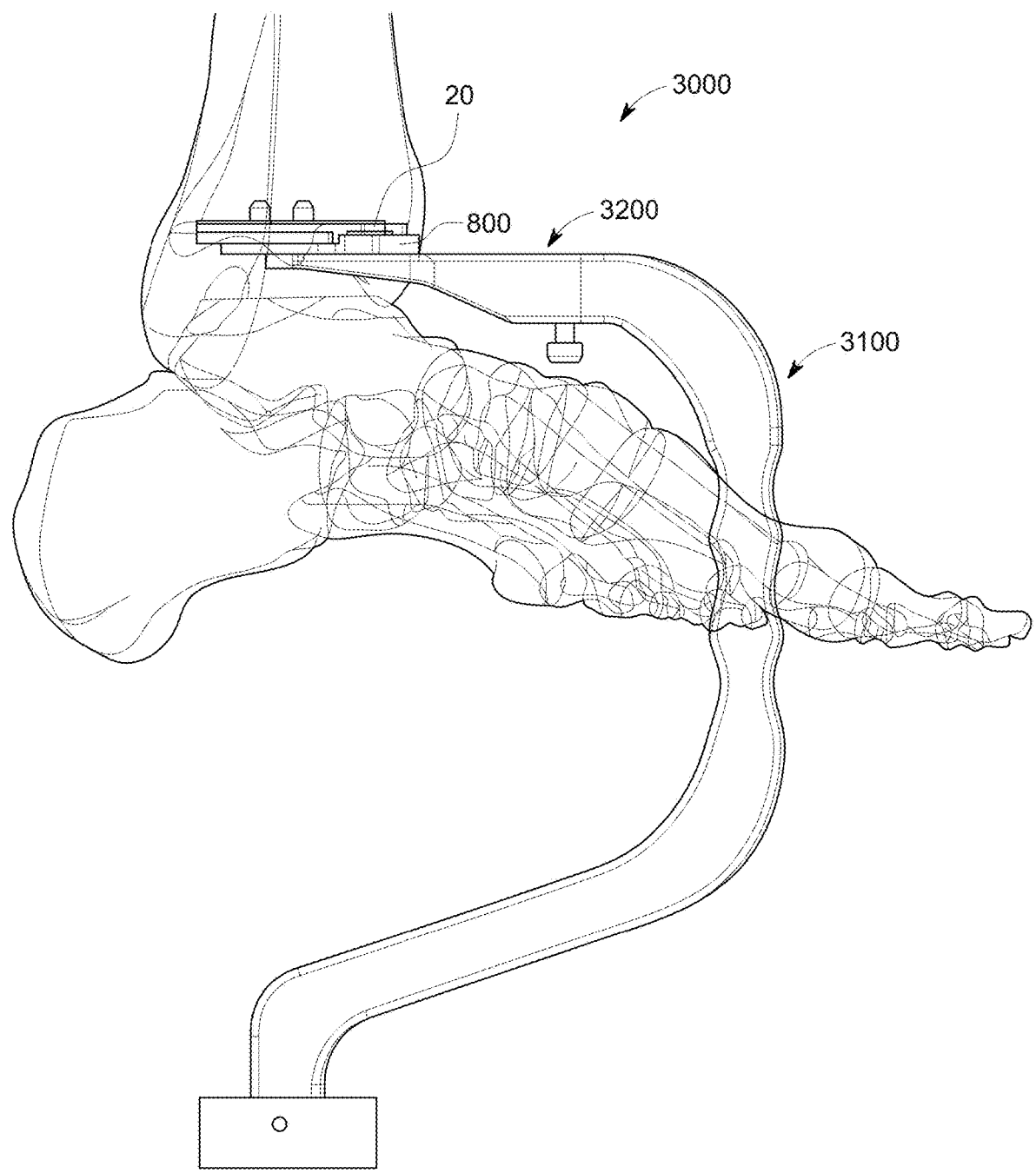
FIG. 53 is a perspective view of an impaction system, tibial implant component, and a detachable impaction projector, according to an embodiment of the present disclosure.
Figure 54:
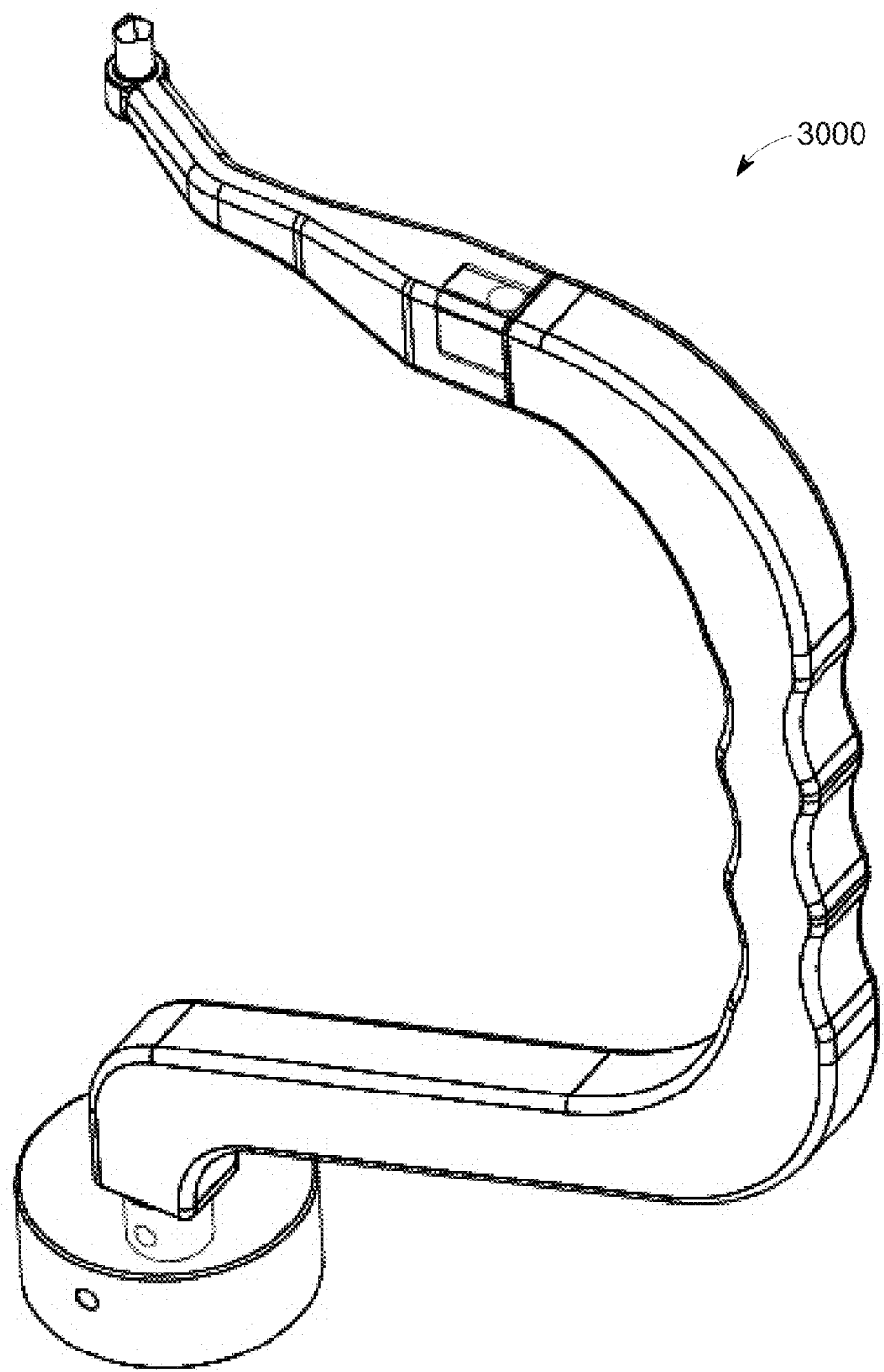
FIG. 54 is a perspective view of the impaction system of FIG. 53, according to an embodiment of the present disclosure.

FIGS. 53 and 54 illustrate an implant impaction system 3000 for use in installing the tibial implant component 20 (FIG. 53), according to an embodiment of the present disclosure. For example, the implant impaction system 3000 may be a tibial implant impaction system for use in installing a tibial implant component in a TAR. In this illustrated embodiment, as shown in FIGS. 55-61, the implant impaction system 3000 may include a body 3100, a detachable projecting member 3200, and the impaction protector 800 (FIG. 53).

Figure 55:
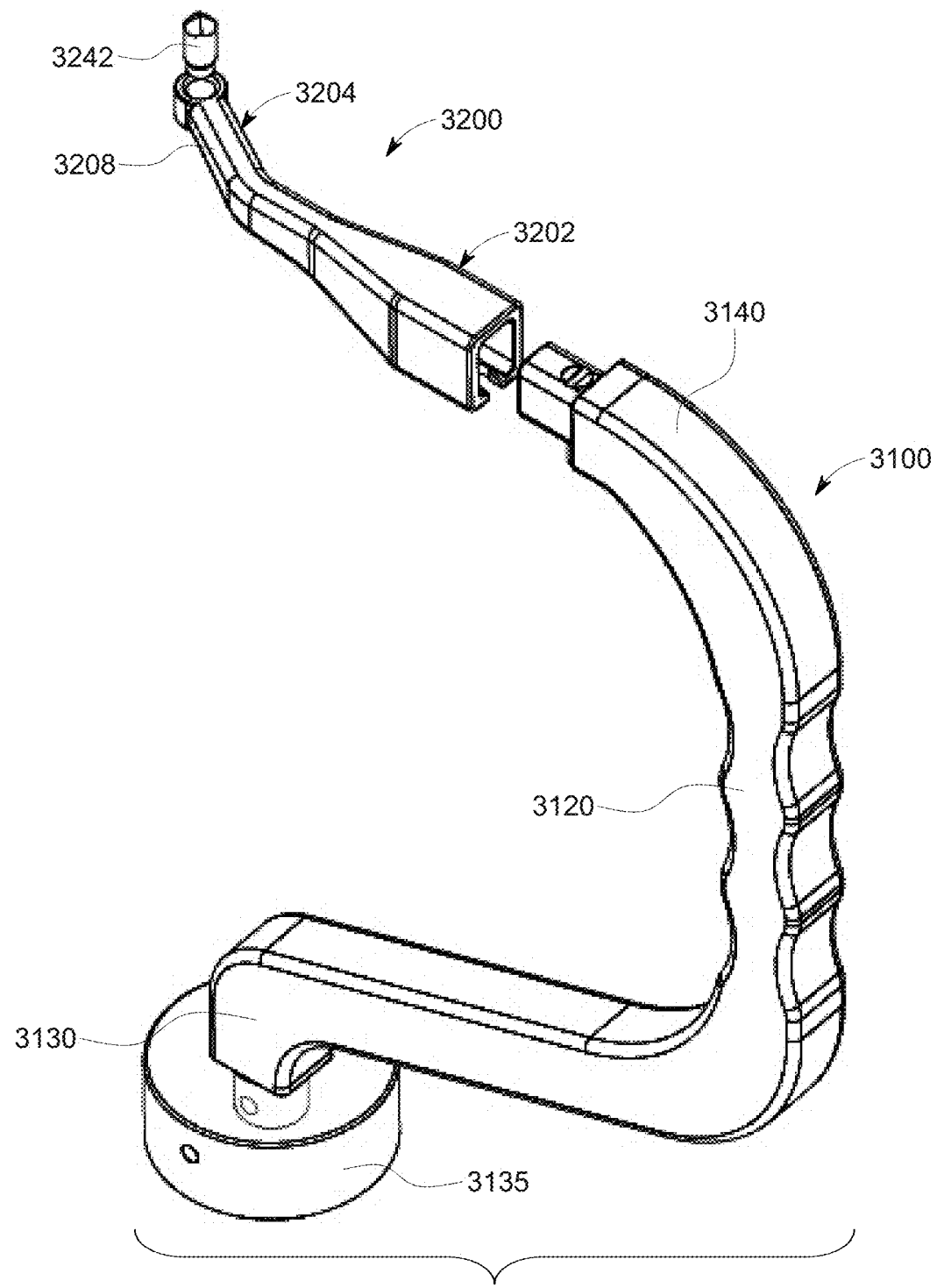
FIG. 55 is an exploded perspective view of the impaction system of FIG. 54, according to an embodiment of the present disclosure.
Figure 56:
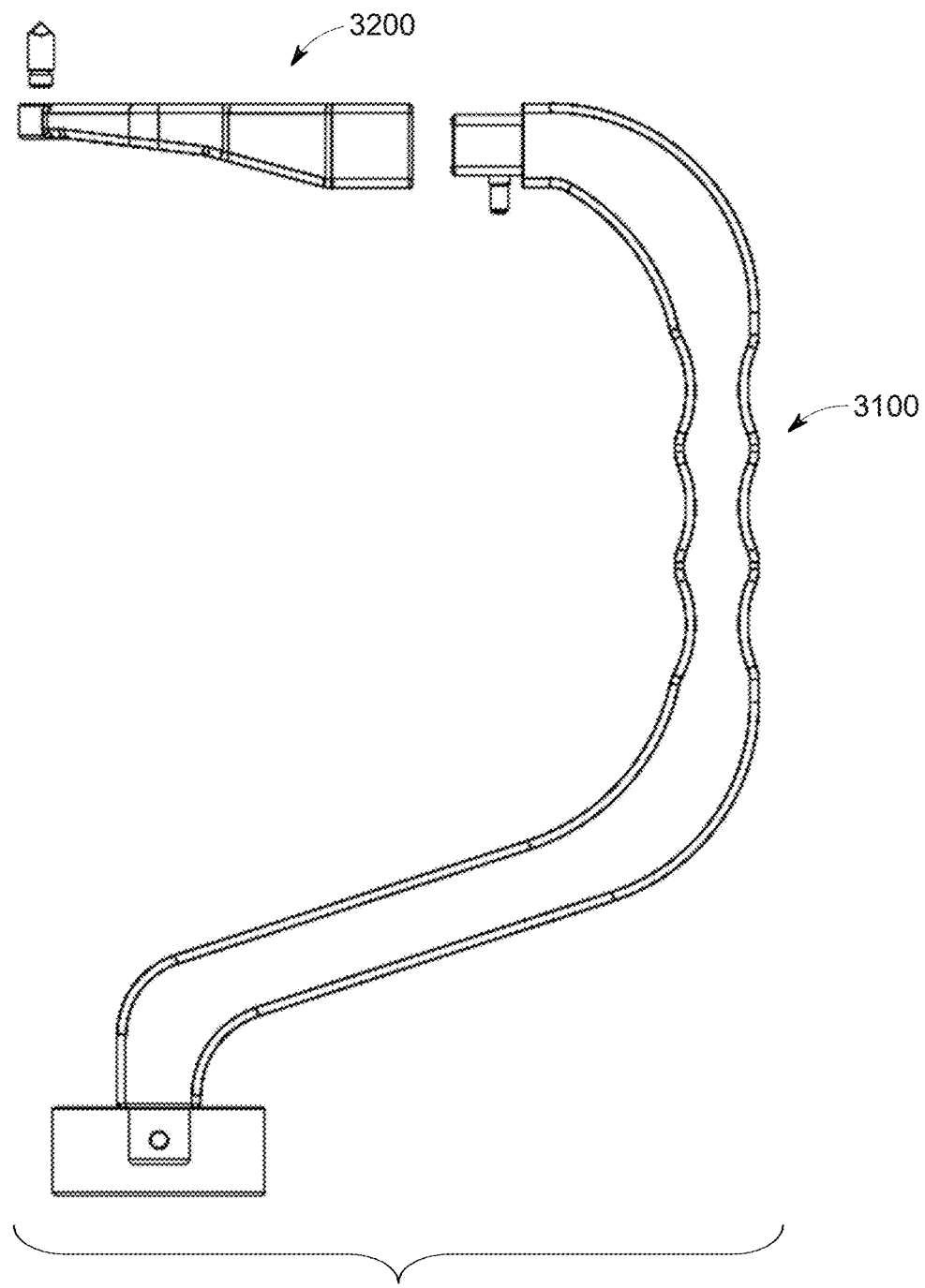
FIG. 56 is an exploded front elevational view of the impaction system of FIG. 54, according to an embodiment of the present disclosure.
Figure 57:
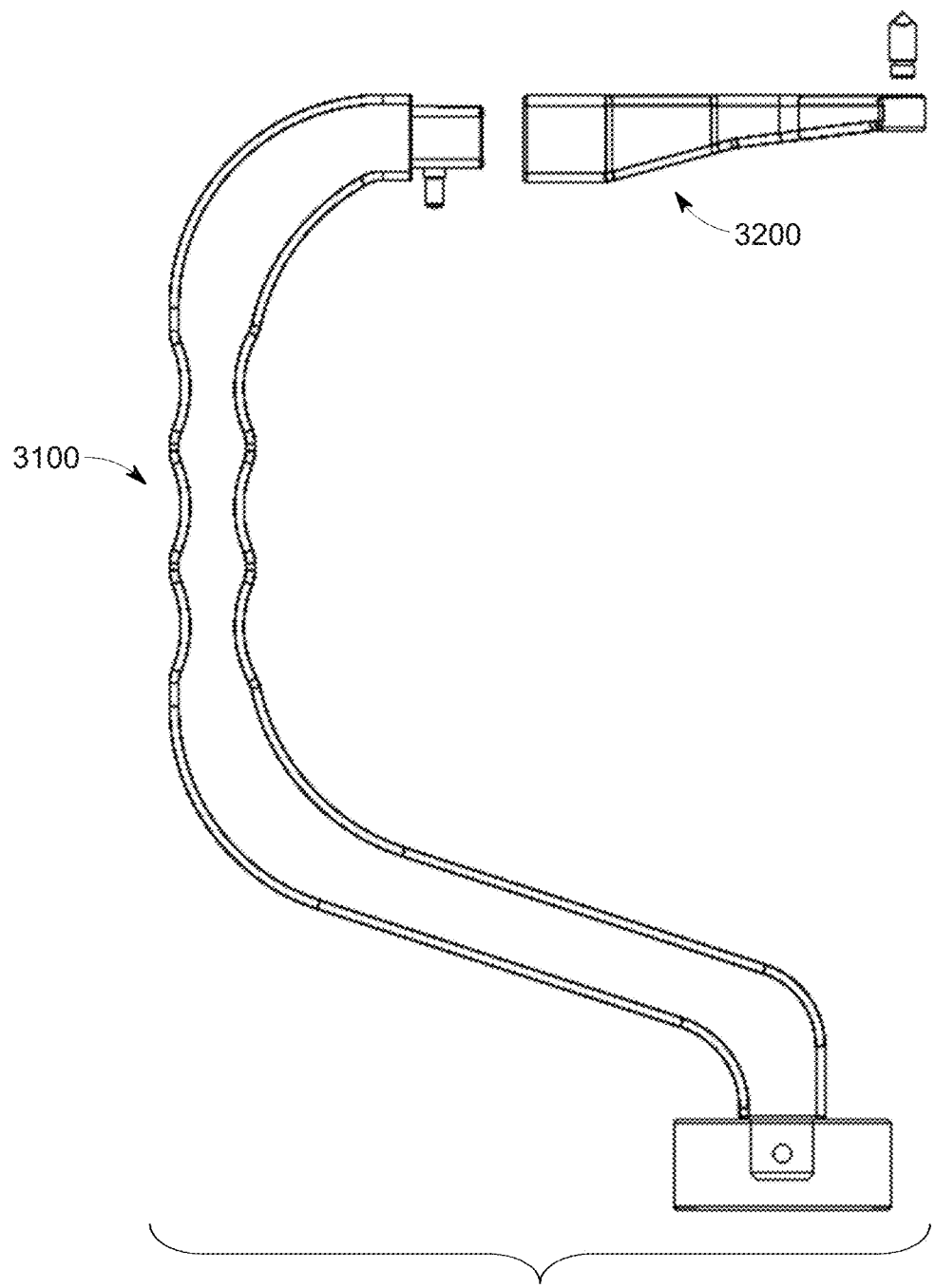
FIG. 57 is an exploded rear elevational view of the impaction system of FIG. 54, according to an embodiment of the present disclosure.
Figure 60:
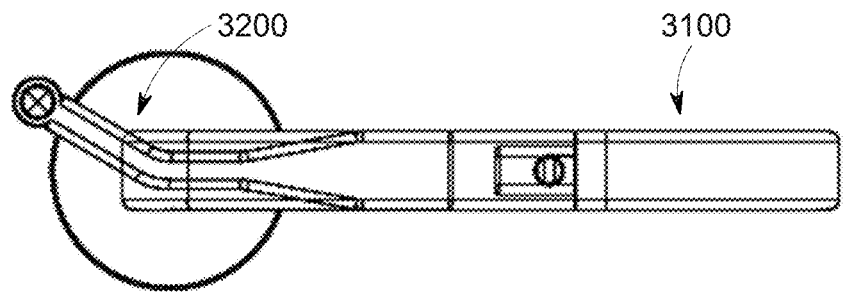
FIG. 60 is a top view of the impaction system of FIG. 54, according to an embodiment of the present disclosure.
Figure 61:
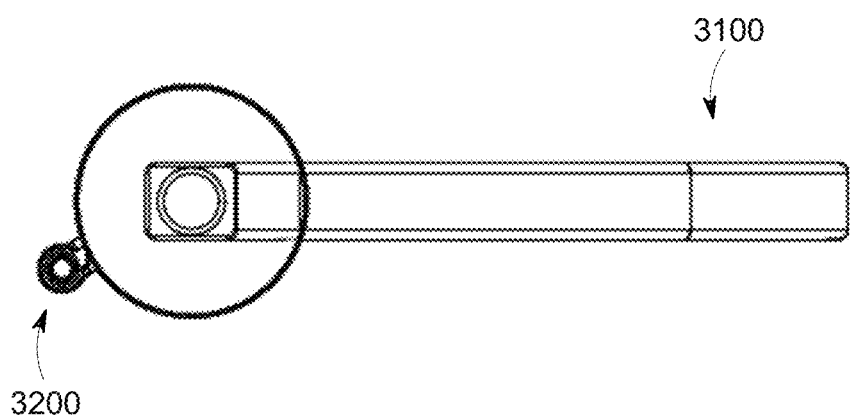
FIG. 61 is a bottom view of the impaction system of FIG. 54, according to an embodiment of the present disclosure.

With reference to FIG. 55, the body 3100 may have a generally U-shaped configuration defining a central or middle handle portion 3120, an impact portion 3130, and a distal portion 3140 operable for releasably connecting to the projecting member 3200. The detachable projecting member 3200 may have a proximal portion 3202 and a distal portion 3204. The proximal portion 3202 may be releasably attachable to the distal portion 3140 of the body 3100. In some embodiments, the U-shaped configuration of the body may be disposed along a plane, and when the detachable projected member 3200 is attached to the distal portion 3140 of the body 3100, a distal end 3208 of the projection member 3204 is offset from the plane as best shown in FIG. 60.

With reference again to FIG. 53, the impaction protector 800 is supportable on the distal portion 3204 of the detachable projecting member 3200. The impaction protector 800 is positionable between the tibial implant component 20 and the detachable projecting member 3200 during implanting of the tibial implant component 20. The impaction protector 800 is further shown in FIGS. 41-48 and described above.

With reference again to FIG. 55, the distal portion 3204 of the detachable projecting member 3200 may include a pin 3242 which is receivable in the cavity 842 (FIG. 42) of the impaction protector 800 (FIG. 42). The proximal portion 3130 may include an enlarged knob 3135. The implant impaction system 3000 may be used with traditional impaction instruments such as a hammer. The implant impactor system 3000 may include a plurality of differently sized and configured impaction protectors, each of which being supportable on the distal portion of the projecting member.

FIGS. 62-69 illustrate a detachable tibial paddle 4300, according to an embodiment of the present disclosure. In this exemplary embodiment, the detachable tibial trial paddle 4300 may be a universally sized detachable tibial paddle with an anti-rotation feature operable to nest inside or mate with a dovetail of a tibial trialing implant component (not shown).

Figure 62:
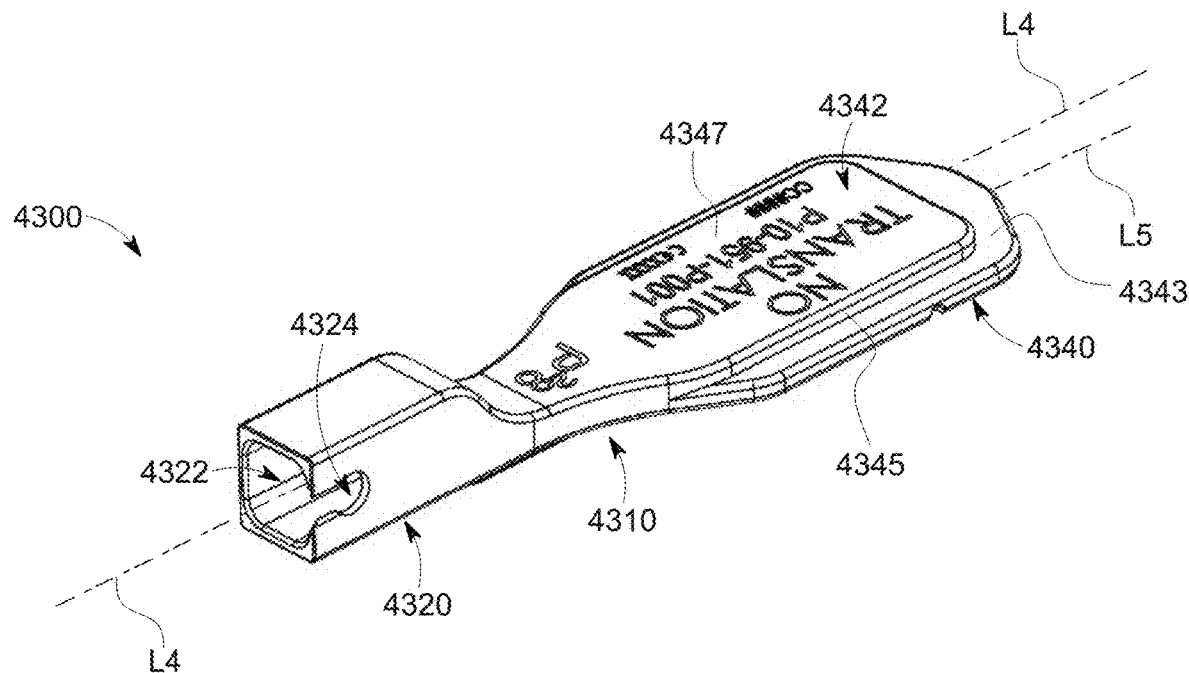
FIG. 62 is a top perspective view of a detachable paddle, according to an embodiment of the present disclosure.
Figure 63:
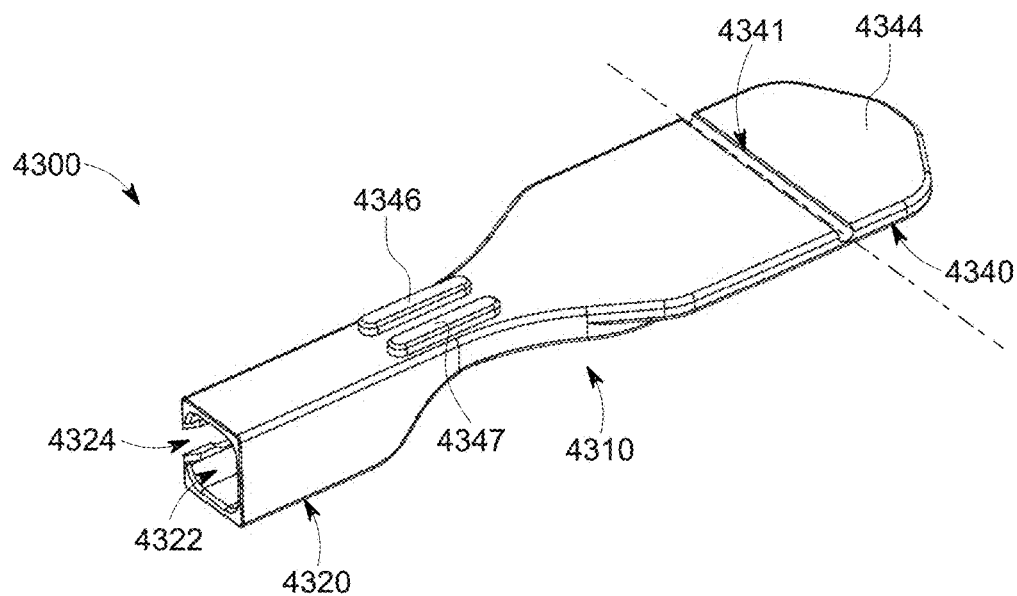
FIG. 63 is a bottom perspective view of the detachable paddle of FIG. 62, according to an embodiment of the present disclosure.
Figure 70:
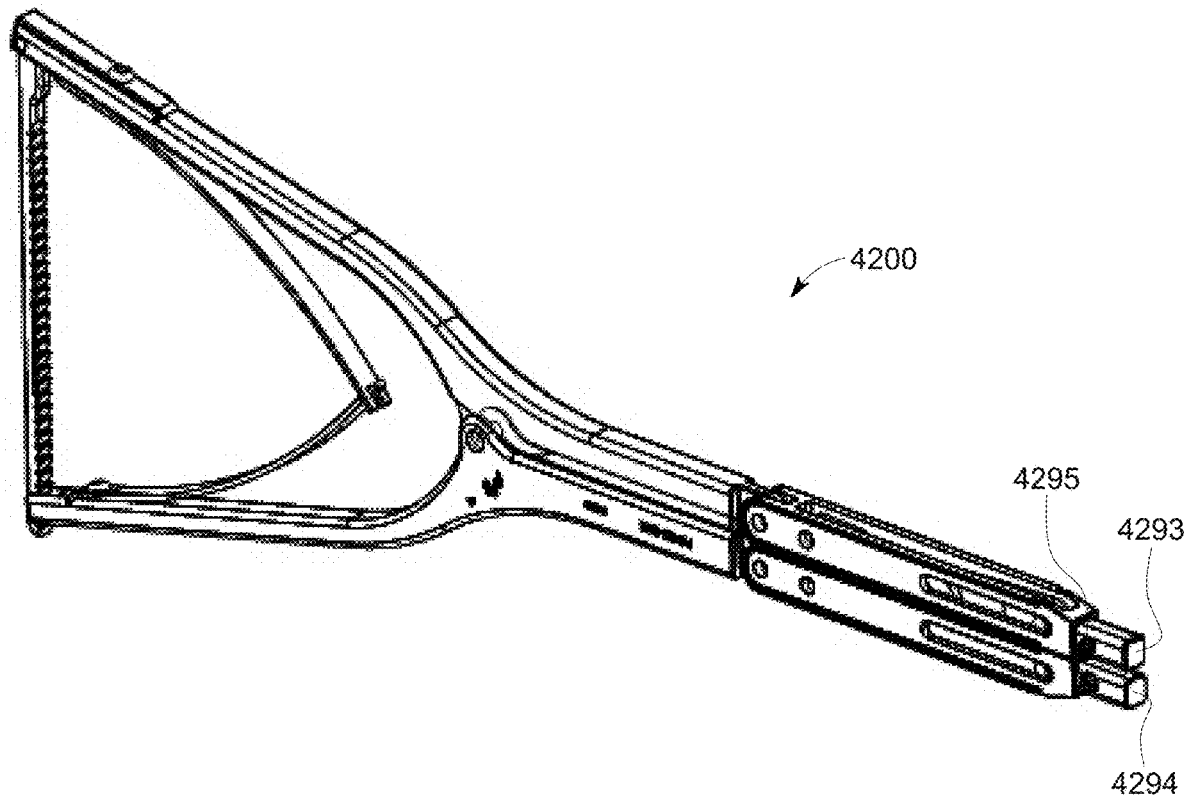
FIG. 70 is a perspective view of a distractor, according to an embodiment of the present disclosure.

In this illustrated embodiment, for example, the detachable tibial paddle 4300 may include a body 4310 having a proximal portion 4320 and a distal portion 4340. With reference to FIGS. 62 and 63, the detachable tibial paddle 4300 may be configured to releasably attach to a first post 4293 (FIG. 70) and/or a second post 4294 (FIG. 70) of a distractor 4200 (FIG. 70). The distal portion 4340 may include a generally planar member having a raised center portion 4342 (FIG. 62) having a first or top planar surface 4347 surrounded by a recessed peripheral surface 4343. The peripheral edge 4345 of the raised center portion 4342 (FIG. 62) of the detachable tibial paddle 4300 may be normal or at a right angle to the surface of the recessed peripheral portion 4343. The distal portion 4340 may include the generally planar member having a second or bottom planar surface 4344 (FIG. 63).

The proximal portion 4320 of the detachable tibial paddle 4300 may include a recess 4322, which is supportable on the posts of the distractor 4200 (FIG. 70). The recess 4322 may have a square cross-section. The proximal portion 4320 may also include a cutout 4324 for receiving a laterally-extending projection 4295 (FIG. 70) on post 4293 (FIG. 70) and/or a laterally-extending projection (not shown in FIG. 70) on post 4294.

Figure 64:
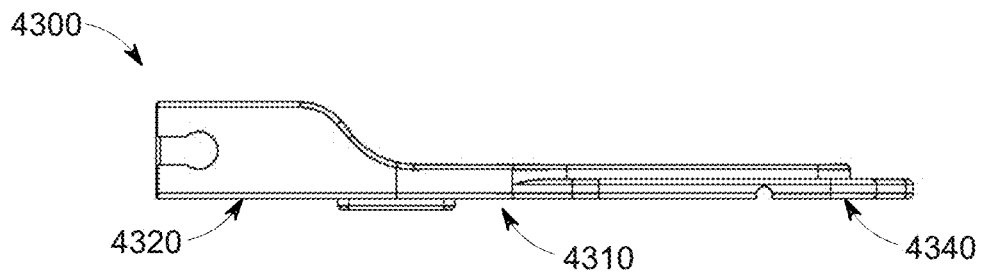
FIG. 64 is a side elevational view of the detachable paddle of FIG. 62, according to an embodiment of the present disclosure.
Figure 65:
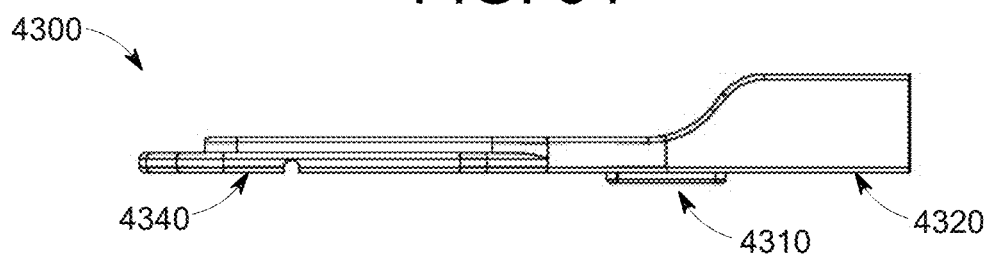
FIG. 65 is a side elevational view of the detachable paddle of FIG. 62, according to an embodiment of the present disclosure.
Figure 66:
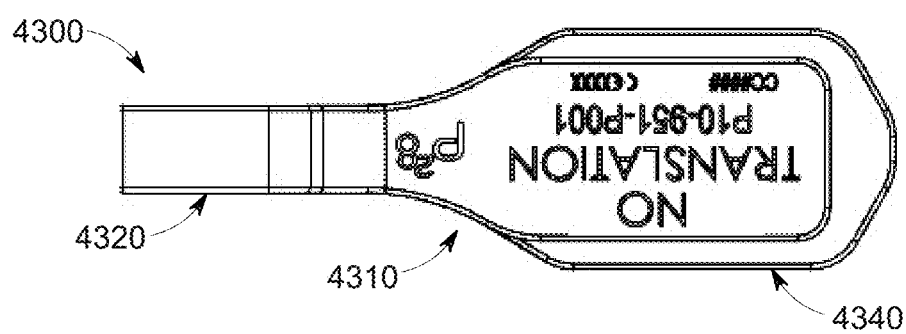
FIG. 66 is a top view of the detachable paddle of FIG. 62, according to an embodiment of the present disclosure.
Figure 67:
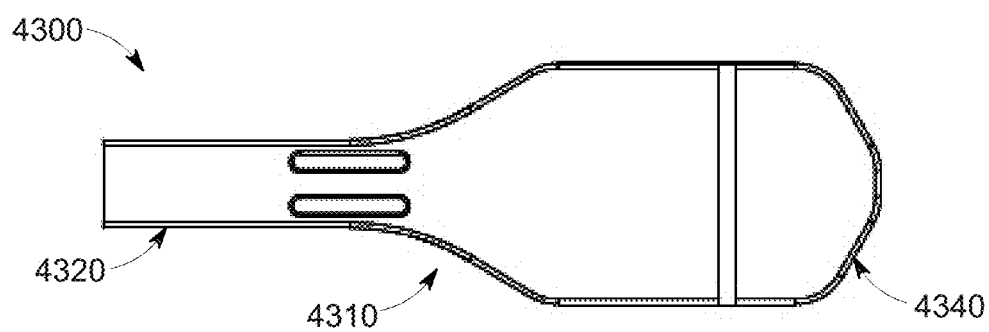
FIG. 67 is a bottom view of the detachable paddle of FIG. 62, according to an embodiment of the present disclosure.
Figure 68:
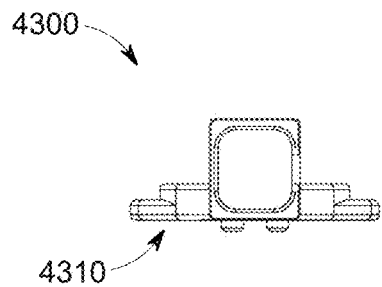
FIG. 68 is front side elevational view of the detachable paddle of FIG. 62, according to an embodiment of the present disclosure.
Figure 69:
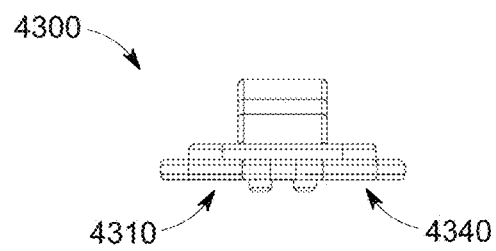
FIG. 69 is back side elevational view of the detachable paddle of FIG. 62, according to an embodiment of the present disclosure.

As shown in FIG. 63, the second planar surface 4344 of the detachable paddle 4300 may include a first raised land 4346 extending from the second planar surface 4344 and a second raised land 4347 extending from the second planar surface 4344. With reference to FIGS. 63 and 64, the proximal portion 4320 of the detachable tibial paddle 4300 may define a longitudinal axis L4 (FIG. 62) and the planar member 4340 of the detachable tibial paddle 4300 may define a longitudinal axis L5 (FIG. 62). As shown in FIG. 62, the longitudinal axis L4 of the planar member 4340 may be offset from the longitudinal axis L5 of the proximal portion 4320. As shown in FIG. 63, the second planar surface 4344 of the detachable tibial paddle 4300 may include a transverse cutout 4341, which as described below, and which defines a centralizing radiographic marker. The raised land 4346 may be an elongated raised land that is disposed on one side of the longitudinal axes L4 (FIG. 62) and L5 (FIG. 62) of the body 4310.

Figure 71:
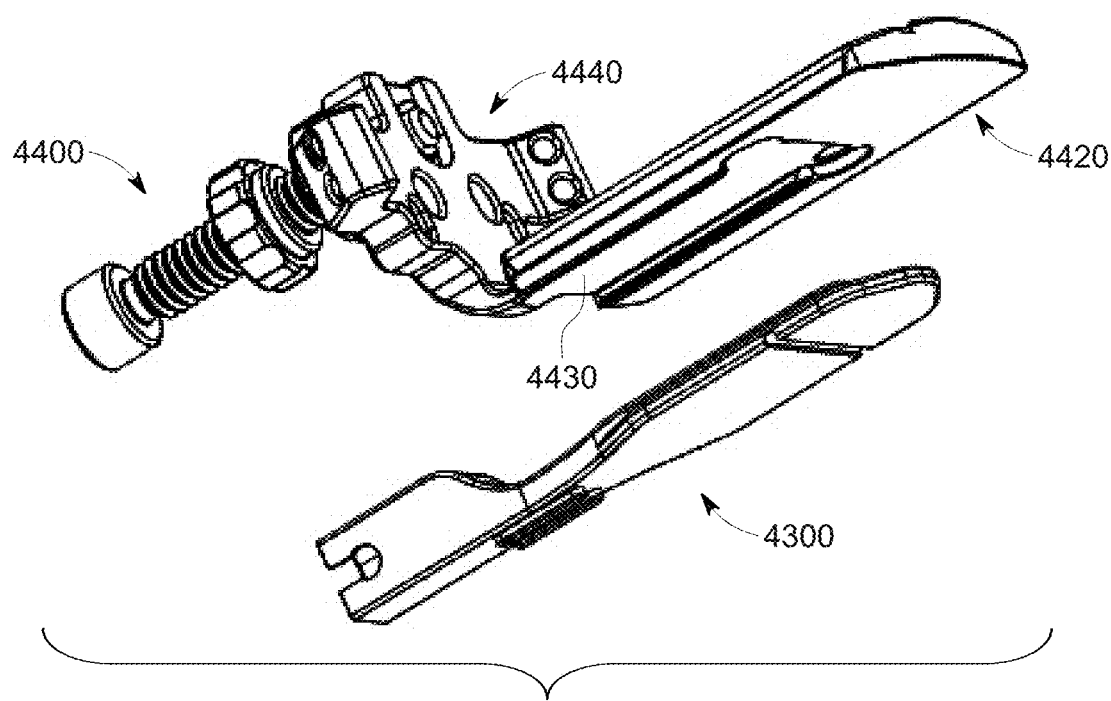
FIG. 71 is an exploded, bottom perspective view of the detachable paddle of FIG. 62 and a tibial implant trialing and cutting guide, according to an embodiment of the present disclosure.
Figure 72:
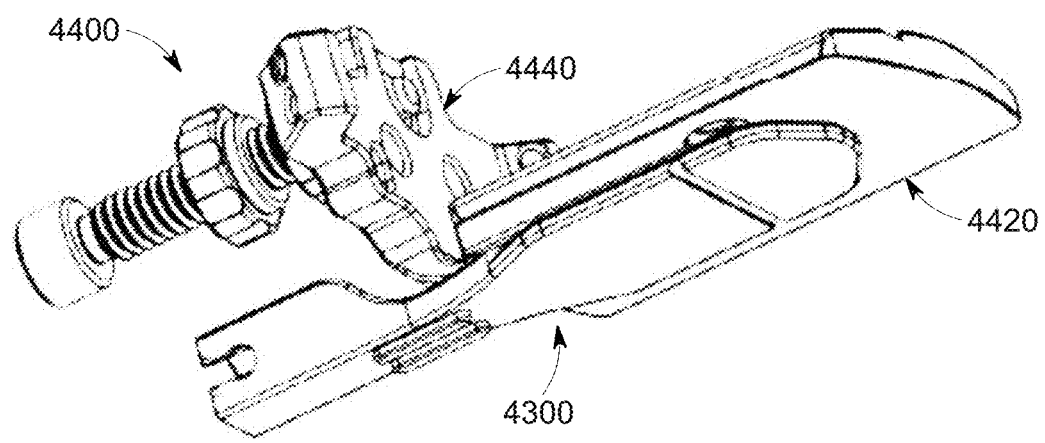
FIG. 72 is a bottom perspective view of the detachable paddle of FIG. 62 nested in the tibial implant trialing and cutting guide, according to an embodiment of the present disclosure.
Figure 73:
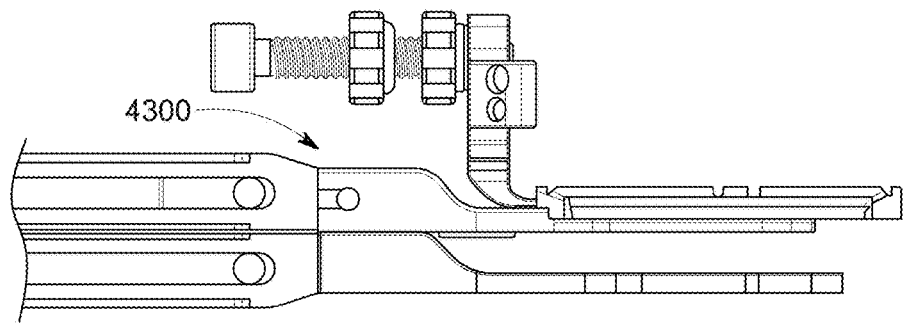
FIG. 73 is a side elevational view of an assembly of the detachable paddle nested in the tibial implant trialing and cutting guide of FIG. 62 along with a distractor and detachable talus paddle, according to an embodiment of the present disclosure.
Figure 74:
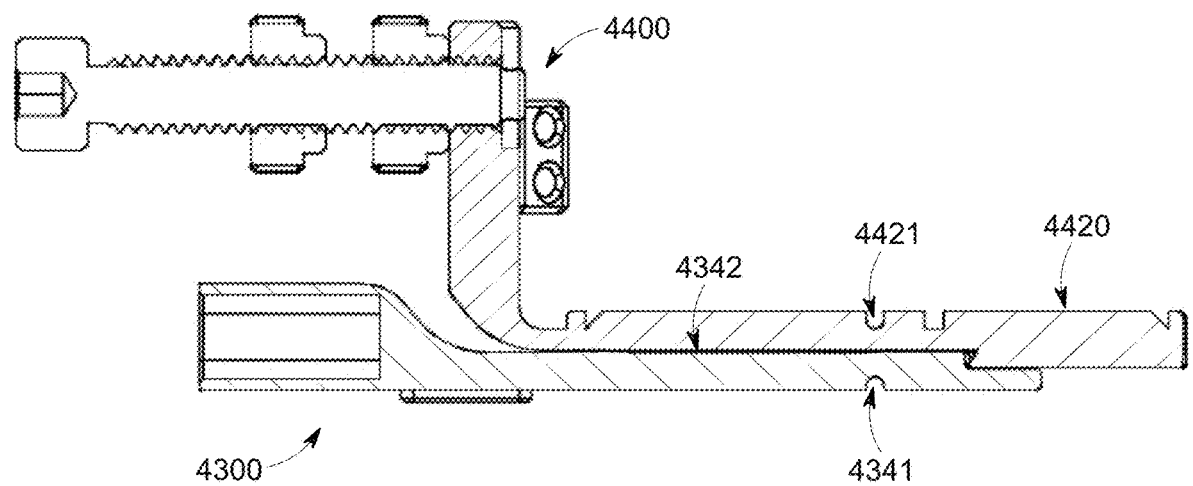
FIG. 74 is an enlarged cross-sectional view of the assembly of FIG. 73, according to an embodiment of the present disclosure.

With reference to FIGS. 71 and 72, a tibial trialing implant component 4400 may be essentially the same as tibial trialing implant component 400 (FIGS. 20 and 21). The tibial trialing implant component 4400 may include a base portion 4420 and an arm or wing portion 4440. A distal side of the base portion 4420 may include a distal recessed portion 4430 (FIG. 71). As shown in FIGS. 73 and 74, the raised center portion 4342 (FIG. 74) of the detachable paddle 4300 may nest or mate within the recessed portion 4430 (FIG. 71) of the tibial trialing implant component 4400. The edge 4345 (FIG. 62), the raised center portion 4342 (FIG. 62) may contact against the recessed sides of the recessed portion 4430 (FIG. 71) to inhibit rotation between the detachable paddle 4300 and the tibial trialing implant component 4400 once nested or mated together. As shown in FIG. 74, the base portion 4420 of the tibial trialing implant component 4400 may include a transverse cutout 4421 defining a centralizing radiographic marker, which is alignable with the transverse cutout 4341 of the detachable tibial paddle 4300.

With reference again to FIG. 71, the sides of the recessed portion 4430 may include an undercut or otherwise be angled toward (or away) the periphery of the base portion 4420 as they extend proximally to a planar proximal end surface to form a sliding dovetail socket or female portion for receiving a corresponding portion of a trialing insert (not shown). In some embodiments, the lateral sides of the raised center portion may be correspondingly angled and configured to form, for example, a dove tail connection.

Figures 75, 76:
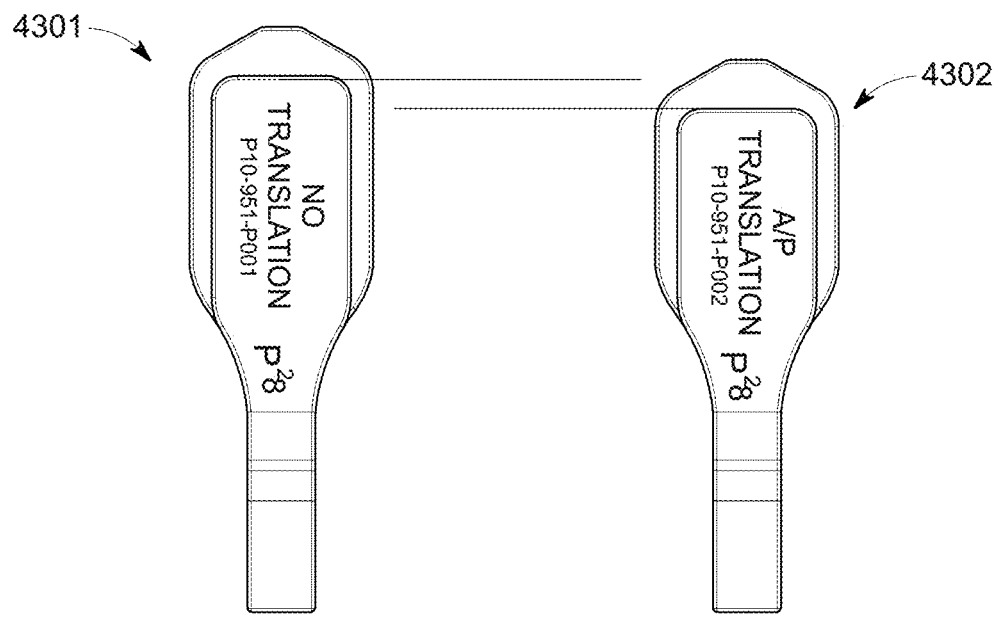
FIG. 75 is a top view of a detachable paddle, according to an embodiment of the present disclosure.
FIG. 76 is a top view of a detachable paddle, according to an embodiment of the present disclosure.

The detachable tibial paddle may be provided in different sizes and configurations. For example, as shown in FIGS. 75 and 76, a first detachable tibial paddle 4301 may be sized and configured to allow centering the talus relative to the tibia. A second detachable tibial paddle 4302 may be sized and configured to allow posterior translation of up to about 4 millimeters. For example, the length of the paddles may be different.

Figure 77:
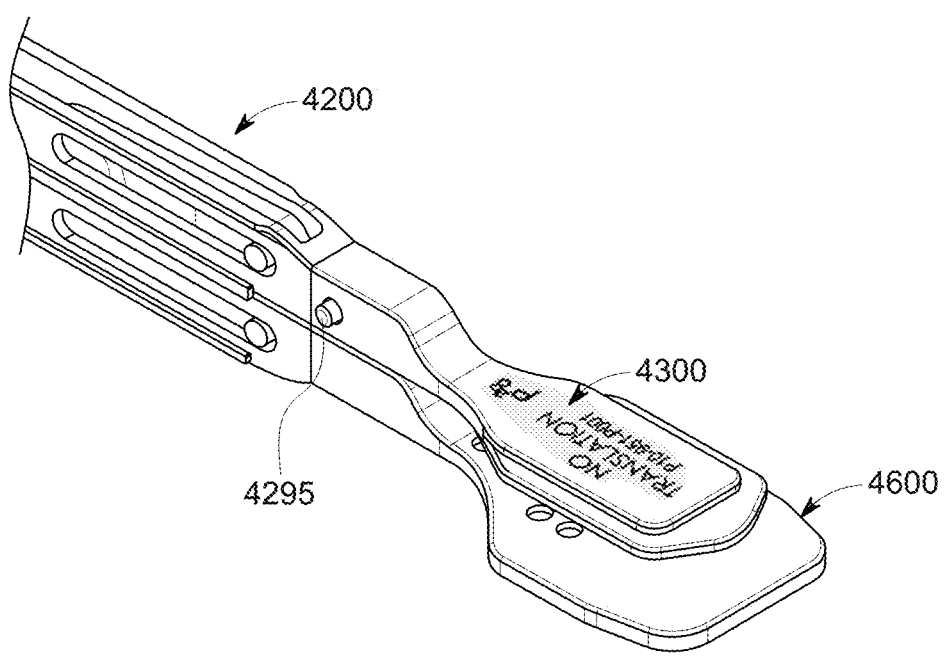
FIG. 77 is a perspective view of an assembly of the distractor of FIG. 70, a detachable paddle, and a detachable talus paddle, according to an embodiment of the present disclosure.
Figure 78:
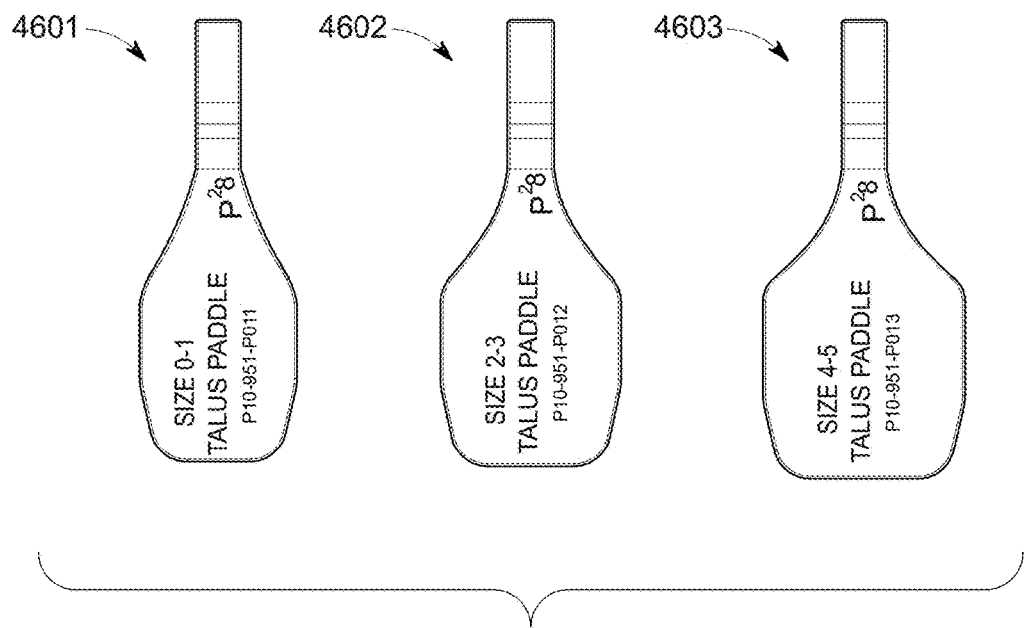
FIG. 78 are top views of a plurality of detachable talus paddles, according to embodiments of the present disclosure.

FIG. 77 illustrates a distal portion of the distractor 4200, a detachable tibial paddle 4300, and a detachable talus paddle 4600, according to an embodiment of the present disclosure. The distractor 4200 may be essentially the same as the distractor 200 (FIG. 2) with the exception of the first post 4295 and the second post (not shown in FIG. 77) having side laterally-extending projections. For example, the first laterally extending projection 4295 may extend to one side of the distractor 4200 for use in securing the detachable tibial paddle 4300. A second laterally extending projection (not shown) may extend to the other side of the distractor 4200 for use in securing the detachable talus paddle 4600. As shown in FIG. 78, various sized and configured detachable talus paddles 4601, 4602, and 4603 may be provided having, for example, different sized or width distal portions.

Figure 79:
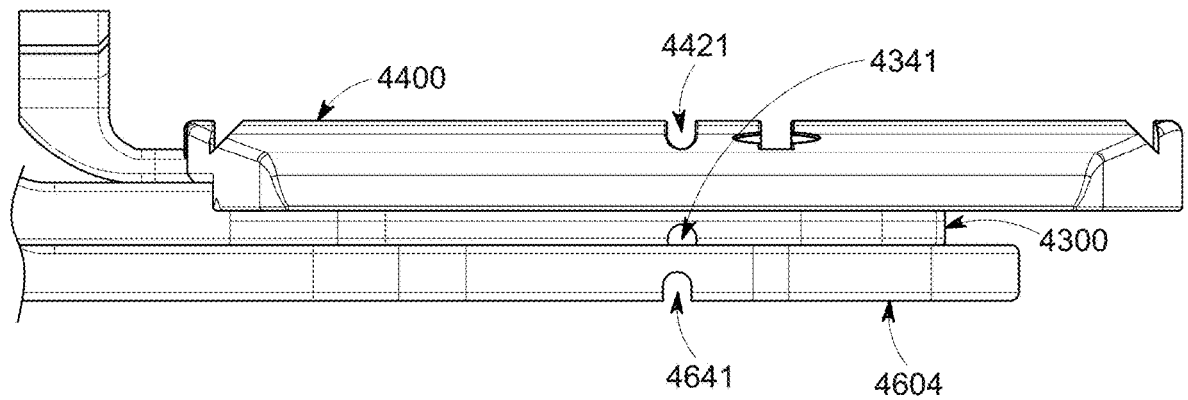
FIG. 79 is a side elevational view of an assembly of a tibial implant trialing and cutting guide, a detachable paddle, and a detachable talus paddle, according to an embodiment of the present disclosure.

With reference to FIG. 79, a detachable talus paddle 4604 may include a transverse cutout 4641, which defines a centralizing radiographic marker. As shown in FIG. 79, the transverse cutout 4641 of the detachable talus paddle 4604, the transverse cutout 4341 of the detachable tibial paddle 4300, and the transverse cutout 4421 of the tibial trialing implant component 4400 may be aligned.

Figure 80:
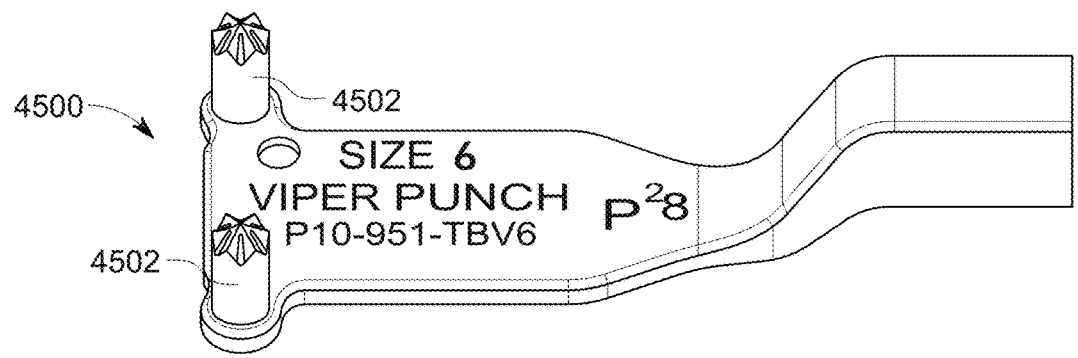
FIG. 80 is a top perspective view of a detachable cutting and/or punch tool, according to an embodiment of the present disclosure.
Figure 81:
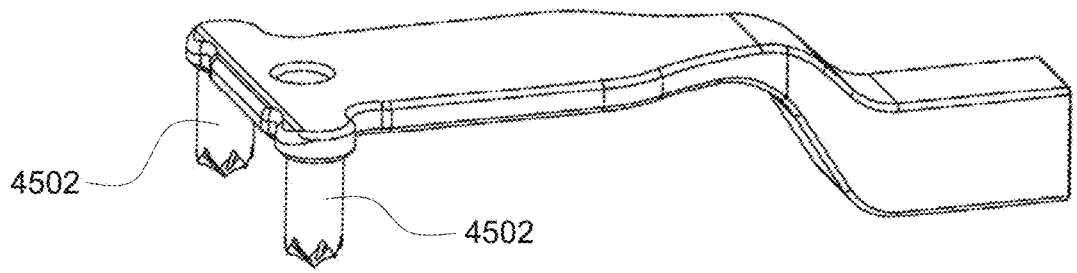
FIG. 81 is a bottom perspective view of the detachable cutting and/or punch tool of FIG. 80, according to an embodiment of the present disclosure.
Figure 82:
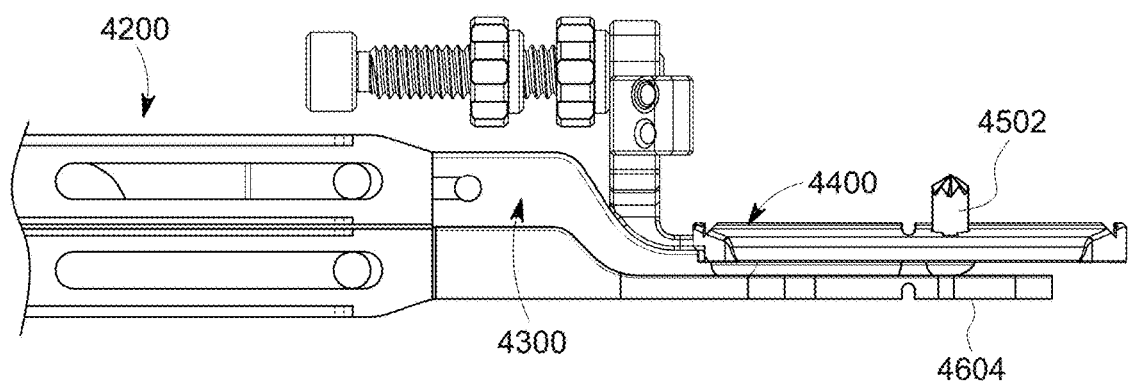
FIG. 82 is a side elevational view of an assembly of the detachable cutting and/or punch tool of FIG. 80 along with a distractor, a tibial trial and cutting guide, and a detachable talus paddle, according to an embodiment of the present disclosure.

FIGS. 80 and 81 illustrate a detachable peg punch paddle 4500, according to an embodiment of the present disclosure. In this illustrated embodiment, the detachable peg punch paddle 4500 is essentially the same as the detachable punch paddle 4300 (FIGS. 62 and 63) with the exception of the shape and configuration of a plurality of pins 4502. For example, as shown in FIG. 82, the distractor 4200 along with the detachable tibial paddle 4300, the tibial trialing implant component 4400, and the detachable talus paddle 4604 may be employed with the cutting and/or punch pins 4502 which are operable to form openings in the distal resected tibia to accommodate at least one peg of a corresponding tibial implant component therein.

Figure 83:
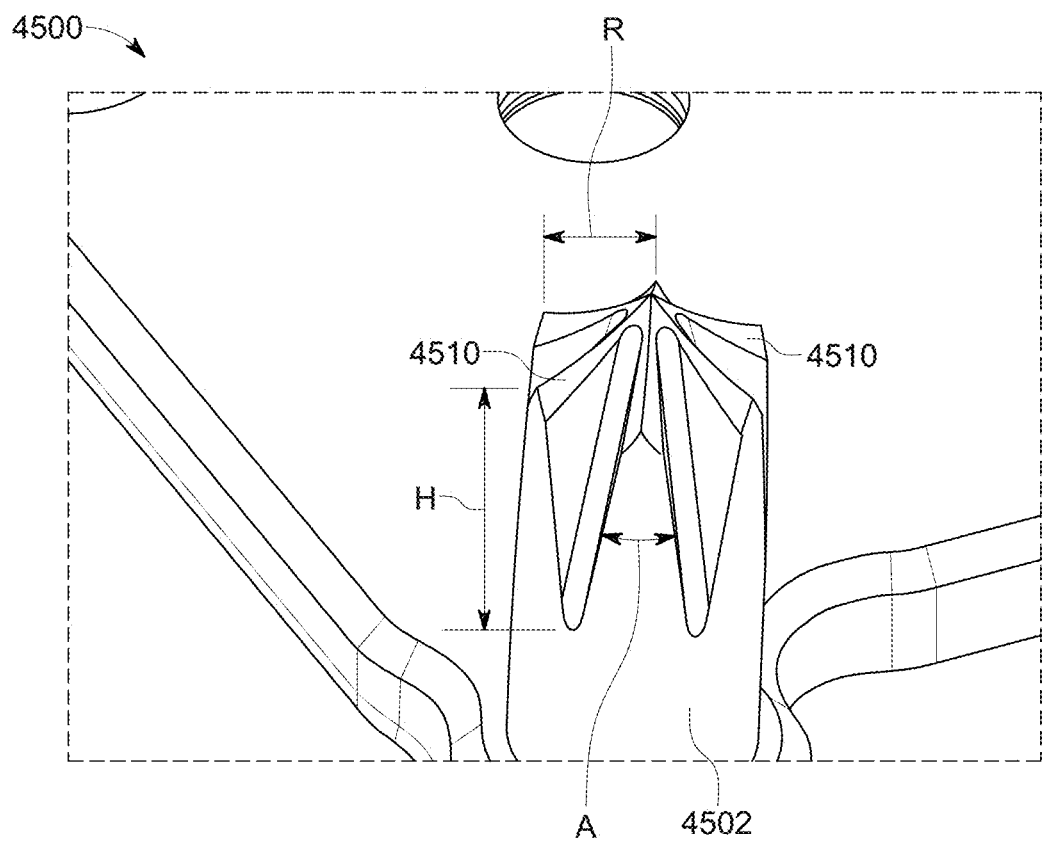
FIG. 83 is an enlarged, partial perspective view of the detachable cutting and/or punch tool of FIG. 80, according to an embodiment of the present disclosure.

As shown in FIG. 83, in this illustrated embodiment, the punch pin 4502 may include deep, aggressive longitudinal serrations to aid in bone preparation. For example, the cutting and/or punch pin 4502 may include longitudinal serrations that extends a distance H, which is greater than the radius R of the cutting and/or punch pin 4502. In some embodiments, the distance H of the longitudinal serrations may be about twice, or more of the radius R of the cutting and/or punch pin. The cutting and/or punch pins 4502 may include six radial cutting edges 4510 that angle downwardly from the center to the periphery of the cutting and/or punch pin 4502.

Figure 84:
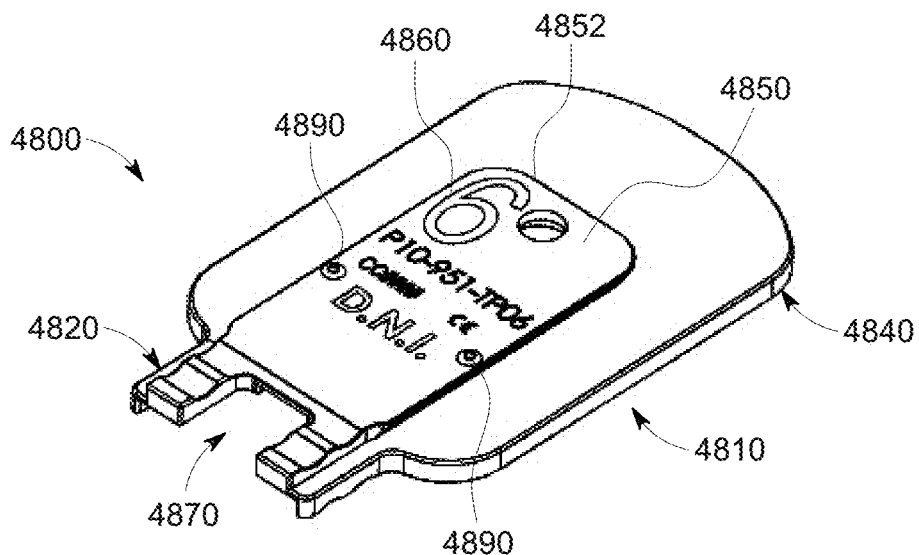
FIG. 84 is a top perspective view of an impaction protector, according to an embodiment of the present disclosure.
Figure 85:
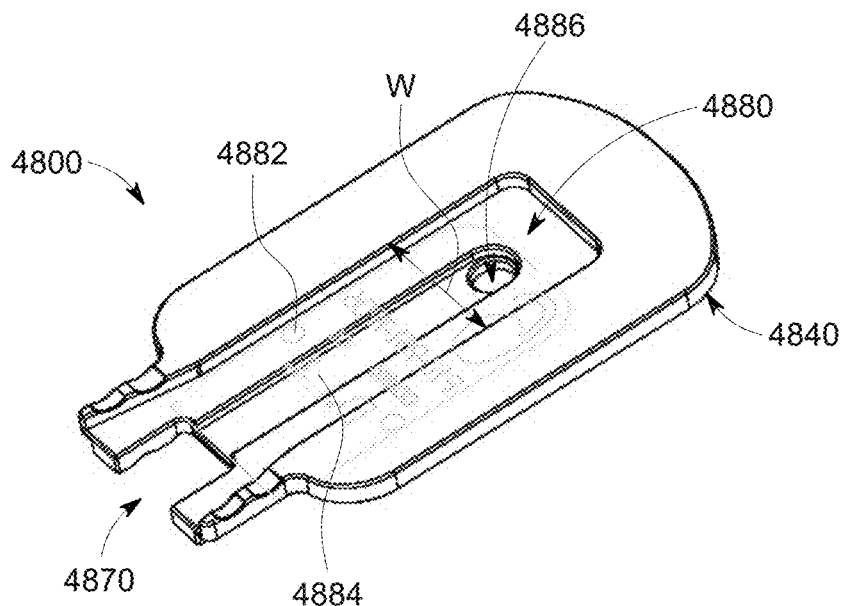
FIG. 85 is a bottom perspective view of the impaction protector of FIG. 84, according to an embodiment of the present disclosure.
Figure 86:
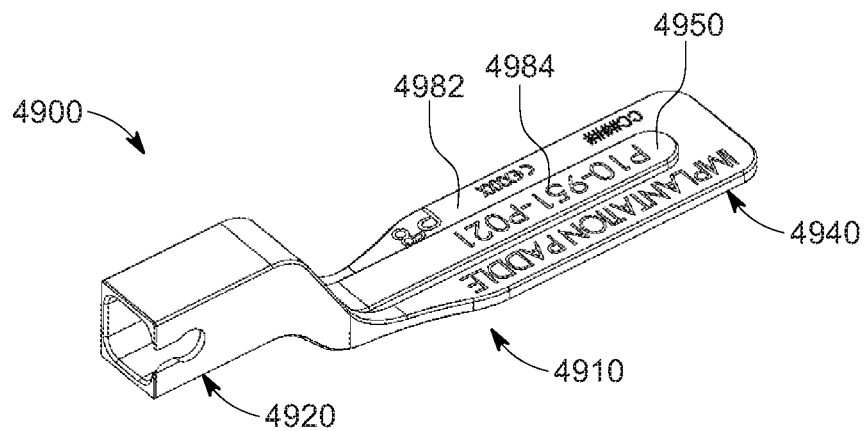
FIG. 86 is a top perspective view of a detachable tibial implantation paddle, according to an embodiment of the present disclosure.
Figure 87:
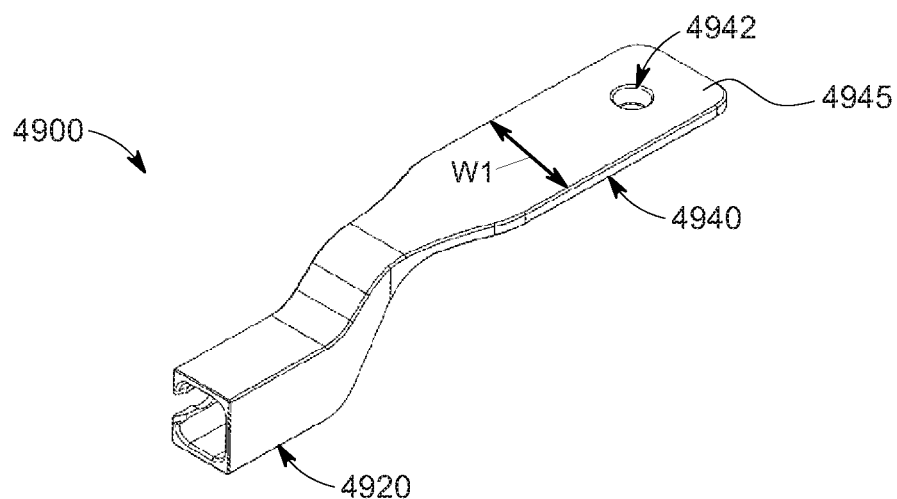
FIG. 87 is a bottom perspective view of the detachable tibial implantation paddle of FIG. 86, according to an embodiment of the present disclosure.

FIGS. 84 and 85 illustrate an impaction protector 4800 and FIGS. 86 and 87 illustrate a detachable tibial implantation paddle 4900 that are nestable together for use in installing a tibial implant component, according to an embodiment of the present disclosure. The impaction protector 4800 and the detachable tibial impaction paddle 4900 are usable with a distractor for installing a tibial implant component, as described in greater detail below.

Figure 88:
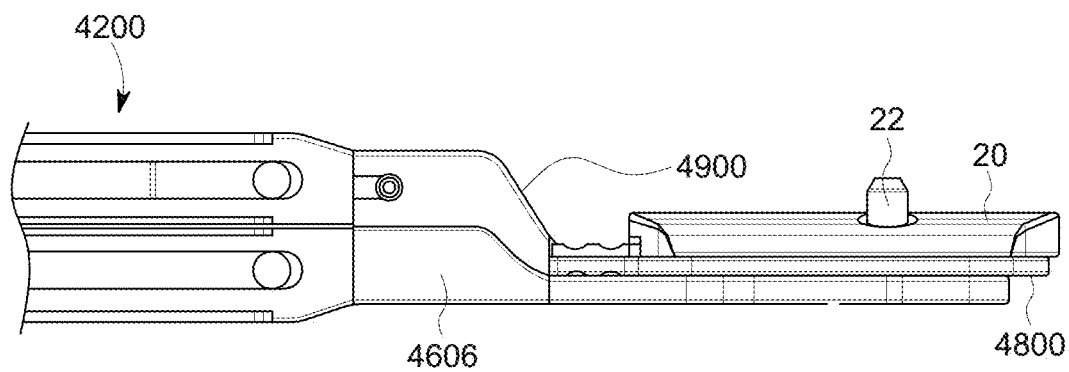
FIG. 88 is a side elevational view of an assembly of the detachable tibial implantation paddle of FIG. 86 along with a distractor, a tibial implant component, and an impaction protector, according to an embodiment of the present disclosure.

With reference again to FIGS. 84 and 85, the impaction protector 4800 may include a body 4810 having a proximal portion 4820 and a distal portion 4840. As shown in FIG. 84, the distal portion 4840 may be generally planar and include a projection or male portion 4850 on the superior side. The raised projection 4850 may be a male portion that is configured to mate and be received in a corresponding recessed portion of a tibial implant component such as the tibial implant component 20 (FIG. 88). For example, the sides of the projection 4850 may include an undercut or otherwise be angled away (or toward) from the periphery of the implant protector 4800 to form a sliding dovetail male portion which may engage the recessed portion of the tibial implant component (e.g., a sliding dovetail socket/female portion). A distal edge 4852 of the projection 4850 may allow for positioning of the impaction protector 4800 along the anterior-posterior direction relative to the tibial implant component. For example, the recess in the tibial implant component may have a corresponding distal edge. The distal portion 4820 may provide a handle or end engageable by a surgeon for releasably attaching the impaction protector 4800 to the tibial implant component. In addition, a cutout 4870 may be provided in the handle to provide clearance for the proximal portion of the detachable tibial implantation paddle 4900 (FIGS. 86 and 87) as further described below. In another embodiment, the projection 4850 may have flat sides, (e.g., sides that are normal or perpendicular to the superior planar surface of the impaction protector 4800. Indicia 4860 such as a number may be provided on the impaction protector to identify and correspond to the corresponding selected sized tibial implant component. Interference features 4890 (FIG. 84) may be provided, e.g., stick fit to the impaction protector 4800.

As shown in FIG. 85, the distal portion 4840 of the impaction protector 4800 may include a recessed elongated cavity 4880 having a first recessed surface 4882, and a second center recessed surface 4884 for nesting or mating with the superior surface 4984 (FIG. 86) of the detachable tibial implantation paddle 4900 (FIG. 86). The second center recessed surface 4884 of impaction protector 4800 may include a hole 4886 for use with a bossed implant impaction system 5000 (FIG. 90) described below. The impaction protector 4800 is used to protect the tibial implant component 20 while impacting and may be formed from a generally resilient material. For example, the impaction protector 4800 may be formed from a material that is more resilient than the tibial implant component 20. For example, the impaction protector 4800 may be formed from a material that is more resilient than the detachable tibial implantation paddle 4900. In some embodiments, the impaction protector 4800 may be formed from an implant grade UHMWPE (ultra-high-molecular-weight polyethylene) material that is operable to protect the tibial implant component 20 while impacting. It will be appreciated that other polymeric or like material may be suitably employed.

With reference to FIGS. 86 and 87, the detachable tibial implantation paddle 4900 is operable for use with the impaction protector 4800 (FIG. 84) in, for example, for installing a tibial implant component. The detachable tibial implantation paddle 4900 may include a body 4910 defining a proximal portion 4920 and a distal portion 4944. The proximal portion 4920 may be operably releasably connectable to the distractor 4200 (FIG. 88). The distal portion 4940 may include a generally planar member having a superior surface 4950 (FIG. 86) and an inferior surface 4945 (FIG. 87). As shown in FIG. 86, the superior portion of the distal portion 4940 of the detachable tibial implantation paddle 4900 may include the elongated raised center portion 4984, and a recessed peripheral edge portion 4982. As shown in FIG. 87, the inferior portion of the distal portion 4940 of the detachable tibial implantation paddle 4900 may include an impaction tool locator or recessed hole or cavity 4942.

Figure 89:
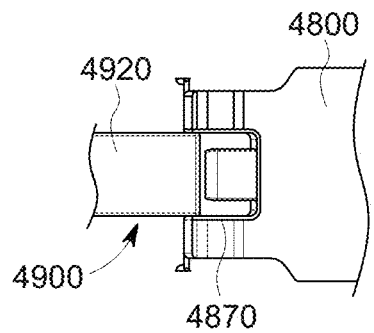
FIG. 89 is a partial top view of the assembly of FIG. 88, according to an embodiment of the present disclosure.
Figure 90:
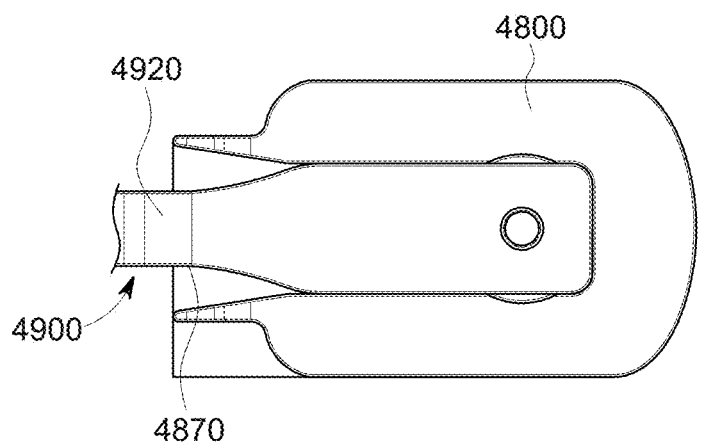
FIG. 90 is a partial bottom view of the assembly of FIG. 88, according to an embodiment of the present disclosure.

FIG. 88 illustrates an assembly for implanting the tibial implant component 20, according to an embodiment of the present disclosure. The distractor 4200 along with the detachable tibial implantation paddle 4900, the impaction protector 4800, and a detachable talus paddle 4606 are operable for use in installing the tibial implant component 20. For example, the tibial implant component 20 includes posts 22 or other projections that are received in the recesses earlier formed in the resected tibia such as described above. FIGS. 89 and 90 illustrates the proximal portion 4920 of the detachable tibial implantation paddle 4900 disposed in the cutout 4870 of the impaction protector 4800.

With reference to FIG. 91, therein illustrated is an implant impaction system 5000, according to an embodiment of the present disclosure. The implant impaction system 5000 may include a body 5100 and a detachable projecting member 5200. The implant impaction system 5000 may be essentially the same as the implant impaction system 3000 (FIG. 54) described above.

In this illustrated embodiment, as shown in FIG. 92, the detachable projecting member 5200 may include a proximal portion 5202 and a distal portion 5204. The proximal portion 5202 may be releasably attachable to a distal portion 5140 (FIG. 91) of the body 5100 (FIG. 91). In some embodiments, the U-shaped configuration of the body 5100 may be disposed along a plane, and when the projected member 5200 is attached to the distal portion 3140 of the body 3100, a distal end 5208 of the detachable projection member 5204 is offset from the plane.

Figure 102:
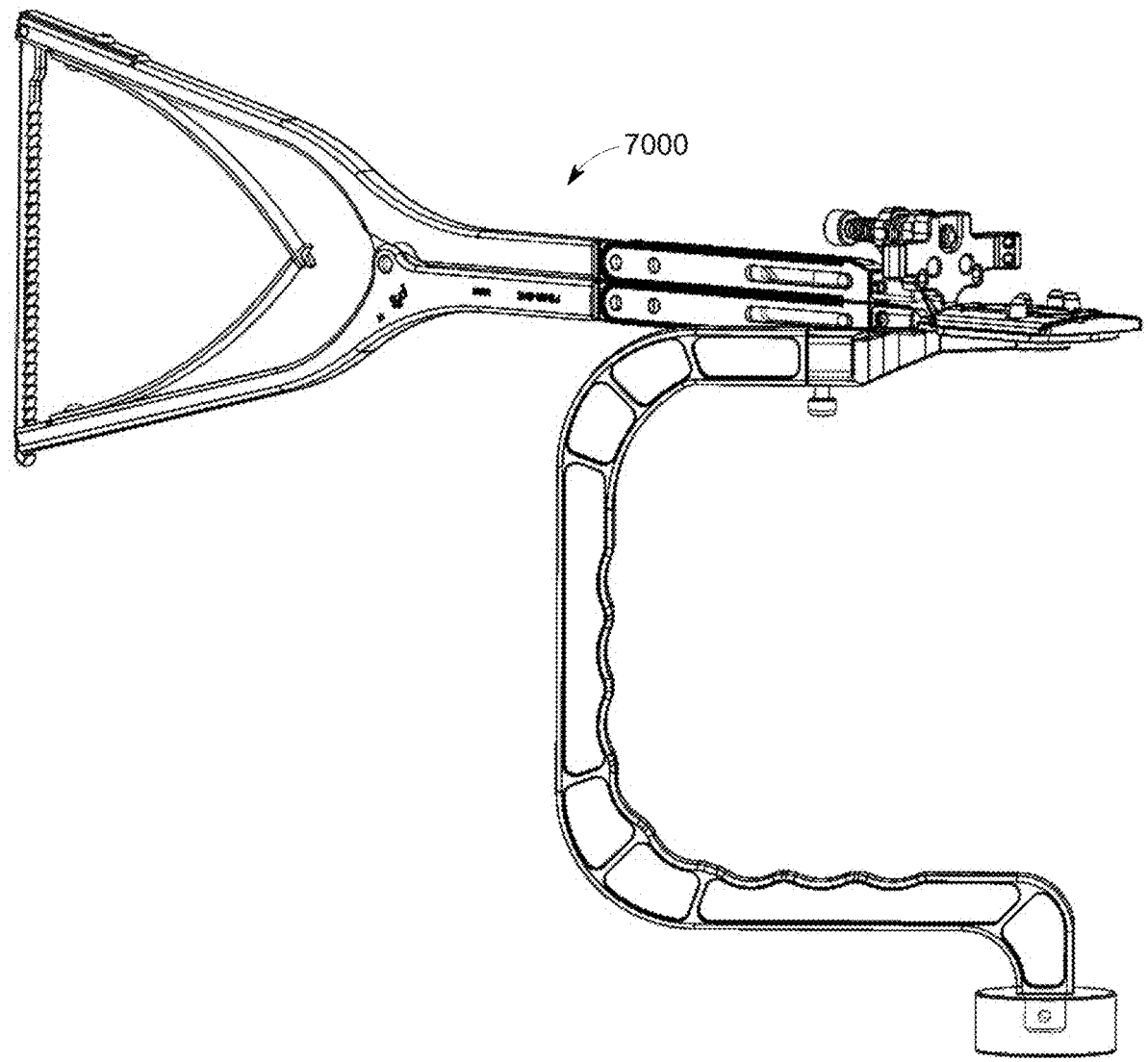
FIG. 102 is a perspective view of the implant impaction system the projecting member employed with the distractor for implanting a tibial implant component, according to an embodiment of the present disclosure.

The distal portion 5204 of the detachable projecting member 5200 may include an enlarged circular disc portion 5241 with a center pin 5245, which as shown in FIG. 93, the center pin 5245 is received in the hole 4942 of the detachable tibial implantation paddle 4900, which the detachable tibial implantation paddle 4900 is attached to the distractor (not shown in FIG. 93). With reference still to FIG. 93, for example, the diameter of the circular disc portion 5241 may be sized about equal to a width W1 (FIG. 87) of the detachable tibial implantation paddle 4900. With reference again to FIG. 91, a proximal portion 5130 may include an enlarged knob 5135. The implant impaction system 5000 may be used with traditional impaction instruments such as a hammer. The implant impactor system 5000 may include a plurality of differently sized and configured detachable impaction protectors, each of which being supportable on the distal portion of the implant impaction system 5000. As shown in FIG. 102, the implant impaction system 5000 with the projecting member 5200 may be employed with the distractor 4200 for implanting a tibial implant component.

Figure 94:
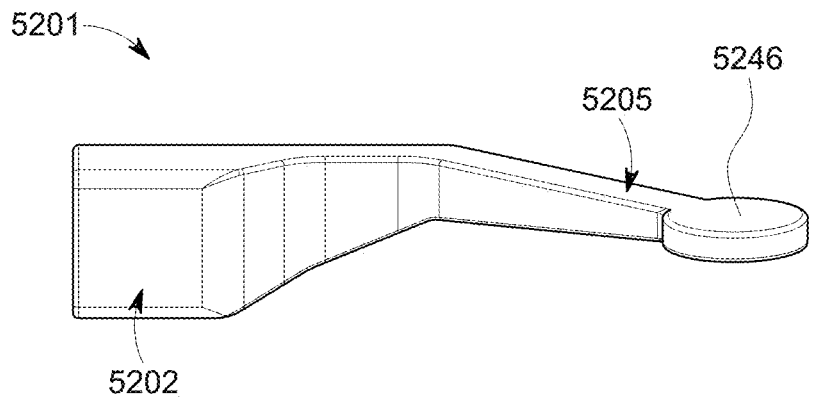
FIG. 94 is a perspective view of a detachable projecting member, according to an embodiment of the present disclosure.
Figure 95:
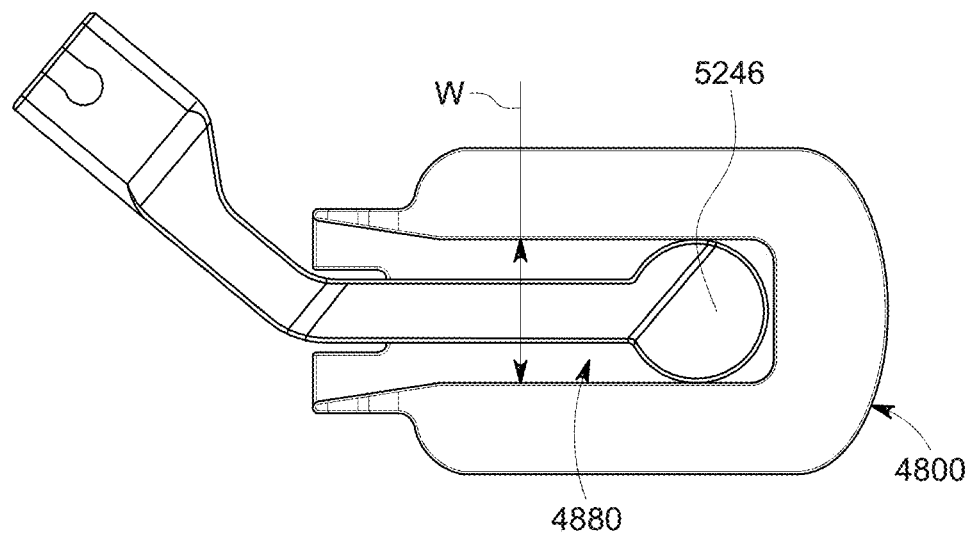
FIG. 95 is a bottom view of the detachable projecting member of FIG. 94 nested in a tibial impaction protector, according to an embodiment of the present disclosure.

FIG. 94 illustrates another embodiment of a detachable projecting member 5201 that may include a proximal portion 5202 and a distal portion 5205. The proximal portion 5202 may be releasably attachable to a distal portion 5140 (FIG. 91) of the body 5100 (FIG. 91) of the implant impaction system 5000. In this illustrated embodiment, the distal portion 5205 of the detachable projecting member 5200 may include an enlarged circular disc portion 5241 with a flat surface 5246, which as shown in FIG. 94, the circular disc portion 5241 is receivable in the cavity 4880 of the impaction protector 4800. The diameter of the circular disc portion 5246 may be sized slightly less than the width W of the cavity 4880.

Figure 96:
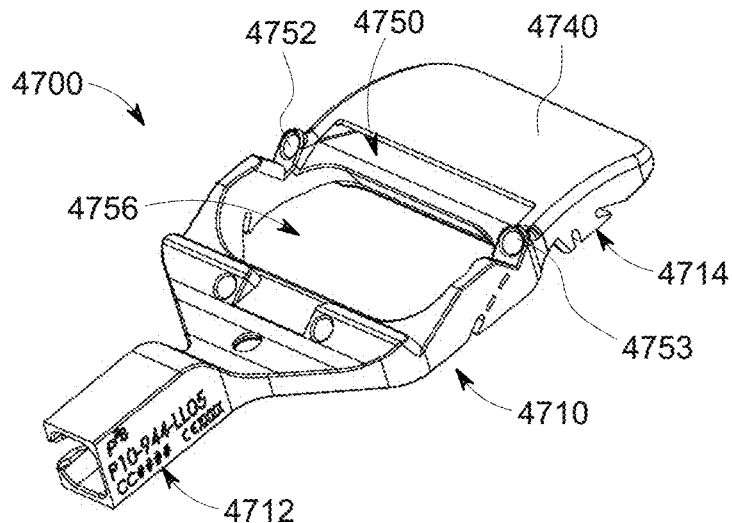
FIG. 96 is a top perspective view of a detachable talar implant trialing and cutting guide, according to an embodiment of the present disclosure.
Figure 97:
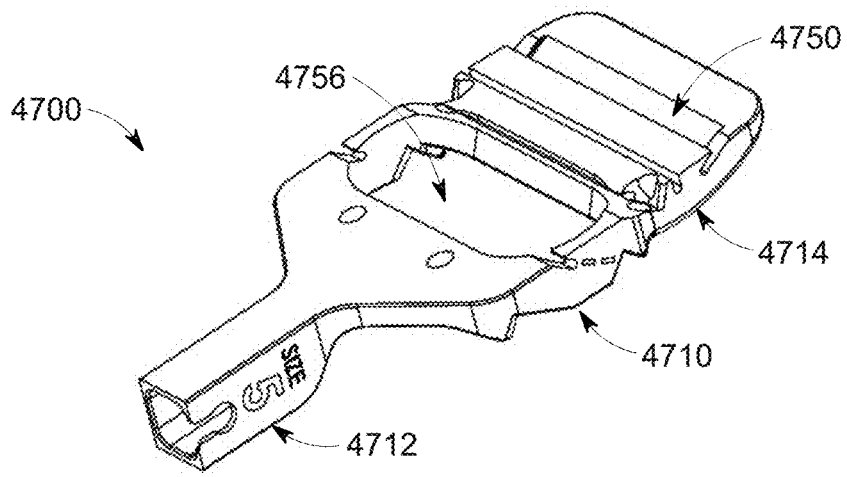
FIG. 97 is a bottom perspective view of the detachable talar implant trialing and cutting guide of FIG. 96, according to an embodiment of the present disclosure.
Figure 98:
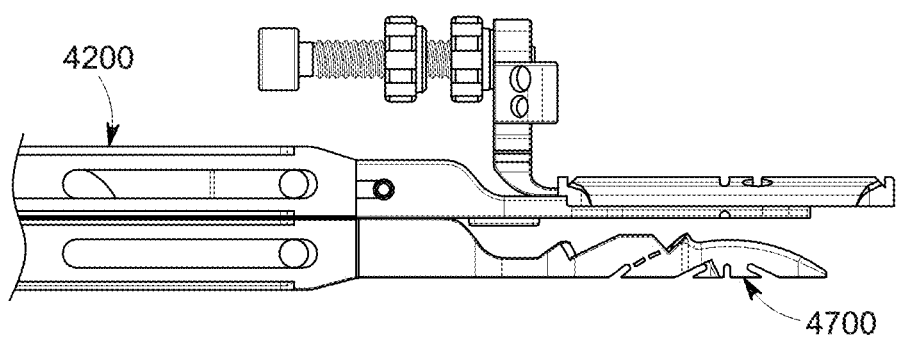
FIG. 98 is a side elevational view of an assembly of the talar implant trialing and cutting guide of FIG. 96, a distractor, a detachable paddle, and a tibial trialing implant, according to an embodiment of the present disclosure.

FIGS. 96 and 97 illustrate a detachable talar implant trialing and cutting guide 4700 for use with a direct connection to the distractor 4200 as shown in FIG. 98, according to an embodiment of the present disclosure. With reference again to FIGS. 96 and 97, the detachable talar implant trialing and cutting guide 4700 may include a body 4710 having a proximal portion 4712 and a distal portion 4714. The proximal portion 4712 may be configured for directly releasably attaching to a lower post 4294 (FIG. 70) of the distractor 4200 (FIG. 98). As best shown in FIG. 96, a superior surface 4740 of the detachable talar implant trialing and cutting guide 4700 may include a curved surface 4740. Other features of the detachable talar implant trialing and cutting guide 4700 may generally include a cut slot 4750, pin apertures 4752 and 4753, and a window or aperture 4756 extending therethrough. The pin apertures 4752 and 4753 may be configured to accept a pin, k-wire or other bone fixation member therethrough and into a talus. The cut slot 4750 can be utilized as a cut guide for the removal of a posterior portion of the talus that extends (and therefore is angled) distally and posteriorly from the resected proximal surface of the talus. The anterior window 4756 may be positioned over the anterior side of a talus such that the window 4756 can be utilized with a cut guide for the removal of an anterior portion of the talus that extends (and therefore is angled) distally and anteriorly from the resected surface of the talus. It will be appreciated that differently sized detachable talar implant trialing and cutting guides 4700 may include differing anterior-posterior lengths, medial-lateral widths and/or proximal-distal thicknesses. The talar implant trialing and cutting guides 4700 may be the same or similar to the talar implant trialing and cutting guides described in U.S. provisional application No. 62/779,092, entitled "Instruments, Guides And Related Methods For Total Ankle Replacement", and International PCT Patent Application, filed Dec. 13, 2019, entitled "Instruments, Guides And Related Methods For Total Ankle Replacement", which are hereby incorporated by reference in their entirety herein.

Figure 99:
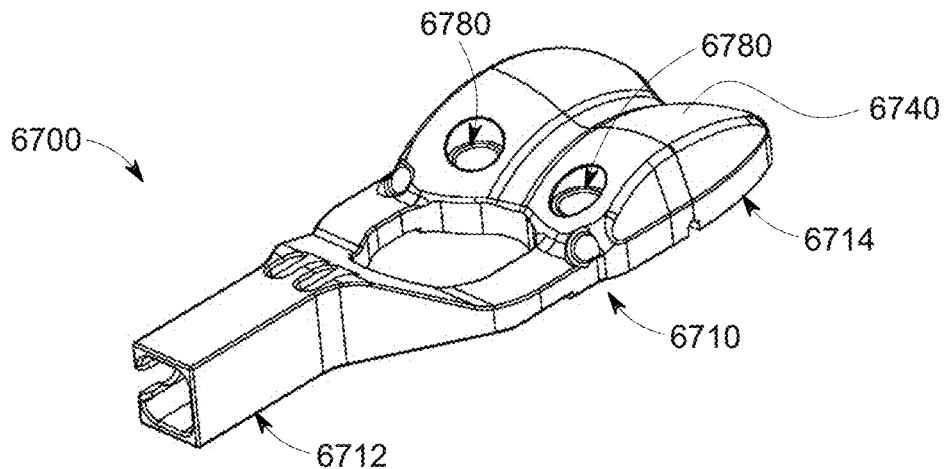
FIG. 99 is a top perspective view of a detachable talar implant trialing and cutting guide, according to an embodiment of the present disclosure.
Figure 100:
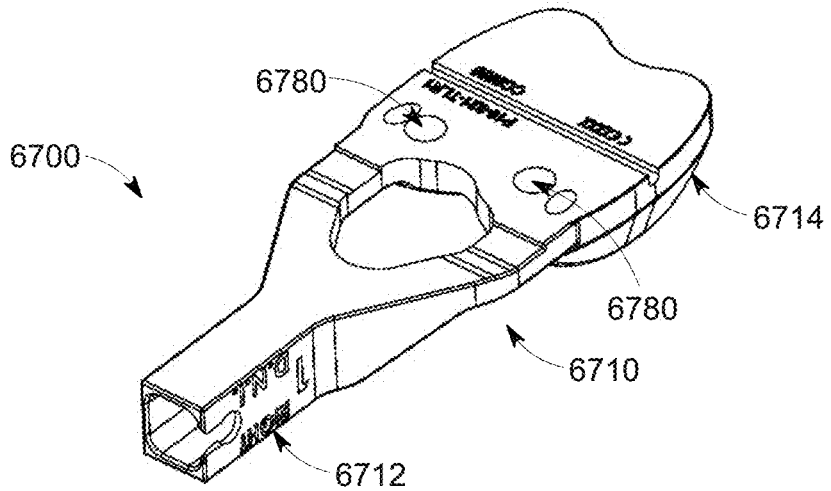
FIG. 100 is a bottom perspective view of the detachable talar implant trialing and cutting guide of FIG. 99, according to an embodiment of the present disclosure.
Figure 101:
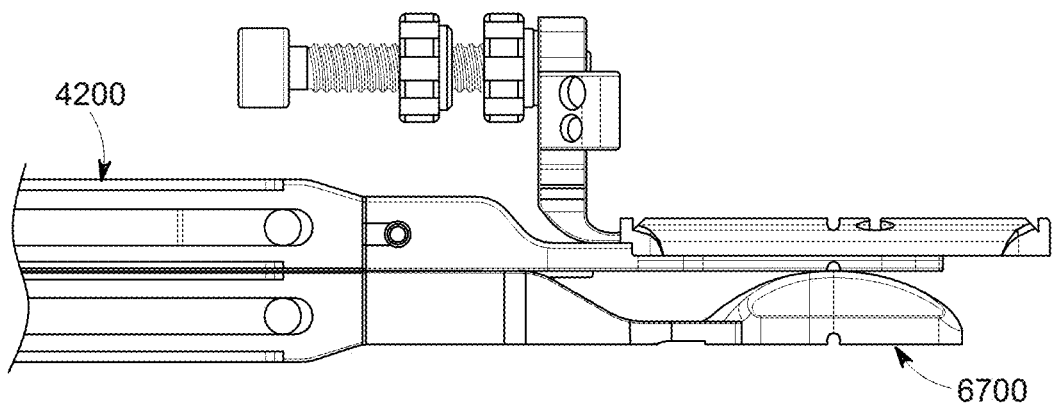
FIG. 101 is a side elevational view of an assembly of the detachable talar implant trialing and cutting guide of FIG. 99, a distractor, a detachable paddle, and a tibial trialing implant, according to an embodiment of the present disclosure.

FIGS. 99 and 100 illustrate a detachable flat talus implant trialing and cut guide 6700 for use with a direct connection to the distractor 4200 as shown in FIG. 101, according to an embodiment of the present disclosure. With reference again to FIGS. 99 and 100, the detachable flat talus implant trialing and cut guide 6700 may include a body 6710 having a proximal portion 6712 and a distal portion 4714. The proximal portion 4712 may be configured for directly releasably attaching to a lower post 4294 (FIG. 70) of the distractor 4200 (FIG. 101).

The detachable flat talus implant trialing and cut guide 6700 may include an articulation surface 6740 that corresponds to a talar implant component (not shown) that contacts and articulates (via sliding/gliding motion) with that of a corresponding tibial insert (not shown). The articulation surface 6740 of the detachable flat talus implant trialing and cut guide 6700 may thereby provide a close approximation of the articulation surface of the corresponding talar component such that the size and range of motion of the corresponding talar component be tested or trialed via the articulation surface 6740 of the flat talus trial component 6700.

The detachable flat talus implant trialing and cut guide 6700 may include at least one drill guide through-hole 6780 for use by a surgeon in forming holes in the resected talus for the pegs of a talar implant component.

In the various described embodiments of the present disclosure. the various components may be formed from a metal and/or polymeric material. The connection of the paddles to the distractor, and the connection of the projecting member to the implant impaction system may have other suitabley sized and configured matingly-engaging portions such as circular posts or other shaped poses and recesses, be releasably connectable in a snap fit manner or with a snapfit connector, be threadably releasably connectable, or may be assembled and attached in any suitable suitable manner. In some embodiments, one of the paddles may be fixed and integral with the distractor.

It will be appreciated that the above described detachable tool may be interchangeable and usable on both the distractors and the body of the implant impaction system.

An embodiment of a surgical procedure using the above described components may be as follows. A tibial trailing implant component may be correspondingly sized to a sizing resection block (not shown). By hand, the tibial trailing implant component may be slid over two medial/lateral pins such as 2.4 mm smooth Steinmann Pins on the anterior aspect of the distal tibia, which pins were earlier installed and used to support the sizing resection block. The tibial trailing implant component may be inserted such that the anterior surface of the tibial trailing implant component is approximately flush to the anterior tibia. The pins in the slots are centered to ensure appropriate varus/valgus and superior/inferior placement against the inferior surface of the tibia. A 4-Bar Parallel Distractor such as the distractors described above may be used to distract the tibiotalar joint and confirm the provisional tibial trailing implant component position using AP and lateral fluoro. The center of a tibial trial notch (e.g., notch 429 in FIG. 20) may be aligned with the posterior tibia wall. A long tibia size may be desired if uncertain whether the notch of the tibia trial is located within the tibia or not. Full anterior/posterior coverage with minimal overhang may be desired. The tibial trailing implant component is tightened against the anterior tibia by rotating a distal most set screw on the tibia trial clockwise until the tibia trial and anterior tibia are flush. Using a lateral fluoro view, the tibia implant length is determined. The notch of the tibial trial comes into view on the lateral view. If the notch is located beyond the posterior tibia, a regular tibia size should be used. If the notch is located within the tibia, a long tibia size may be used.

Once sizing of the tibial trailing implant component has been evaluated, the distractor with detachable paddles are used so that the paddles are received in the resected tibiotalar joint. For example, the superior paddle's dovetail connection may be operably slid into the inferior aspect of the tibial trailing implant component. The joint is distracted by squeezing down on the handle of the distractor to apply even pressure against the tibial trailing implant component and the talar cortical surface to fully seating the tibial trial into position. The tibial trailing implant component position may be checked on AP and lateral fluoro views to ensure position and fit. With the distractor in place, threaded shoulder pins may be inserted into two of the 4 proximal converging pin holes (e.g., two of holes 441 in the tibial trailing implant component 400) using a one of the holes on each side.

In one embodiment, with the converging shoulder pins in place, the distractor is removed from the tibiotalar joint. The corresponding detachable paddle is replaced with the detachable punch paddle (e.g., such as detachable detachable peg punch paddle 500 (FIG. 25) or detachable peg punch paddle 4500 (FIG. 80)) corresponding to the selected tibial trailing implant component and operably attached to the distractor.

The distractor is inserted into the resected tibiotalar joint, ensuring that the detachable punch paddle is facing superiorly. The punch pins are aligned with the inferior holes in the tibial trailing implant component and position is verified using AP and lateral fluoro as well as visually. The surgeon may begin to distract the distractor under lateral fluoroscopy.

Using the previously assembled construct (e.g., assembly 7000 as shown in FIG. 102), insert the impaction dimple (e.g., projection 5245 shown in FIG. 92) underneath the punch paddle. The distal end of the impaction assembly is impacted, still under the distractor until the punch paddle is fully seated.

In another embodiment, the distraction need not be used but just the impactions assembly. In this embodiment, for example, the detachable punch paddle may be aligned with the holes in the tibial trailing implant component. The impaction handle is attached to the detachable punch paddle. Both visually and under fluoro, the detachable punch paddle is perpendicular to the long axis of the tibia (e.g., the punch pins being parallel to the long axis of the tibia) and verifying position using AP and lateral view. Under fluoro, a mallet is used (e.g., two to four strikes) on the distal end of the impaction handle to impact the punch pins into the tibia. Confirmation may be made that complete seating of the punch pins has occurred relative to the tibial trailing implant component by direct visualization under fluoroscopy.

An embodiment of a chamfer-cut, talar trial positioning may be as follows. By hand, a surgeon may initially place the detachable talus trialing implant and cut guide into the joint to evaluate coverage. Visually and under fluoro, confirmation of the guide size in assessing coverage on talus, ensuring that the guide adequately covers the medial and lateral aspect of the dorsal cut without impinging on the gutters and vertical line on trial aligns with the lateral process. Once sizing has been evaluated, the guide may be removed and attached to a distractor. The talus trialing implant and cut guide is reinserted into the resected tibiotalar joint, matching a superior paddle's dovetail connection to an inferior aspect of a tibial implant trialing and cutting guide and the inferior aspect of the talus trialing implant and cut guide to the resected talar bone (e.g., construct as shown in FIG. 98) disposed in the joint.

The joint is distracted by squeezing down on the distractor handle, applying even pressure against the tibial/talar trial guides and the tibiotalar cortical surfaces preparing to fully seat the talus trialing implant and cut guide into position. With the parallel distractor in place, re-check the talus trialing implant and cut guide position under a lateral fluoro view to ensure position and fit before setting into place with shoulder pins. The selected talus trialing implant and cut guide can be sized up or down to achieve appropriate coverage. Plantarflexing the tibiotalar joint to achieve appropriate visualization before setting in place may be desired. Under the same view, ensure that the cutting slots for the anterior and posterior chamfers are resecting an appropriate amount of talus. With the talus trialing implant and cut guide attached to the 4-Bar Parallel Distractor and positioned in place, is followed by subsequent pin fixation steps. Pins such as 2.4 mm smooth Steinmann pin may be placed into the medial anterior hole in the talus trialing implant and cut guide and retrieve (2) threaded shoulder pins. Plantarflex the foot to expose the converging pin holes located more posteriorly on the guide. Under power, place the medial anterior pin into the guide, stopping pin insertion prior to touching the shoulder against the guide. Under power, place a first shoulder pin into the medial hole of the Sizing Resection Guide. Place a second shoulder pin into the lateral hole of the guide. Advance the shoulder pins slowly using a ream setting. Disconnect the distractor handle, then using pin cutters, trim the medial anterior 2.4 mm smooth Steinmann Pin. Also, if not previously cut, trim the central pins on the tibial trial flush to the anterior surface to provide clearance for a talar plunging reamer.

The posterior talar chamfer cut may include evaluating access to the posterior cut slot within the talus trialing implant and cut guide. If access to the posterior cut slot is favorable, an oscillating saw blade may be used for the dorsal talar cut. Insert the saw blade into the posterior cut slot of the talus trialing implant and cut guide. Under power, the posterior saw cut is performed, taking care to avoid contact with the medial malleolus and fibula.

Figure 103:
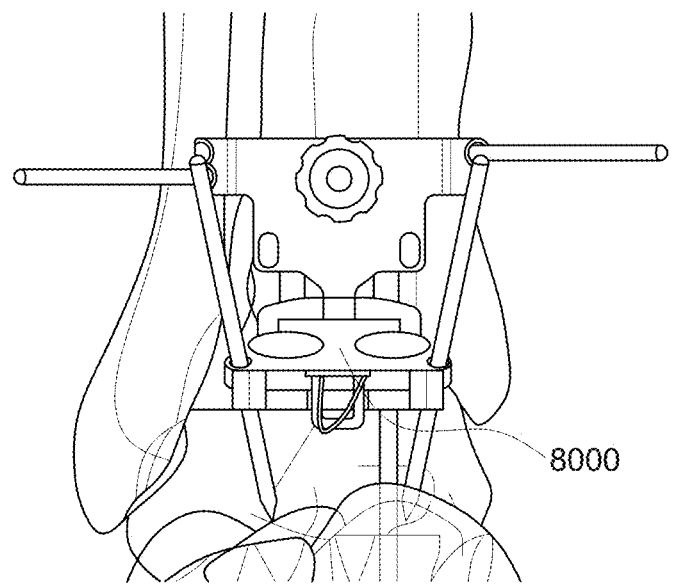
FIG. 103 is a perspective view of a detachable talus trialing implant and cut guide and a 2-holed resection insert, according to an embodiment of the present disclosure.
Figure 104:
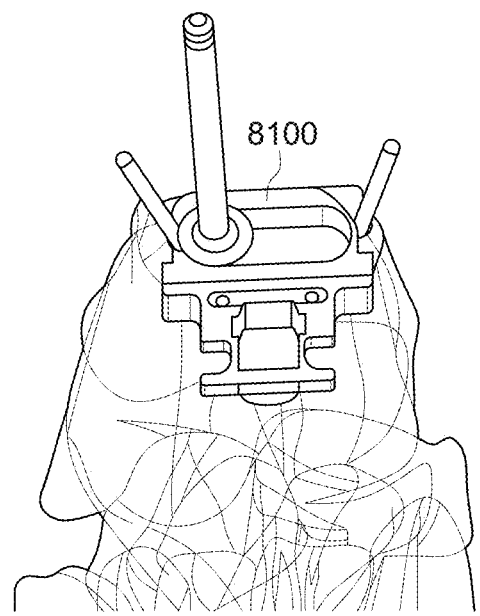
FIG. 104 is a perspective view of a detachable talus trialing implant and cut guide and a single slotted resection insert, according to an embodiment of the present disclosure.

For a chamfer-cut talar bone resection a 2-holed resection insert (e.g., insert 8000 as shown in FIG. 103) may be placed, corresponding to the size of the sizing resection guide, into the anterior window of the talus trialing implant and cut guide. A plunging reamer may be placed into one of the two anterior holes, holding it perpendicular to the 2-holed resection insert. Wait to start the reamer until lightly pressed against the cortical bone, and under power, ream until the plunging reamer bottoms out against the 2-holed resection insert. Then, repeat this reaming step for the second anterior hole, then remove the 2-holed resection Insert. A single-slotted resection insert (e.g., insert 8100 as shown in FIG. 104) may be placed in the anterior window of the talus trialing implant and cut guide. Using the plunging Reamer, slide the reamer from left to right until the bridge between the two reamed holes is resected, then remove the single-slotted resection insert. Thereafter, the threaded shoulder pins are removed from the talus trialing implant and cut guide, the medial anterior pin is removed from the talus trialing implant and cut guide as well, then the talus trialing implant and cut guide is removed. The chamfer cut may be checked and fin reamed. Sizing and cutting procedures that may be applicable to the use of the components disclosed above are shown and described in U.S. provisional application No. 62/779,092, entitled "Instruments, Guides And Related Methods For Total Ankle Replacement", and International PCT Patent Application, filed Dec. 13, 2019, entitled "Instruments, Guides And Related Methods For Total Ankle Replacement", which are hereby incorporated by reference in their entirety herein.

The above disclosure describes a portion of a total ankle replacement (TAR) procedure and the devices used in that procedure. Additional understanding of the TAR procedure may be found in U.S. Provisional Application No. 62/779,436 filed Dec. 13, 2018, and entitled Joint Replacement Systems and Methods of Use and Assembly, International Application No. PCT/US2019/029009 filed Apr. 24, 2019, and entitled Implants and Methods of Use and Assembly, U.S. Provisional Application No. 62/779,092 filed Dec. 13, 2018, and entitled Instruments, Guides and Related Methods for Total Ankle Replacement, International Application No. PCT/US2019/066404 filed Dec. 13, 2019, and entitled Instruments, Guides and Related Methods for Total Ankle Replacement, U.S. Provisional Application No. 62/890,611 filed Aug. 22, 2019, and entitled Patient Specific Instruments and Methods of Use, International Application No. PCT/US2019/066336 filed Dec. 13, 2019, and entitled Patient Specific Instruments and Methods of Use, U.S. Provisional Application No. 62/899,703 filed Sep. 12, 2019, and entitled Joint Replacement Alignment Guides, Systems and Methods of Use and Assembly, International Application No. PCT/US2019/066408 filed Dec. 13, 2019, and entitled Joint Replacement Alignment Guides, Systems and Methods of Use and Assembly, U.S. Provisional Patent Application No. 62/899,655, filed Sep. 12, 2019, and entitled Alignment Instruments And Methods For Use In Total Ankle Replacement, International Application No. PCT/US2019/066149, filed on Dec. 13, 2019, and entitled Alignment Instruments And Methods For Use In Total Ankle Replacement, U.S. Provisional Application No. 62/899,740 filed Sep. 12, 2019, and entitled Joint Replacement Alignment Guides, Systems and Methods of Use and Assembly, International Application No. PCT/US2019/066393 filed Dec. 13, 2019, and entitled Joint Replacement Alignment Guides, Systems and Methods of Use and Assembly, U.S. Provisional Application No. 62/898,615 filed Sep. 11, 2019, and entitled Resection Guides, Sweeping Reamers, and Methods for Use in Total Ankle Replacement, International Application No. PCT/US2019/064948 filed Dec. 6, 2019, and entitled Resection Guides, Sweeping Reamers, and Methods for Use in Total Ankle Replacement, U.S. Provisional Application No. 62/898,854 filed Sep. 11, 2019, and entitled Distractors Having Attachable Paddles, Impaction Devices, and Methods for Use in Total Ankle Replacement, International Application No. PCT/US2019/066398 filed Dec. 13, 2019, and entitled Distractors Having Attachable Paddles, Impaction Devices, and Methods for Use in Total Ankle Replacement, U.S. Provisional Application No. 62/899,646 filed Sep. 12, 2019, and entitled Trial Insert Assembly, International Application No. PCT/US2019/065025 filed Dec. 6, 2019, and entitled Trial Insert Assembly, U.S. Provisional Application No. 62/899,460 filed Sep. 12, 2019, and entitled Total Ankle Replacement Surgical Method, International Application No. PCT/US2019/066409 filed Dec. 13, 2019, and entitled Total Ankle Replacement Surgical Method, which are each hereby incorporated herein in their entireties.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features. Any examples of parameters are not exclusive of other parameters of the disclosed embodiments.

As used herein, the terms "comprising," "has," "including," "containing," and other grammatical variants thereof encompass the terms "consisting of" and "consisting essentially of." The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

All publications cited in this specification are herein incorporated by reference as if each individual publication were specifically and individually indicated to be incorporated by reference herein as though fully set forth.

Where one or more ranges are referred to throughout this specification, each range is intended to be a shorthand format for presenting information, where the range is understood to encompass each discrete point within the range as if the same were fully set forth herein.

It is to be understood that the above description is intended to be illustrative, and not restrictive. Numerous changes and modifications may be made herein by one of ordinary skill in the art without departing from the general spirit and scope of the invention as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments.

Components, aspects, features, configurations, arrangements, uses and the like described, illustrated or otherwise disclosed herein with respect to any particular embodiment may be similarly applied to any other embodiment disclosed herein. Accordingly, the inventions are not to be seen as limited by the foregoing description, but is only limited by the scope of the appended claims.

This written description uses examples to disclose the inventions, including the best mode, and also to enable any person skilled in the art to practice the inventions, including making and using any devices or systems and performing any incorporated methods. The patentable scope of the inventions are defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A distractor system for use in a joint between two bone surfaces of an anatomical structure, said distractor system comprising:
   a first pivotable member having a first user engageable arm and an opposite first end;
   a second pivotable member having a second user engageable arm and an opposite second end, said first pivotable member pivotably connected to said second pivotable member between said user engageable arms and said ends;

a first connecting member having a first end and a second end, said first end pivotally connected to said first end of said first pivotable member;

a second connecting member having a first end and a second end, said first end pivotally connected to said second end of said second pivotable member;

a biasing member for biasing said first arm away from said second arm so that said second end of said first connecting member is biased towards said second end of said second connecting member; and at least one detachable tool comprising a first detachable tool comprising:

a proximal portion comprising a recess configured to facilitate releasable coupling with at least one of said second end of said first connecting member and/or said second end of said second connecting member; and a distal portion operably positionable in the joint between the two bone surfaces of the anatomical structure, wherein the distal portion comprises a planar surface and at least one cutting and/or punch pin disposed on the planar surface, each of said at least one cutting and/or punch pin defining a longitudinal axis disposed substantially orthogonally to the planar surface, and wherein said at least one cutting and/or punch pin comprises longitudinal serrations that extend a distance greater than a radius of the at least one cutting and/or punch pin.

2. The distractor system of claim 1, wherein said at least one cutting and/or punch pin comprises a plurality of cutting and/or punch pins disposed perpendicular to a longitudinal axis of said distal portion.

3. The distractor system of claim 2, wherein the distal portion is elongated along a second longitudinal axis, wherein a distal end of the distal portion defines a free end a free end of the at least one detachable tool of the at least one detachable tool along the second longitudinal axis, and wherein the plurality of cutting and/or punch pins are positioned at the distal end of the distal portion.

4. The distractor system of claim 2, wherein the at least one detachable tool further comprises a tibial trial component comprising a base portion with a distal side and a bone engagement side opposing the distal side, the bone engagement side at least partially corresponding to a tibial implant component of a total ankle replacement prosthesis, wherein the base portion of the tibial trial component comprises a plurality of through holes extending between the distal side and the bone engagement side thereof, and wherein the physical arrangements of the plurality of through holes and the plurality of cutting and/or punch pins correspond to each other.

5. The distractor system of claim 1, wherein said proximal portion comprises a first longitudinal axis and said distal portion comprises a second longitudinal axis offset from said first longitudinal axis.

6. The distractor system of claim 1, wherein said distal portion comprises radiographic marker.

7. The distractor system of claim 1, wherein said at least one detachable tool further comprises a plurality of detachable paddles, a detachable resection guide, and a detachable implant trialing and cutting guide.

8. The distractor system of claim 1, wherein said second end of said first connecting member comprises a first post, and said second end of said second connecting member comprises a second post.

9. The distractor system of claim 8, wherein said first post comprises a first axis, said second post comprises a second axis, and said first axis being maintained parallel to said second axis.

10. The distractor system of claim 1, wherein said second end of said first connecting member comprises a first post having a laterally-extending projection, and said second end of said second connecting member comprises a second post having a laterally-extending projection.

11. The distractor system of claim 1, further comprising a ratchet pivotally attached to said second arm and selectively releasably attachable to said first arm, and a scissors mechanism for connecting said first connecting member to said second connecting member and operably movably to maintain said first connecting member to be parallel to said second connecting member.

12. The distractor system of claim 1, wherein said at least one detachable tool is sized for being received between two bone surfaces of an ankle joint.

13. The distractor system of claim 1, wherein said at least one detachable tool is sized for being received between a tibia and a talus of an ankle joint.

14. The distractor system of claim 1, wherein the distal portion is elongated along a second longitudinal axis, wherein the at least one cutting and/or punch pin comprises a pair of cutting and/or punch pins that are spaced along a lateral direction that is oriented orthogonally to the second longitudinal axis, and wherein the planar surface extends laterally between the pair of cutting and/or punch pins.

15. The distractor system of claim 1, wherein the at least one detachable tool further comprises a tibial trial component comprising a base portion with a distal side and a bone engagement side opposing the distal side that is configured to engage a distal tibia, the bone engagement side at least partially corresponding to a tibial implant component of a total ankle replacement prosthesis, and wherein the distal side of the tibial trial component comprises a recess configured to mate with the distal portion of the first detachable tool to couple the first detachable tool and the tibial trial component together.

16. The distractor system of claim 15, wherein the at least one cutting and/or punch pin of the first detachable tool comprises a plurality of cutting and/or punch pins, wherein the base portion of the tibial trial component comprises a plurality of through holes extending between the distal side and the bone engagement side thereof, and wherein the physical arrangements of the plurality of cutting and/or punch pins and the plurality of through holes correspond to each other such that the plurality of cutting and/or punch pins extend through the plurality of through holes when the first detachable tool and the tibial trial component are coupled together.

17. A surgical method comprising:

providing the distractor of claim 1;

attaching the proximal portion of the first detachable tool with the second end of the first connecting member of the distractor or with the second end of the second connecting member of the distractor;

inserting the first detachable tool in the joint between the two bone surfaces of the anatomical structure; and applying a force to the distractor to force the at least one cutting and/or punch pin of the first detachable tool into one of the two bone surfaces.

18. A distractor system for use in a joint between two bone surfaces of an anatomical structure, said distractor system comprising:
- a first pivotable member having a first user engageable arm and an opposite first end;
- a second pivotable member having a second user engageable arm and an opposite second end, said first pivotable member pivotably connected to said second pivotable member between said user engageable arms and said ends;
- a first connecting member having a first end and a second end, said first end pivotally connected to said first end of said first pivotable member;
- a second connecting member having a first end and a second end, said first end pivotally connected to said second end of said second pivotable member;
- a biasing member for biasing said first arm away from said second arm so that said second end of said first connecting member is biased towards said second end of said second connecting member; and
- at least one detachable tool comprising a first detachable tool comprising a proximal portion and a distal portion, said proximal portion comprising a recess configured to facilitate releasable attachment to at least one of said second end of said first connection member and/or said second end of said second connecting member, said distal portion being operably positionable in the joint between the two bone surfaces of the anatomical structure,
- wherein the distal portion comprises a planar surface and at least one cutting and/or punch pin extending proximately from the planar surface on a proximate side of the distal portion, each of said at least one cutting and/or punch pin defining a first longitudinal axis disposed substantially orthogonally to the planar surface,
- wherein said distal portion comprises a second longitudinal axis that is orthogonal to the first longitudinal axis, and
- wherein a distal side of the distal portion that opposes the proximate side thereof comprises a radiographic marker that extends perpendicular to said second longitudinal axis.

19. The distractor system of claim 18, wherein said distal portion of said at least one detachable tool comprises a detachable paddle.

20. The distractor system of claim 19, wherein a surface of said distal portion of said detachable paddle comprises a raised center portion and a recessed peripheral portion.

21. The distractor system of claim 18, wherein said distal portion of said at least one detachable tool comprises a detachable resection guide.

22. The distractor system of claim 18, wherein said distal portion of said at least one detachable tool comprises a detachable implant trialing and cutting guide.

23. The distractor system of claim 18, wherein said proximal portion comprises a first longitudinal axis, and said distal portion comprises a second longitudinal axis offset from said first longitudinal axis.

24. The distractor system of claim 18, wherein said at least one detachable tool further comprises a plurality of detachable paddles, a detachable resection guide, and a detachable implant trialing and cutting guide.

25. The distractor system of claim 18, wherein said second end of said first connecting member comprises a first post, and said second end of said second connecting member comprises a second post.

26. The distractor system of claim 25, wherein said first post comprises a first axis, said second post comprises a second axis, and wherein said first axis is parallel to said second axis.

27. The distractor system of claim 25, wherein said first post comprises a laterally-extending projection, and said second post comprises a laterally-extending projection.

28. The distractor system of claim 18, further comprising a ratchet pivotally attached to said second arm and selectively releasably attachable to said first arm, and a scissors mechanism for connecting said first connecting member to said second connecting member and operably movably to maintain said first connecting member to be parallel to said second connecting member.

29. The distractor system of claim 18, wherein said at least one detachable tool is sized for being received between two bone surfaces of an ankle joint.

30. The distractor system of claim 18, wherein said at least one detachable tool is sized for being received between a tibia and a talus of an ankle joint.

31. A surgical method comprising:
- providing the distractor system of claim 18;
- attaching the first detachable tool to one of said second end of said first connection member or said second end of said second connecting member; and
- inserting the at least one detachable tool in the joint between the bone surfaces of the anatomical structure.

32. The method of claim 31, further comprising applying a compressive force to the arms of the distractor to separate the two bone surfaces.

* * * * *

UNITED STATES PATENT AND TRADEMARK OFFICE
CERTIFICATE OF CORRECTION

| | |
|---|---|
| PATENT NO. | : 11,464,522 B2 |
| APPLICATION NO. | : 17/345402 |
| DATED | : October 11, 2022 |
| INVENTOR(S) | : Dalton et al. |

It is certified that error appears in the above-identified patent and that said Letters Patent is hereby corrected as shown below:

In the Claims

Column 27, Line 42: Claim 3, Delete "a free end a free end of the at least one detachable tool of the at least one detachable tool" and insert -- a free end of the at least one detachable tool --

Signed and Sealed this
Twenty-second Day of November, 2022

Katherine Kelly Vidal
*Director of the United States Patent and Trademark Office*